US011332730B2

(12) United States Patent
Chen et al.

(10) Patent No.: US 11,332,730 B2
(45) Date of Patent: May 17, 2022

(54) ENGINEERED DECARBOXYLASE POLYPEPTIDES AND THEIR APPLICATION IN PREPARING BETA-ALANINE

(71) Applicant: Enzymaster (Ningbo) Bio-Engineering Co., Ltd., Ningbo (CN)

(72) Inventors: Haibin Chen, Ningbo (CN); Yong Koy Bong, Ningbo (CN); Wenhui Zheng, Ningbo (CN); Zhaoqi Zhang, Ningbo (CN); Kuifang He, Ningbo (CN); Chengxiao Zhang, Ningbo (CN); Lei Sun, Ningbo (CN); Yingxin Zhang, Ningbo (CN)

(73) Assignee: Enzymaster (Ningbo) Bio-Engineering Co., Ltd., Ningbo (CN)

( * ) Notice: Subject to any disclaimer, the term of this patent is extended or adjusted under 35 U.S.C. 154(b) by 20 days.

(21) Appl. No.: 16/648,919

(22) PCT Filed: Sep. 28, 2018

(86) PCT No.: PCT/CN2018/108478
§ 371 (c)(1),
(2) Date: Mar. 19, 2020

(87) PCT Pub. No.: WO2019/062874
PCT Pub. Date: Apr. 4, 2019

(65) Prior Publication Data
US 2020/0248163 A1 Aug. 6, 2020

(30) Foreign Application Priority Data
Oct. 1, 2017 (CN) .......................... 201710924714.5

(51) Int. Cl.
*C12N 9/88* (2006.01)
*C12N 11/00* (2006.01)
*C12P 13/06* (2006.01)
*C12N 11/08* (2020.01)

(52) U.S. Cl.
CPC ................ *C12N 9/88* (2013.01); *C12N 11/00* (2013.01); *C12N 11/08* (2013.01); *C12P 13/06* (2013.01)

(58) Field of Classification Search
None
See application file for complete search history.

(56) References Cited

PUBLICATIONS

PDF NCBI Reference Sequence : WP_074506212.1. Downloaded on Jun. 16, 2021. (Year: 2021).*
NCBI Reference Sequence: WP_006768557.1, "aspartate 1-decarboxylase [Corynebacterium efficiens]", (Apr. 27, 2015).
NCBI Reference Sequence: WP_015650064.1, "aspartate 1-decarboxylase [Corynebacterium callunae]", (Nov. 24, 2015).
NCBI Reference Sequence: WP_003857183.1, "Multispecies: aspartate 1-decarboxylase [Corynebacterium]", (Apr. 27, 2015).

* cited by examiner

*Primary Examiner* — Anand U Desai
(74) *Attorney, Agent, or Firm* — Smith Patent, LLC; Chalin A. Smith

(57) ABSTRACT

The present invention provides amino acid sequences of engineered decarboxylase polypeptides that are useful for catalyzing the decarboxylation of L-aspartate to produce β-alanine, and the preparation process of engineered decarboxylase polypeptides as well as reaction process under industrial-relevant conditions. The present disclosure also provides polynucleotide sequences encoding engineered decarboxylase polypeptides, engineered host cells capable of expressing engineered decarboxylase polypeptides, and methods of producing β-alanine using the engineered cells. Compared to the wild-type decarboxylase, the engineered decarboxylase polypeptide provided by the invention has better activity and stability, and overcomes the inhibition by L-aspartic acid and/or β-alanine. The use of the engineered polypeptides of the present invention for the preparation of β-alanine results in higher unit activity, lower cost, and has good industrial application prospects.

12 Claims, No Drawings
Specification includes a Sequence Listing.

SEQUENCE LISTING

```
<160> NUMBER OF SEQ ID NOS: 390

<210> SEQ ID NO 1
<211> LENGTH: 408
<212> TYPE: DNA
<213> ORGANISM: Artificial sequence
<220> FEATURE:
<223> OTHER INFORMATION: Engineered sequence

<400> SEQUENCE: 1
atgctgcgta ccatcctggg ttcaaaaatc catcgtgcaa cggtgacgca agcggacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 2
<211> LENGTH: 136
<212> TYPE: PRT
<213> ORGANISM: Corynebacterium glutamicum
```

<400> SEQUENCE: 2

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Lys Ile Val His Val Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135

<210> SEQ ID NO 3
<211> LENGTH: 408
<212> TYPE: DNA
<213> ORGANISM: Artificial sequence
<220> FEATURE:
<223> OTHER INFORMATION: Engineered sequence

<400> SEQUENCE: 3
atgctgcgta ccatcctggg ttcaaaaatc catcgtgcaa cgactacgca agcggacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 4
<211> LENGTH: 136
<212> TYPE: PRT
<213> ORGANISM: Artificial sequence
<220> FEATURE:
<223> OTHER INFORMATION: Engineered sequence

<400> SEQUENCE: 4

Met Leu Arg Thr Ile Leu Gly Ser Lys Ile His Arg Ala Thr Thr Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

```
Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
130                 135
```

<210> SEQ ID NO 5
<211> LENGTH: 408
<212> TYPE: DNA
<213> ORGANISM: Artificial sequence
<220> FEATURE:
<223> OTHER INFORMATION: Engineered sequence

<400> SEQUENCE: 5

```
atgctgcgta ccatcctggg ttcaaaaatc catcgtgcaa cgattacgca agcggacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat      360
ctggcggaag ccctgccggg tagcggtctg ctgacgagcc gtagtatt                  408
```

<210> SEQ ID NO 6
<211> LENGTH: 136
<212> TYPE: PRT
<213> ORGANISM: Artificial sequence
<220> FEATURE:
<223> OTHER INFORMATION: Engineered sequence

<400> SEQUENCE: 6

```
Met Leu Arg Thr Ile Leu Gly Ser Lys Ile His Arg Ala Thr Ile Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
130                 135
```

<210> SEQ ID NO 7
<211> LENGTH: 408
<212> TYPE: DNA
<213> ORGANISM: Artificial sequence
<220> FEATURE:
<223> OTHER INFORMATION: Engineered sequence

<400> SEQUENCE: 7

```
atgctgcgta ccatcctggg ttcaaaaatc catcgtgcaa cggtgacgca aagtgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg acaaccgca tcgttgccct gggcaatgat   360
ctggcggaag ccctgccggg tagcggtctg ctgacgagcc gtagtatt              408
```

<210> SEQ ID NO 8
<211> LENGTH: 136
<212> TYPE: PRT
<213> ORGANISM: Artificial sequence
<220> FEATURE:
<223> OTHER INFORMATION: Engineered sequence

<400> SEQUENCE: 8

```
Met Leu Arg Thr Ile Leu Gly Ser Lys Ile His Arg Ala Thr Val Thr
1               5                   10                  15
Gln Ser Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 9
<211> LENGTH: 408
<212> TYPE: DNA
<213> ORGANISM: Artificial sequence
<220> FEATURE:
<223> OTHER INFORMATION: Engineered sequence

<400> SEQUENCE: 9

```
atgctgcgta ccatcctggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg acaaccgca tcgttgccct gggcaatgat    360
ctggcggaag ccctgccggg tagcggtctg ctgacgagcc gtagtatt              408
```

<210> SEQ ID NO 10
<211> LENGTH: 136
<212> TYPE: PRT
<213> ORGANISM: Artificial sequence
<220> FEATURE:
<223> OTHER INFORMATION: Engineered sequence

<400> SEQUENCE: 10

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 11
<211> LENGTH: 408
<212> TYPE: DNA
<213> ORGANISM: Artificial sequence
<220> FEATURE:
<223> OTHER INFORMATION: Engineered sequence

<400> SEQUENCE: 11

```
atgctgcgta ccatcctggg ttcaaaaatc catcgtgcaa cggtgacgca agcggacctg      60
cattatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt             408
```

<210> SEQ ID NO 12
<211> LENGTH: 136
<212> TYPE: PRT
<213> ORGANISM: Artificial sequence
<220> FEATURE:
<223> OTHER INFORMATION: Engineered sequence

<400> SEQUENCE: 12

```
Met Leu Arg Thr Ile Leu Gly Ser Lys Ile His Arg Ala Thr Val Thr
1               5                   10                  15

Gln Ala Asp Leu His Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45
```

```
Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                    85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 13
<211> LENGTH: 408
<212> TYPE: DNA
<213> ORGANISM: Artificial sequence
<220> FEATURE:
<223> OTHER INFORMATION: Engineered sequence

<400> SEQUENCE: 13
atgctgcgta ccatcctggg ttcaaaaatc catcgtgcaa cggtgacgca agcggacctg      60
gactatgtgg ttctgtcac cattgatgca gacctggtcc atgcagcagg tctgatcatt     120
ggtgaaaaag ttgcaattgt cgatatcacc aacggcgctc gtctgaaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 14
<211> LENGTH: 136
<212> TYPE: PRT
<213> ORGANISM: Artificial sequence
<220> FEATURE:
<223> OTHER INFORMATION: Engineered sequence

<400> SEQUENCE: 14

Met Leu Arg Thr Ile Leu Gly Ser Lys Ile His Arg Ala Thr Val Thr
 1               5                  10                  15

Gln Ala Asp Leu Asp Tyr Val Gly Ser Val Thr Ile Asp Ala Asp Leu
                20                  25                  30

Val His Ala Ala Gly Leu Ile Ile Gly Glu Lys Val Ala Ile Val Asp
            35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                    85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135
```

<210> SEQ ID NO 15
<211> LENGTH: 408
<212> TYPE: DNA
<213> ORGANISM: Artificial sequence
<220> FEATURE:
<223> OTHER INFORMATION: Engineered sequence

<400> SEQUENCE: 15

```
atgctgcgta ccatcctggg ttcaaaaatc catcgtgcaa cggtgacgca agcggacctg      60
gactatgtgg gttctgtcac cattgatgca gacctggtcc atgcagcagg tctgatcgtt     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat      360
ctggcggaag ccctgccggg tagcggtctg ctgacgagcc gtagtatt                   408
```

<210> SEQ ID NO 16
<211> LENGTH: 136
<212> TYPE: PRT
<213> ORGANISM: Artificial sequence
<220> FEATURE:
<223> OTHER INFORMATION: Engineered sequence

<400> SEQUENCE: 16

```
Met Leu Arg Thr Ile Leu Gly Ser Lys Ile His Arg Ala Thr Val Thr
1               5                   10                  15
Gln Ala Asp Leu Asp Tyr Val Gly Ser Val Thr Ile Asp Ala Asp Leu
            20                  25                  30
Val His Ala Ala Gly Leu Ile Val Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 17
<211> LENGTH: 408
<212> TYPE: DNA
<213> ORGANISM: Artificial sequence
<220> FEATURE:
<223> OTHER INFORMATION: Engineered sequence

<400> SEQUENCE: 17

```
atgctgcgta ccatcctggg ttcaaaaatc catcgtgcaa cggtgacgca agcggacctg      60
gactatgtgg gttctgtcac cattgatgca gacctggtcc atgcagcagg tctgatcgaa     120
ggtgaaaaag ttcagattgt cgatatcacc aacggcgctc gtctggaaac gtatgtaatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
```

```
tacgaaccga aaattgtcca cgtggatgcg gacaaccgca tcgttgccct gggcaatgat      360
ctggcggaag ccctgccggg tagcggtctg ctgacgagcc gtagtatt                   408
```

<210> SEQ ID NO 18
<211> LENGTH: 136
<212> TYPE: PRT
<213> ORGANISM: Artificial sequence
<220> FEATURE:
<223> OTHER INFORMATION: Engineered sequence

<400> SEQUENCE: 18

```
Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Lys Val Gln Ile Val Asp
    35                  40                  45

Ile Thr Asn Gly Ala Arg Leu Glu Thr Tyr Val Ile Val Gly Asp Ala
50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 19
<211> LENGTH: 408
<212> TYPE: DNA
<213> ORGANISM: Artificial sequence
<220> FEATURE:
<223> OTHER INFORMATION: Engineered sequence

<400> SEQUENCE: 19

```
atgctgcgta ccatcctggg ttcaaaaatc catcgtgcaa cggtgacgca agcggacctg       60
gactatgtgg ttctgtcac cattgatgca gacctggtcc atgcagcagg tctgatcgaa      120
ggtgaaaaag tttgattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccctgccggg tagcggtctg ctgacgagcc gtagtatt                   408
```

<210> SEQ ID NO 20
<211> LENGTH: 136
<212> TYPE: PRT
<213> ORGANISM: Artificial sequence
<220> FEATURE:
<223> OTHER INFORMATION: Engineered sequence

<400> SEQUENCE: 20

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
                20                  25                  30

Val His Ala Ala Gly Leu Ile Glu Gly Glu Lys Val Leu Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Lys Ile Val His Val Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 21
<211> LENGTH: 408
<212> TYPE: DNA
<213> ORGANISM: Artificial sequence
<220> FEATURE:
<223> OTHER INFORMATION: Engineered sequence

<400> SEQUENCE: 21
atgctgcgta ccatcctggg ttcaaaaatc catcgtgcaa cggtgacgca agcggacctg      60
gactatgtgg ttctgtcac cattgatgca gacctggtcc atgcagcagg tctgatcgaa      120
ggtgaaaaag ttgcatgtgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 22
<211> LENGTH: 136
<212> TYPE: PRT
<213> ORGANISM: Artificial sequence
<220> FEATURE:
<223> OTHER INFORMATION: Engineered sequence

<400> SEQUENCE: 22

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
                20                  25                  30

Val His Ala Ala Gly Leu Ile Glu Gly Glu Lys Val Ala Cys Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala Ala His Leu Ile Asn
65                  70                  75                  80

```
Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 23
<211> LENGTH: 408
<212> TYPE: DNA
<213> ORGANISM: Artificial sequence
<220> FEATURE:
<223> OTHER INFORMATION: Engineered sequence

<400> SEQUENCE: 23
atgctgcgta ccatcctggg ttcaaaaatc catcgtgcaa cggtgacgca agcggacctg      60
gactatgtgg gttctgtcac cattgatgca gacctggtcc atgcagcagg tctgatcgaa     120
ggtgaaaaag ttgcaattgt cgatatcacc aacggcgatc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 24
<211> LENGTH: 136
<212> TYPE: PRT
<213> ORGANISM: Artificial sequence
<220> FEATURE:
<223> OTHER INFORMATION: Engineered sequence

<400> SEQUENCE: 24

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Asp Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 25
<211> LENGTH: 408
<212> TYPE: DNA
<213> ORGANISM: Artificial sequence
```

<220> FEATURE:
<223> OTHER INFORMATION: Engineered sequence

<400> SEQUENCE: 25

| atgctgcgta ccatcctggg ttcaaaaatc catcgtgcaa cggtgacgca agcggacctg | 60 |
| gactatgtgg ttctgtcac cattgatgca gacctggtcc atgcagcagg tctgatcgaa | 120 |
| ggtgaaaaag ttgcaattgt cgatatcacc aacggcgagc gtctggaaac gtatgtgatt | 180 |
| gttggtgatg cgggcaccgg taacatttgc atcaatggcg cagctgcgca tctgatcaat | 240 |
| ccgggtgatc tggtgattat catgagctat ctgcaggcca cggacgccga agcaaaggct | 300 |
| tacgaaccga aaattgtcca cgtggatgcg gacaaccgca tcgttgccct gggcaatgat | 360 |
| ctggcggaag ccctgccggg tagcggtctg ctgacgagcc gtagtatt | 408 |

<210> SEQ ID NO 26
<211> LENGTH: 136
<212> TYPE: PRT
<213> ORGANISM: Artificial sequence
<220> FEATURE:
<223> OTHER INFORMATION: Engineered sequence

<400> SEQUENCE: 26

Met Leu Arg Thr Ile Leu Gly Ser Lys Ile His Arg Ala Thr Val Thr
1               5                   10                  15
Gln Ala Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Glu Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135

<210> SEQ ID NO 27
<211> LENGTH: 408
<212> TYPE: DNA
<213> ORGANISM: Artificial sequence
<220> FEATURE:
<223> OTHER INFORMATION: Engineered sequence

<400> SEQUENCE: 27

| atgctgcgta ccatcctggg ttcaaaaatc catcgtgcaa cggtgacgca agcggacctg | 60 |
| gactatgtgg ttctgtcac catttcggca gacctggtcc atgcagcagg tctgatcgaa | 120 |
| ggtgaaaaag ttgcaattgt cgatatcacc aacggcgctc gtctggaaac gtatgtgatt | 180 |
| gttggtgatg cgggcaccgg taacatttgc atcaatggcg cagctgcgca tctgatcaat | 240 |
| ccgggtgatc tggtgattat catgagctat ctgcaggcca cggacgccga agcaaaggct | 300 |
| tacgaaccga aaattgtcca cgtggatgcg gacaaccgca tcgttgccct gggcaatgat | 360 |
| ctggcggaag ccctgccggg tagcggtctg ctgacgagcc gtagtatt | 408 |

```
<210> SEQ ID NO 28
<211> LENGTH: 136
<212> TYPE: PRT
<213> ORGANISM: Artificial sequence
<220> FEATURE:
<223> OTHER INFORMATION: Engineered sequence

<400> SEQUENCE: 28

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Ser Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 29
<211> LENGTH: 408
<212> TYPE: DNA
<213> ORGANISM: Artificial sequence
<220> FEATURE:
<223> OTHER INFORMATION: Engineered sequence

<400> SEQUENCE: 29
atgctgcgta ccatcctggg ttcaaaaatc catcgtgcaa cggtgacgca agcggacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatt ggggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat      360
ctggcggaag ccctgccggg tagcggtctg ctgacgagcc gtagtatt                  408

<210> SEQ ID NO 30
<211> LENGTH: 136
<212> TYPE: PRT
<213> ORGANISM: Artificial sequence
<220> FEATURE:
<223> OTHER INFORMATION: Engineered sequence

<400> SEQUENCE: 30

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45
```

```
Ile Thr Asn Gly Ala Arg Leu Glu Thr Tyr Val Ile Val Gly Asp Trp
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 31
<211> LENGTH: 408
<212> TYPE: DNA
<213> ORGANISM: Artificial sequence
<220> FEATURE:
<223> OTHER INFORMATION: Engineered sequence

<400> SEQUENCE: 31
atgctgcgta ccatcctggg ttcaaaaatc catcgtgcaa cggtgacgca agcggacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccaa taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                 408

<210> SEQ ID NO 32
<211> LENGTH: 136
<212> TYPE: PRT
<213> ORGANISM: Artificial sequence
<220> FEATURE:
<223> OTHER INFORMATION: Engineered sequence

<400> SEQUENCE: 32

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
                20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
    50                  55                  60

Gly Thr Asn Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135
```

<210> SEQ ID NO 33
<211> LENGTH: 408
<212> TYPE: DNA
<213> ORGANISM: Artificial sequence
<220> FEATURE:
<223> OTHER INFORMATION: Engineered sequence

<400> SEQUENCE: 33

```
atgctgcgta ccatcctggg ttcaaaaatc catcgtgcaa cggtgacgca agcggacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaagctg     300
tacgaaccga aaattgtcca cgtggatgcg acaaccgca tcgttgccct gggcaatgat     360
ctggcggaag ccctgccggg tagcggtctg ctgacgagcc gtagtatt                 408
```

<210> SEQ ID NO 34
<211> LENGTH: 136
<212> TYPE: PRT
<213> ORGANISM: Artificial sequence
<220> FEATURE:
<223> OTHER INFORMATION: Engineered sequence

<400> SEQUENCE: 34

```
Met Leu Arg Thr Ile Leu Gly Ser Lys Ile His Arg Ala Thr Val Thr
1               5                   10                  15
Gln Ala Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Leu Tyr Glu Pro Lys Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 35
<211> LENGTH: 408
<212> TYPE: DNA
<213> ORGANISM: Artificial sequence
<220> FEATURE:
<223> OTHER INFORMATION: Engineered sequence

<400> SEQUENCE: 35

```
atgctgcgta ccatcctggg ttcaaaaatc catcgtgcaa cggtgacgca agcggacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
```

```
tacgaagcta aaattgtcca cgtggatgcg gacaaccgca tcgttgccct gggcaatgat    360
ctggcggaag ccctgccggg tagcggtctg ctgacgagcc gtagtatt              408
```

<210> SEQ ID NO 36
<211> LENGTH: 136
<212> TYPE: PRT
<213> ORGANISM: Artificial sequence
<220> FEATURE:
<223> OTHER INFORMATION: Engineered sequence

<400> SEQUENCE: 36

```
Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
    35                  40                  45

Ile Thr Asn Gly Ala Arg Leu Glu Thr Tyr Val Ile Val Gly Asp Ala
50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Ala Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 37
<211> LENGTH: 408
<212> TYPE: DNA
<213> ORGANISM: Artificial sequence
<220> FEATURE:
<223> OTHER INFORMATION: Engineered sequence

<400> SEQUENCE: 37

```
atgctgcgta ccatcctggg ttcaaaaatc catcgtgcaa cggtgacgca agcggacctg    60
gactatgtgg ttctgtcac cattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacacgccga aaattgtcca cgtggatgcg gacaaccgca tcgttgccct gggcaatgat    360
ctggcggaag ccctgccggg tagcggtctg ctgacgagcc gtagtatt              408
```

<210> SEQ ID NO 38
<211> LENGTH: 136
<212> TYPE: PRT
<213> ORGANISM: Artificial sequence
<220> FEATURE:
<223> OTHER INFORMATION: Engineered sequence

<400> SEQUENCE: 38

Met Leu Arg Thr Ile Leu Gly Ser Lys Ile His Arg Ala Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Thr Pro Lys Ile Val His Val Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135

<210> SEQ ID NO 39
<211> LENGTH: 408
<212> TYPE: DNA
<213> ORGANISM: Artificial sequence
<220> FEATURE:
<223> OTHER INFORMATION: Engineered sequence

<400> SEQUENCE: 39
atgctgcgta ccatcctggg ttcaaaaatc catcgtgcaa cggtgacgca agcggacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattttgca cgtggatgcg gacaaccgca tcgttgccct gggcaatgat     360
ctggcggaag ccctgccggg tagcggtctg ctgacgagcc gtagtatt                  408

<210> SEQ ID NO 40
<211> LENGTH: 136
<212> TYPE: PRT
<213> ORGANISM: Artificial sequence
<220> FEATURE:
<223> OTHER INFORMATION: Engineered sequence

<400> SEQUENCE: 40

Met Leu Arg Thr Ile Leu Gly Ser Lys Ile His Arg Ala Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

```
Pro Gly Asp Leu Val Ile Ile Met Ser Tyr Leu Gln Ala Thr Asp Ala
                85                  90                  95

Glu Ala Lys Ala Tyr Glu Pro Lys Ile Leu His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 41
<211> LENGTH: 408
<212> TYPE: DNA
<213> ORGANISM: Artificial sequence
<220> FEATURE:
<223> OTHER INFORMATION: Engineered sequence

<400> SEQUENCE: 41
atgctgcgta ccatcctggg ttcaaaaatc catcgtgcaa cggtgacgca agcggacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattattca cgtggatgcg acaaccgca tcgttgccct gggcaatgat      360
ctggcggaag ccctgccggg tagcggtctg ctgacgagcc gtagtatt                  408

<210> SEQ ID NO 42
<211> LENGTH: 136
<212> TYPE: PRT
<213> ORGANISM: Artificial sequence
<220> FEATURE:
<223> OTHER INFORMATION: Engineered sequence

<400> SEQUENCE: 42

Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 43
<211> LENGTH: 408
<212> TYPE: DNA
<213> ORGANISM: Artificial sequence
<220> FEATURE:
```

<223> OTHER INFORMATION: Engineered sequence

<400> SEQUENCE: 43

```
atgctgcgta ccatcctggg ttcaaaaatc catcgtgcaa cggtgacgca agcggacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtgactgcg gacaaccgca tcgttgccct gggcaatgat   360
ctggcggaag ccctgccggg tagcggtctg ctgacgagcc gtagtatt              408
```

<210> SEQ ID NO 44
<211> LENGTH: 136
<212> TYPE: PRT
<213> ORGANISM: Artificial sequence
<220> FEATURE:
<223> OTHER INFORMATION: Engineered sequence

<400> SEQUENCE: 44

```
Met Leu Arg Thr Ile Leu Gly Ser Lys Ile His Arg Ala Thr Val Thr
1               5                   10                  15
Gln Ala Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 45
<211> LENGTH: 408
<212> TYPE: DNA
<213> ORGANISM: Artificial sequence
<220> FEATURE:
<223> OTHER INFORMATION: Engineered sequence

<400> SEQUENCE: 45

```
atgctgcgta ccatcctggg ttcaaaaatc catcgtgcaa cggtgacgca agcggacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccgt atattgtcca cgtggatgcg gacaacggta tcgttgccct gggcaatgat   360
ctggcggaag ccctgccggg tagcggtctg ctgacgagcc gtagtatt              408
```

<210> SEQ ID NO 46
<211> LENGTH: 136
<212> TYPE: PRT
<213> ORGANISM: Artificial sequence
<220> FEATURE:
<223> OTHER INFORMATION: Engineered sequence

<400> SEQUENCE: 46

```
Met Leu Arg Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Tyr Ile Val His Val Ala Asp Asn
            100                 105                 110

Gly Ile Val Ala Leu Gly Asn Asp Leu Ala Glu Ala Leu Pro Gly Ser
        115                 120                 125

Gly Leu Leu Thr Ser Arg Ser Ile
        130                 135
```

<210> SEQ ID NO 47
<211> LENGTH: 408
<212> TYPE: DNA
<213> ORGANISM: Artificial sequence
<220> FEATURE:
<223> OTHER INFORMATION: Engineered sequence

<400> SEQUENCE: 47

```
atgctgcgta ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcacctt taacatttgc atcaatggcg cagctgcgca tctgatcaat     240
ccgggtgatc tggtgattat catgagctat ctgcaggcca cggacgccga agcaaaggca     300
tacgaaccga aaattgtcca cgtgacggcg gacaaccgca tcgttgccct gggcaatgat     360
ctggcggaag ccctgccggg tagcggtctg ctgacgagcc gtagtatt                  408
```

<210> SEQ ID NO 48
<211> LENGTH: 136
<212> TYPE: PRT
<213> ORGANISM: Artificial sequence
<220> FEATURE:
<223> OTHER INFORMATION: Engineered sequence

<400> SEQUENCE: 48

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45
```

Ile Thr Asn Gly Ala Arg Leu Glu Thr Tyr Val Ile Val Gly Asp Ala
        50                  55                  60

Gly Thr Phe Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
        130                 135

<210> SEQ ID NO 49
<211> LENGTH: 408
<212> TYPE: DNA
<213> ORGANISM: Artificial sequence
<220> FEATURE:
<223> OTHER INFORMATION: Engineered sequence

<400> SEQUENCE: 49
atgctgcgta ccatcctggg ttcaaaaatc catcgtgcaa cggtgacgca agttgacctg      60
gactatgtgg ttctgtcac gattacggca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt                  408

<210> SEQ ID NO 50
<211> LENGTH: 136
<212> TYPE: PRT
<213> ORGANISM: Artificial sequence
<220> FEATURE:
<223> OTHER INFORMATION: Engineered sequence

<400> SEQUENCE: 50

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Thr Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
        130                 135

<210> SEQ ID NO 51
<211> LENGTH: 408
<212> TYPE: DNA
<213> ORGANISM: Artificial sequence
<220> FEATURE:
<223> OTHER INFORMATION: Engineered sequence

<400> SEQUENCE: 51

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattgtcca cgtgacggcg acaaccgca tcgttgccct gggcaatgat      360
ctggcggaag ccctgccggg tagcggtctg ctgacgagcc gtagtatt                  408
```

<210> SEQ ID NO 52
<211> LENGTH: 136
<212> TYPE: PRT
<213> ORGANISM: Artificial sequence
<220> FEATURE:
<223> OTHER INFORMATION: Engineered sequence

<400> SEQUENCE: 52

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 53
<211> LENGTH: 408
<212> TYPE: DNA
<213> ORGANISM: Artificial sequence
<220> FEATURE:
<223> OTHER INFORMATION: Engineered sequence

<400> SEQUENCE: 53

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
```

```
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                 408
```

<210> SEQ ID NO 54
<211> LENGTH: 136
<212> TYPE: PRT
<213> ORGANISM: Artificial sequence
<220> FEATURE:
<223> OTHER INFORMATION: Engineered sequence

<400> SEQUENCE: 54

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 55
<211> LENGTH: 408
<212> TYPE: DNA
<213> ORGANISM: Artificial sequence
<220> FEATURE:
<223> OTHER INFORMATION: Engineered sequence

<400> SEQUENCE: 55

```
atgctgcgta ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattataca cgtggatgcg gacaaccgca tcgttgccct gggcaatgat    360
ctggcggaag ccctgccggg tagcggtctg ctgacgagcc gtagtatt                 408
```

<210> SEQ ID NO 56
<211> LENGTH: 136
<212> TYPE: PRT
<213> ORGANISM: Artificial sequence
<220> FEATURE:
<223> OTHER INFORMATION: Engineered sequence

<400> SEQUENCE: 56

```
Met Leu Arg Thr Ile Leu Gly Ser Lys Ile His Arg Ala Thr Val Thr
```

```
                1               5                  10                15
            Gln Val Asp Leu Asp Tyr Val Gly Ser Val Thr Ile Asp Ala Asp Leu
                            20                  25                  30

Val His Ala Ala Gly Leu Ile Glu Gly Glu Lys Val Ala Ile Val Asp
                            35                  40                  45

Ile Thr Asn Gly Ala Arg Leu Glu Thr Tyr Val Ile Val Gly Asp Ala
                        50                  55                  60

Gly Thr Gly Asn Ile Cys Ile Asn Gly Ala Ala His Leu Ile Asn
             65                  70                  75                  80

Pro Gly Asp Leu Val Ile Ile Met Ser Tyr Leu Gln Ala Thr Asp Ala
                                85                  90                  95

Glu Ala Lys Ala Tyr Glu Pro Lys Ile Ile His Val Asp Ala Asp Asn
                            100                 105                 110

Arg Ile Val Ala Leu Gly Asn Asp Leu Ala Glu Ala Leu Pro Gly Ser
                            115                 120                 125

Gly Leu Leu Thr Ser Arg Ser Ile
                        130                 135
```

<210> SEQ ID NO 57
<211> LENGTH: 408
<212> TYPE: DNA
<213> ORGANISM: Artificial sequence
<220> FEATURE:
<223> OTHER INFORMATION: Engineered sequence

<400> SEQUENCE: 57

```
atgctgcgta ccatcctggg ttcaaaaatc catcgtgcaa cggtgacgca agttgacctg     60
gactatgtgg gttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaagctg    300
tacgaaccga aaattataca cgtggatgcg gacaaccgca tcgttgccct gggcaatgat    360
ctggcggaag ccctgccggg tagcggtctg ctgacgagcc gtagtatt               408
```

<210> SEQ ID NO 58
<211> LENGTH: 136
<212> TYPE: PRT
<213> ORGANISM: Artificial sequence
<220> FEATURE:
<223> OTHER INFORMATION: Engineered sequence

<400> SEQUENCE: 58

```
            Met Leu Arg Thr Ile Leu Gly Ser Lys Ile His Arg Ala Thr Val Thr
            1               5                   10                  15

Gln Val Asp Leu Asp Tyr Val Gly Ser Val Thr Ile Asp Ala Asp Leu
                            20                  25                  30

Val His Ala Ala Gly Leu Ile Glu Gly Lys Val Ala Ile Val Asp
                            35                  40                  45

Ile Thr Asn Gly Ala Arg Leu Glu Thr Tyr Val Ile Val Gly Asp Ala
                        50                  55                  60

Gly Thr Gly Asn Ile Cys Ile Asn Gly Ala Ala His Leu Ile Asn
             65                  70                  75                  80

Pro Gly Asp Leu Val Ile Ile Met Ser Tyr Leu Gln Ala Thr Asp Ala
                                85                  90                  95

Glu Ala Lys Leu Tyr Glu Pro Lys Ile Ile His Val Asp Ala Asp Asn
```

```
                100             105             110
Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 59
<211> LENGTH: 408
<212> TYPE: DNA
<213> ORGANISM: Artificial sequence
<220> FEATURE:
<223> OTHER INFORMATION: Engineered sequence

<400> SEQUENCE: 59
atgctgcgta ccatcctggg ttcaaaaatc catcgtgcaa cggtgacgca agttgacctg      60
gactatgtgg gttctgtcac gattacggca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattgtcca cgtgacggcg gacaaccgca tcgttgccct gggcaatgat     360
ctggcggaag ccctgccggg tagcggtctg ctgacgagcc gtagtatt                  408

<210> SEQ ID NO 60
<211> LENGTH: 136
<212> TYPE: PRT
<213> ORGANISM: Artificial sequence
<220> FEATURE:
<223> OTHER INFORMATION: Engineered sequence

<400> SEQUENCE: 60

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Thr Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 61
<211> LENGTH: 408
<212> TYPE: DNA
<213> ORGANISM: Artificial sequence
<220> FEATURE:
<223> OTHER INFORMATION: Engineered sequence

<400> SEQUENCE: 61
```

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300 tacacccccga aaattgtcca cgtggatgcg gacaaccgga tcgttgccct gggcaatgat      360
ctggcggaag ccctgccggg tagcggtctg ctgacgagcc gtagtatt               408
```

<210> SEQ ID NO 62
<211> LENGTH: 136
<212> TYPE: PRT
<213> ORGANISM: Artificial sequence
<220> FEATURE:
<223> OTHER INFORMATION: Engineered sequence

<400> SEQUENCE: 62

Met Leu Arg Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Thr Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 63
<211> LENGTH: 408
<212> TYPE: DNA
<213> ORGANISM: Artificial sequence
<220> FEATURE:
<223> OTHER INFORMATION: Engineered sequence

<400> SEQUENCE: 63

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaagcgt atattgtcca cgtggatgcg gacaaccgga tcgttgccct gggcaatgat      360
ctggcggaag ccctgccggg tagcggtctg ctgacgagcc gtagtatt               408
```

<210> SEQ ID NO 64
<211> LENGTH: 136
<212> TYPE: PRT

<213> ORGANISM: Artificial sequence
<220> FEATURE:
<223> OTHER INFORMATION: Engineered sequence

<400> SEQUENCE: 64

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Ala Tyr Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 65
<211> LENGTH: 408
<212> TYPE: DNA
<213> ORGANISM: Artificial sequence
<220> FEATURE:
<223> OTHER INFORMATION: Engineered sequence

<400> SEQUENCE: 65
atgctgcgta ccatcctggg ttcaaaaatc catcgtgcaa cggtgacgca agttgacctg      60
gactatgtgg ttctgtcac gattacggca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccgt atattgtcca cgtggatgcg gacaaccgga tcgttgccct gggcaatgat    360
ctggcggaag ccctgccggg tagcggtctg ctgacgagcc gtagtatt                 408

<210> SEQ ID NO 66
<211> LENGTH: 136
<212> TYPE: PRT
<213> ORGANISM: Artificial sequence
<220> FEATURE:
<223> OTHER INFORMATION: Engineered sequence

<400> SEQUENCE: 66

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Thr Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Tyr Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 67
<211> LENGTH: 408
<212> TYPE: DNA
<213> ORGANISM: Artificial sequence
<220> FEATURE:
<223> OTHER INFORMATION: Engineered sequence

<400> SEQUENCE: 67
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcacctt taacatttgc atcaatggcg cagctgcgca tctgatcaat    240
ccgggtgatc tggtgattat catgagctat ctgcaggcca cggacgccga agcaaaggct    300
tacaccccga aaattgtcca cgtggatgcg gacaaccgca tcgttgccct gggcaatgat    360
ctggcggaag ccctgccggg tagcggtctg ctgacgagcc gtagtatt                 408

<210> SEQ ID NO 68
<211> LENGTH: 136
<212> TYPE: PRT
<213> ORGANISM: Artificial sequence
<220> FEATURE:
<223> OTHER INFORMATION: Engineered sequence

<400> SEQUENCE: 68

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Phe Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Thr Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 69
<211> LENGTH: 408

<212> TYPE: DNA
<213> ORGANISM: Artificial sequence
<220> FEATURE:
<223> OTHER INFORMATION: Engineered sequence

<400> SEQUENCE: 69

```
atgctgcgta ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccgt atattgtcca cgtggatgcg gacaaccgga tcgttgccct gggcaatgat     360
ctggcggaag ccctgccggg tagcggtctg ctgacgagcc gtagtatt                  408
```

<210> SEQ ID NO 70
<211> LENGTH: 136
<212> TYPE: PRT
<213> ORGANISM: Artificial sequence
<220> FEATURE:
<223> OTHER INFORMATION: Engineered sequence

<400> SEQUENCE: 70

```
Met Leu Arg Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Tyr Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 71
<211> LENGTH: 408
<212> TYPE: DNA
<213> ORGANISM: Artificial sequence
<220> FEATURE:
<223> OTHER INFORMATION: Engineered sequence

<400> SEQUENCE: 71

```
atgctgcgta ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccct taacatttgc atcaatggcg cagctgcgca tctgatcaat     240
ccgggtgatc tggtgattat catgagctat ctgcaggcca cggacgccga agcaaaggct     300
tacgaagcga aaattgtcca cgtggatgcg gacaaccgca tcgttgccct gggcaatgat     360
```
ctggcggaag ccctgccggg tagcggtctg ctgacgagcc gtagtatt        408

<210> SEQ ID NO 72
<211> LENGTH: 136
<212> TYPE: PRT
<213> ORGANISM: Artificial sequence
<220> FEATURE:
<223> OTHER INFORMATION: Engineered sequence

<400> SEQUENCE: 72

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Phe Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Ala Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 73
<211> LENGTH: 408
<212> TYPE: DNA
<213> ORGANISM: Artificial sequence
<220> FEATURE:
<223> OTHER INFORMATION: Engineered sequence

<400> SEQUENCE: 73
atgctgcgta ccatcctggg ttcaaaaatc catcgtgcaa cggtgacgca agttgacctg       60
gactatgtgg ttctgtcac gattgatgca gacctggtcc atgcagcagg tctgatcatt       120
ggtgaaaaag ttgcaattgt cgatatcacc aacggcgctc gtctggaaac gtatgtgatt       180
gttggtgatg cgggcaccgg taacatttgc atcaatggcg cagctgcgca tctgatcaat       240
ccgggtgatc tggtgattat catgagctat ctgcaggcca cggacgccga agcaaaggct       300
tacaccccgt atattgtcca cgtggatgcg gacaaccgga tcgttgccct gggcaatgat       360
ctggcggaag ccctgccggg tagcggtctg ctgacgagcc gtagtatt                   408

<210> SEQ ID NO 74
<211> LENGTH: 136
<212> TYPE: PRT
<213> ORGANISM: Artificial sequence
<220> FEATURE:
<223> OTHER INFORMATION: Engineered sequence

<400> SEQUENCE: 74

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Ile Gly Glu Lys Val Ala Ile Val Asp
         35                  40                  45

Ile Thr Asn Gly Ala Arg Leu Glu Thr Tyr Val Ile Val Gly Asp Ala
         50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Thr Pro Tyr Ile Val His Val Asp Ala Asp Asn
             100                 105                 110

Arg Ile Val Ala Leu Gly Asn Asp Leu Ala Glu Ala Leu Pro Gly Ser
         115                 120                 125

Gly Leu Leu Thr Ser Arg Ser Ile
         130                 135

<210> SEQ ID NO 75
<211> LENGTH: 408
<212> TYPE: DNA
<213> ORGANISM: Artificial sequence
<220> FEATURE:
<223> OTHER INFORMATION: Engineered sequence

<400> SEQUENCE: 75
atgctgcgta ccatcctggg ttcaaaaatc catcgtgcaa cggtgacgca agttgacctg      60
gactatgtgg ttctgtcac gattgatgca gacctggtcc atgcagcagg tctgatcatt     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaagcga aaattgtcca cgtggatgcg acaaccgga tcgttgccct gggcaatgat     360
ctggcggaag ccctgccggg tagcggtctg ctgacgagcc gtagtatt                  408

<210> SEQ ID NO 76
<211> LENGTH: 136
<212> TYPE: PRT
<213> ORGANISM: Artificial sequence
<220> FEATURE:
<223> OTHER INFORMATION: Engineered sequence

<400> SEQUENCE: 76

Met Leu Arg Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
             20                  25                  30

Val His Ala Ala Gly Leu Ile Ile Gly Glu Lys Val Ala Ile Val Asp
         35                  40                  45

Ile Thr Asn Gly Ala Arg Leu Glu Thr Tyr Val Ile Val Gly Asp Ala
         50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Ala Lys Ile Val His Val Asp Ala Asp Asn
             100                 105                 110

Arg Ile Val Ala Leu Gly Asn Asp Leu Ala Glu Ala Leu Pro Gly Ser
         115                 120                 125

Gly Leu Leu Thr Ser Arg Ser Ile
    130                 135

<210> SEQ ID NO 77
<211> LENGTH: 408
<212> TYPE: DNA
<213> ORGANISM: Artificial sequence
<220> FEATURE:
<223> OTHER INFORMATION: Engineered sequence

<400> SEQUENCE: 77
atgttccgta ccatcctggg ttcaaaaatc catcgtgcaa cggtgacgca agttgacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtagtatt                  408

<210> SEQ ID NO 78
<211> LENGTH: 136
<212> TYPE: PRT
<213> ORGANISM: Artificial sequence
<220> FEATURE:
<223> OTHER INFORMATION: Engineered sequence

<400> SEQUENCE: 78

Met Phe Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 79
<211> LENGTH: 408
<212> TYPE: DNA
<213> ORGANISM: Artificial sequence
<220> FEATURE:
<223> OTHER INFORMATION: Engineered sequence

<400> SEQUENCE: 79
atgagtcgta ccatcctggg ttcaaaaatc catcgtgcaa cggtgacgca agttgacctg      60
gactatgtgg gttctgtcac cattgatgca gacctggtcc atgcagcagg tctgatcgaa     120

```
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccctgccggg tagcggtctg ctgacgagcc gtagtatt                   408
```

<210> SEQ ID NO 80
<211> LENGTH: 136
<212> TYPE: PRT
<213> ORGANISM: Artificial sequence
<220> FEATURE:
<223> OTHER INFORMATION: Engineered sequence

<400> SEQUENCE: 80

```
Met Ser Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 81
<211> LENGTH: 408
<212> TYPE: DNA
<213> ORGANISM: Artificial sequence
<220> FEATURE:
<223> OTHER INFORMATION: Engineered sequence

<400> SEQUENCE: 81

```
atgctgcgtt caatcctggg ttcaaaaatc catcgtgcaa cggtgacgca agttgacctg       60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccctgccggg tagcggtctg ctgacgagcc gtagtatt                   408
```

<210> SEQ ID NO 82
<211> LENGTH: 136
<212> TYPE: PRT
<213> ORGANISM: Artificial sequence
<220> FEATURE:
<223> OTHER INFORMATION: Engineered sequence

<400> SEQUENCE: 82

Met Leu Arg Ser Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 83
<211> LENGTH: 408
<212> TYPE: DNA
<213> ORGANISM: Artificial sequence
<220> FEATURE:
<223> OTHER INFORMATION: Engineered sequence

<400> SEQUENCE: 83
atgctgcgta ccatcatggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg gacaaccgca tcgttgccct gggcaatgat   360
ctggcggaag ccctgccggg tagcggtctg ctgacgagcc gtagtatt              408

<210> SEQ ID NO 84
<211> LENGTH: 136
<212> TYPE: PRT
<213> ORGANISM: Artificial sequence
<220> FEATURE:
<223> OTHER INFORMATION: Engineered sequence

<400> SEQUENCE: 84

Met Leu Arg Thr Ile Met Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala

```
                            85                  90                  95
Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 85
<211> LENGTH: 408
<212> TYPE: DNA
<213> ORGANISM: Artificial sequence
<220> FEATURE:
<223> OTHER INFORMATION: Engineered sequence

<400> SEQUENCE: 85
atgctgcgta ccatcctggg tggaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat      360
ctggcggaag ccctgccggg tagcggtctg ctgacgagcc gtagtatt                  408

<210> SEQ ID NO 86
<211> LENGTH: 136
<212> TYPE: PRT
<213> ORGANISM: Artificial sequence
<220> FEATURE:
<223> OTHER INFORMATION: Engineered sequence

<400> SEQUENCE: 86

Met Leu Arg Thr Ile Leu Gly Gly Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 87
<211> LENGTH: 408
<212> TYPE: DNA
<213> ORGANISM: Artificial sequence
<220> FEATURE:
<223> OTHER INFORMATION: Engineered sequence
```

<400> SEQUENCE: 87

```
atgctgcgta ccatcctggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg gacaaccgct cggttgccct gggcaatgat   360
ctggcggaag ccctgccggg tagcggtctg ctgacgagcc gtagtatt               408
```

<210> SEQ ID NO 88
<211> LENGTH: 136
<212> TYPE: PRT
<213> ORGANISM: Artificial sequence
<220> FEATURE:
<223> OTHER INFORMATION: Engineered sequence

<400> SEQUENCE: 88

```
Met Leu Arg Thr Ile Leu Gly Ser Lys Ile His Arg Ala Thr Val Thr
  1               5                  10                  15
Gln Val Asp Leu Asp Tyr Val Gly Ser Val Thr Ile Asp Ala Asp Leu
                 20                  25                  30
Val His Ala Ala Gly Leu Ile Glu Gly Glu Lys Val Ala Ile Val Asp
             35                  40                  45
Ile Thr Asn Gly Ala Arg Leu Glu Thr Tyr Val Ile Val Gly Asp Ala
         50                  55                  60
Gly Thr Gly Asn Ile Cys Ile Asn Gly Ala Ala Ala His Leu Ile Asn
 65                  70                  75                  80
Pro Gly Asp Leu Val Ile Ile Met Ser Tyr Leu Gln Ala Thr Asp Ala
                 85                  90                  95
Glu Ala Lys Ala Tyr Glu Pro Lys Ile Val His Val Asp Ala Asp Asn
            100                 105                 110
Arg Ser Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 89
<211> LENGTH: 408
<212> TYPE: DNA
<213> ORGANISM: Artificial sequence
<220> FEATURE:
<223> OTHER INFORMATION: Engineered sequence

<400> SEQUENCE: 89

```
atgctgcgta ccatcctggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg gacaaccgca tctgtgccct gggcaatgat   360
ctggcggaag ccctgccggg tagcggtctg ctgacgagcc gtagtatt               408
```

```
<210> SEQ ID NO 90
<211> LENGTH: 136
<212> TYPE: PRT
<213> ORGANISM: Artificial sequence
<220> FEATURE:
<223> OTHER INFORMATION: Engineered sequence

<400> SEQUENCE: 90

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Cys Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 91
<211> LENGTH: 408
<212> TYPE: DNA
<213> ORGANISM: Artificial sequence
<220> FEATURE:
<223> OTHER INFORMATION: Engineered sequence

<400> SEQUENCE: 91
atgctgcgta ccatcctggg ttcaaaaatc catcgtgcaa cggtgacgca agttgacctg     60
gactatgtgg ttctgtcac cattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgcc tgttgccct gggcaatgat     360 ctggcggaag ccctgccggg tagcggtctg ctgacgagcc gtagtatt                408

<210> SEQ ID NO 92
<211> LENGTH: 136
<212> TYPE: PRT
<213> ORGANISM: Artificial sequence
<220> FEATURE:
<223> OTHER INFORMATION: Engineered sequence

<400> SEQUENCE: 92

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45
```

```
Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Pro Val Ala Leu Gly Asn Asp Leu Ala Glu Ala Leu Pro Gly Ser
            115                 120                 125

Gly Leu Leu Thr Ser Arg Ser Ile
    130                 135
```

<210> SEQ ID NO 93
<211> LENGTH: 408
<212> TYPE: DNA
<213> ORGANISM: Artificial sequence
<220> FEATURE:
<223> OTHER INFORMATION: Engineered sequence

<400> SEQUENCE: 93

```
atgctgcgta ccatcctggg ttcaaaaatc catcgtgcaa cggtgacgca agttgacctg     60
gactatgtgg gttctgtcac cattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca atgttgccct gggcaatgat    360
ctggcggaag ccctgccggg tagcggtctg ctgacgagcc gtagtatt              408
```

<210> SEQ ID NO 94
<211> LENGTH: 136
<212> TYPE: PRT
<213> ORGANISM: Artificial sequence
<220> FEATURE:
<223> OTHER INFORMATION: Engineered sequence

<400> SEQUENCE: 94

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
                20                  25                  30

Val His Ala Ala Gly Leu Ile Glu Gly Lys Val Ala Ile Val Asp
            35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Asn Val Ala Leu Gly Asn Asp Leu Ala Glu Ala Leu Pro Gly Ser
            115                 120                 125

Gly Leu Leu Thr Ser Arg Ser Ile
    130                 135
```

<210> SEQ ID NO 95
<211> LENGTH: 408
<212> TYPE: DNA
<213> ORGANISM: Artificial sequence
<220> FEATURE:
<223> OTHER INFORMATION: Engineered sequence

<400> SEQUENCE: 95

```
atgctgcgta ccatcctggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggct   300
tacgaaccga aaattgtcca cgtggatgcg gacaaccgct gggttgccct gggcaatgat   360
ctggcggaag ccctgccggg tagcggtctg ctgacgagcc gtagtatt              408
```

<210> SEQ ID NO 96
<211> LENGTH: 136
<212> TYPE: PRT
<213> ORGANISM: Artificial sequence
<220> FEATURE:
<223> OTHER INFORMATION: Engineered sequence

<400> SEQUENCE: 96

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Trp Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 97
<211> LENGTH: 408
<212> TYPE: DNA
<213> ORGANISM: Artificial sequence
<220> FEATURE:
<223> OTHER INFORMATION: Engineered sequence

<400> SEQUENCE: 97

```
atgctgcgta ccatcctggg ttcaaaaatc catcgtgcaa cggtgacgca agttgacctg    60
gactatgtgg gttctgtcac cattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
```

```
ccgggtgatc tggtgattat catgagctat ctgcaggcca cggacgccga agcaaatgct    300
tacgaaccga aaattgtcca cgtggatgcg gacaaccgca atgttgccct gggcaatgat    360
ctggcggaag ccctgccggg tagcggtctg ctgacgagcc gtagtatt                 408
```

<210> SEQ ID NO 98
<211> LENGTH: 136
<212> TYPE: PRT
<213> ORGANISM: Artificial sequence
<220> FEATURE:
<223> OTHER INFORMATION: Engineered sequence

<400> SEQUENCE: 98

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Asn Ala Tyr Glu Pro Lys Ile Val His Val Asp Ala Asp Asn
            100                 105                 110

Arg Asn Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 99
<211> LENGTH: 408
<212> TYPE: DNA
<213> ORGANISM: Artificial sequence
<220> FEATURE:
<223> OTHER INFORMATION: Engineered sequence

<400> SEQUENCE: 99

```
atgctgcgta ccatcctggg ttcaaaaatc catcgtgcaa cggtgacgca agttgacctg    60
gactatgtgg ttctgtcac cattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttaatct gggcaatgat    360
ctggcggaag ccctgccggg tagcggtctg ctgacgagcc gtagtatt                 408
```

<210> SEQ ID NO 100
<211> LENGTH: 136
<212> TYPE: PRT
<213> ORGANISM: Artificial sequence
<220> FEATURE:
<223> OTHER INFORMATION: Engineered sequence

<400> SEQUENCE: 100

```
Met Leu Arg Thr Ile Leu Gly Ser Lys Ile His Arg Ala Thr Val Thr
1               5                   10                  15
```

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Asn Leu Gly Asn Asp Leu Ala Glu Ala Leu Pro Gly Ser
        115                 120                 125

Gly Leu Leu Thr Ser Arg Ser Ile
    130                 135

<210> SEQ ID NO 101
<211> LENGTH: 408
<212> TYPE: DNA
<213> ORGANISM: Artificial sequence
<220> FEATURE:
<223> OTHER INFORMATION: Engineered sequence

<400> SEQUENCE: 101
atgctgcgta ccatcctggg ttcaaaaatc catcgtgcaa cggtgacgca agttgacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccta tggcaatgat     360
ctggcggaag ccctgccggg tagcggtctg ctgacgagcc gtagtatt                  408

<210> SEQ ID NO 102
<211> LENGTH: 136
<212> TYPE: PRT
<213> ORGANISM: Artificial sequence
<220> FEATURE:
<223> OTHER INFORMATION: Engineered sequence

<400> SEQUENCE: 102

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Tyr Gly Asn Asp Leu Ala Glu Ala Leu Pro Gly Ser
            115                 120                 125

Gly Leu Leu Thr Ser Arg Ser Ile
    130                 135

<210> SEQ ID NO 103
<211> LENGTH: 408
<212> TYPE: DNA
<213> ORGANISM: Artificial sequence
<220> FEATURE:
<223> OTHER INFORMATION: Engineered sequence

<400> SEQUENCE: 103
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgcctt tggcaatgat     360
ctggcggaag ccctgccggg tagcggtctg ctgacgagcc gtagtatt                 408

<210> SEQ ID NO 104
<211> LENGTH: 136
<212> TYPE: PRT
<213> ORGANISM: Artificial sequence
<220> FEATURE:
<223> OTHER INFORMATION: Engineered sequence

<400> SEQUENCE: 104

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Phe Gly Asn Asp Leu Ala Glu Ala Leu Pro Gly Ser
            115                 120                 125

Gly Leu Leu Thr Ser Arg Ser Ile
    130                 135

<210> SEQ ID NO 105
<211> LENGTH: 408
<212> TYPE: DNA
<213> ORGANISM: Artificial sequence
<220> FEATURE:
<223> OTHER INFORMATION: Engineered sequence

<400> SEQUENCE: 105
atgctgcgta ccatcctggg ttcaaaaatc catcgtgcaa cggtgacgca agttgacctg      60

```
gactatgtgg gttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggccctgat      360
ctggcggaag ccctgccggg tagcggtctg ctgacgagcc gtagtatt                  408
```

<210> SEQ ID NO 106
<211> LENGTH: 136
<212> TYPE: PRT
<213> ORGANISM: Artificial sequence
<220> FEATURE:
<223> OTHER INFORMATION: Engineered sequence

<400> SEQUENCE: 106

```
Met Leu Arg Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Pro Asp Leu Ala Glu Ala Leu Pro Gly Ser
        115                 120                 125

Gly Leu Leu Thr Ser Arg Ser Ile
    130                 135
```

<210> SEQ ID NO 107
<211> LENGTH: 408
<212> TYPE: DNA
<213> ORGANISM: Artificial sequence
<220> FEATURE:
<223> OTHER INFORMATION: Engineered sequence

<400> SEQUENCE: 107

```
atgctgcgta ccatcctggg ttcaaaaatc catcgtgcaa cggtgacgca agttgacctg       60
gactatgtgg gttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcgctgat      360
ctggcggaag ccctgccggg tagcggtctg ctgacgagcc gtagtatt                  408
```

<210> SEQ ID NO 108
<211> LENGTH: 136
<212> TYPE: PRT
<213> ORGANISM: Artificial sequence

```
<220> FEATURE:
<223> OTHER INFORMATION: Engineered sequence

<400> SEQUENCE: 108

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Ala Asp Leu Ala Glu Ala Leu Pro Gly Ser
        115                 120                 125

Gly Leu Leu Thr Ser Arg Ser Ile
    130                 135

<210> SEQ ID NO 109
<211> LENGTH: 408
<212> TYPE: DNA
<213> ORGANISM: Artificial sequence
<220> FEATURE:
<223> OTHER INFORMATION: Engineered sequence

<400> SEQUENCE: 109
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca gtggatgcg acaaccgca tcgttgccct gggcgttgat      360
ctggcggaag ccctgccggg tagcggtctg ctgacgagcc gtagtatt                  408

<210> SEQ ID NO 110
<211> LENGTH: 136
<212> TYPE: PRT
<213> ORGANISM: Artificial sequence
<220> FEATURE:
<223> OTHER INFORMATION: Engineered sequence

<400> SEQUENCE: 110

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
```

```
            65                  70                  75                  80
Pro Gly Asp Leu Val Ile Ile Met Ser Tyr Leu Gln Ala Thr Asp Ala
                    85                  90                  95

Glu Ala Lys Ala Tyr Glu Pro Lys Ile Val His Val Asp Ala Asp Asn
                    100                 105                 110

Arg Ile Val Ala Leu Gly Val Asp Leu Ala Glu Ala Leu Pro Gly Ser
                    115                 120                 125

Gly Leu Leu Thr Ser Arg Ser Ile
                    130                 135
```

<210> SEQ ID NO 111
<211> LENGTH: 408
<212> TYPE: DNA
<213> ORGANISM: Artificial sequence
<220> FEATURE:
<223> OTHER INFORMATION: Engineered sequence

<400> SEQUENCE: 111

```
atgctgcgta ccatcctggg ttcaaaaatc catcgtgcaa cggtgacgca agttgacctg    60
gactatgtgg ttctgtcac cattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttgccct gggcaatgat    360
ggtgcggaag ccctgccggg tagcggtctg ctgacgagcc gtagtatt             408
```

<210> SEQ ID NO 112
<211> LENGTH: 136
<212> TYPE: PRT
<213> ORGANISM: Artificial sequence
<220> FEATURE:
<223> OTHER INFORMATION: Engineered sequence

<400> SEQUENCE: 112

```
Met Leu Arg Thr Ile Leu Gly Ser Lys Ile His Arg Ala Thr Val Thr
1                   5                   10                  15

Gln Val Asp Leu Asp Tyr Val Gly Ser Val Thr Ile Asp Ala Asp Leu
                    20                  25                  30

Val His Ala Ala Gly Leu Ile Glu Gly Lys Val Ala Ile Val Asp
                    35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                    85                  90                  95

Glu Ala Lys Ala Tyr Glu Pro Lys Ile Val His Val Asp Ala Asp Asn
                    100                 105                 110

Arg Ile Val Ala Leu Gly Asn Asp Gly Ala Glu Ala Leu Pro Gly Ser
                    115                 120                 125

Gly Leu Leu Thr Ser Arg Ser Ile
                    130                 135
```

<210> SEQ ID NO 113
<211> LENGTH: 408
<212> TYPE: DNA

<213> ORGANISM: Artificial sequence
<220> FEATURE:
<223> OTHER INFORMATION: Engineered sequence

<400> SEQUENCE: 113

| | |
|---|---|
| atgctgcgta ccatcctggg ttcaaaaatc catcgtgcaa cggtgacgca agttgacctg | 60 |
| gactatgtgg gttctgtcac cattgatgca gacctggtcc atgcagcagg tctgatcgaa | 120 |
| ggtgaaaaag ttgcaattgt cgatatcacc aacggcgctc gtctggaaac gtatgtgatt | 180 |
| gttggtgatg cgggcaccgg taacatttgc atcaatggcg cagctgcgca tctgatcaat | 240 |
| ccgggtgatc tggtgattat catgagctat ctgcaggcca cggacgccga agcaaaggct | 300 |
| tacgaaccga aaattgtcca cgtggatgcg gacaaccgca tcgttgccct gggcaatgat | 360 |
| tctgcggaag ccctgccggg tagcggtctg ctgacgagcc gtagtatt | 408 |

<210> SEQ ID NO 114
<211> LENGTH: 136
<212> TYPE: PRT
<213> ORGANISM: Artificial sequence
<220> FEATURE:
<223> OTHER INFORMATION: Engineered sequence

<400> SEQUENCE: 114

Met Leu Arg Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly Asn Asp Ser Ala Glu Ala Leu Pro Gly Ser
        115                 120                 125
Gly Leu Leu Thr Ser Arg Ser Ile
    130                 135

<210> SEQ ID NO 115
<211> LENGTH: 408
<212> TYPE: DNA
<213> ORGANISM: Artificial sequence
<220> FEATURE:
<223> OTHER INFORMATION: Engineered sequence

<400> SEQUENCE: 115

| | |
|---|---|
| atgctgcgta ccatcctggg ttcaaaaatc catcgtgcaa cggtgacgca agttgacctg | 60 |
| gactatgtgg gttctgtcac cattgatgca gacctggtcc atgcagcagg tctgatcgaa | 120 |
| ggtgaaaaag ttgcaattgt cgatatcacc aacggcgctc gtctggaaac gtatgtgatt | 180 |
| gttggtgatg cgggcaccgg taacatttgc atcaatggcg cagctgcgca tctgatcaat | 240 |
| ccgggtgatc tggtgattat catgagctat ctgcaggcca cggacgccga agcaaaggct | 300 |
| tacgaaccga aaattgtcca cgtggatgcg gacaaccgca tcgttgccct gggcaatgat | 360 |

```
actgcggaag ccctgccggg tagcggtctg ctgacgagcc gtagtatt                 408
```

<210> SEQ ID NO 116
<211> LENGTH: 136
<212> TYPE: PRT
<213> ORGANISM: Artificial sequence
<220> FEATURE:
<223> OTHER INFORMATION: Engineered sequence

<400> SEQUENCE: 116

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Thr Ala Glu Ala Leu Pro Gly Ser
        115                 120                 125

Gly Leu Leu Thr Ser Arg Ser Ile
    130                 135
```

<210> SEQ ID NO 117
<211> LENGTH: 408
<212> TYPE: DNA
<213> ORGANISM: Artificial sequence
<220> FEATURE:
<223> OTHER INFORMATION: Engineered sequence

<400> SEQUENCE: 117

```
atgctgcgta ccatcctggg ttcaaaaatc catcgtgcaa cggtgacgca agttgacctg     60
gactatgtgg ttctgtcac cattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttgccct gggcaatgat    360
ctggcggaag atctgccggg tagcggtctg ctgacgagcc gtagtatt                 408
```

<210> SEQ ID NO 118
<211> LENGTH: 136
<212> TYPE: PRT
<213> ORGANISM: Artificial sequence
<220> FEATURE:
<223> OTHER INFORMATION: Engineered sequence

<400> SEQUENCE: 118

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30
```

Val His Ala Ala Gly Leu Ile Glu Gly Glu Lys Val Ala Ile Val Asp
     35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Asp Leu Pro Gly Ser
        115                 120                 125

Gly Leu Leu Thr Ser Arg Ser Ile
    130                 135

<210> SEQ ID NO 119
<211> LENGTH: 408
<212> TYPE: DNA
<213> ORGANISM: Artificial sequence
<220> FEATURE:
<223> OTHER INFORMATION: Engineered sequence

<400> SEQUENCE: 119
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttgccct gggcaatgat    360
ctggcggaag tctgccggg tagcggtctg ctgacgagcc gtagtatt                  408

<210> SEQ ID NO 120
<211> LENGTH: 136
<212> TYPE: PRT
<213> ORGANISM: Artificial sequence
<220> FEATURE:
<223> OTHER INFORMATION: Engineered sequence

<400> SEQUENCE: 120

Met Leu Arg Thr Ile Leu Gly Ser Lys Ile His Arg Ala Thr Val Thr
1                5                  10                  15

Gln Val Asp Leu Asp Tyr Val Gly Ser Val Thr Ile Asp Ala Asp Leu
                20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Gly Leu Pro Gly Ser
        115                 120                 125

Gly Leu Leu Thr Ser Arg Ser Ile
    130             135

<210> SEQ ID NO 121
<211> LENGTH: 408
<212> TYPE: DNA
<213> ORGANISM: Artificial sequence
<220> FEATURE:
<223> OTHER INFORMATION: Engineered sequence

<400> SEQUENCE: 121

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaac atctgccggg tagcggtctg ctgacgagcc gtagtatt               408
```

<210> SEQ ID NO 122
<211> LENGTH: 136
<212> TYPE: PRT
<213> ORGANISM: Artificial sequence
<220> FEATURE:
<223> OTHER INFORMATION: Engineered sequence

<400> SEQUENCE: 122

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu His Leu Pro Gly Ser
        115                 120                 125

Gly Leu Leu Thr Ser Arg Ser Ile
    130             135

<210> SEQ ID NO 123
<211> LENGTH: 408
<212> TYPE: DNA
<213> ORGANISM: Artificial sequence
<220> FEATURE:
<223> OTHER INFORMATION: Engineered sequence

<400> SEQUENCE: 123

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa     120
ggtgaaaaag ttgcaattgt cgatatcacc aacggcgctc gtctggaaac gtatgtgatt     180
```

```
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccgtccgggt tagcggtctg ctgacgagcc gtagtatt                   408
```

<210> SEQ ID NO 124
<211> LENGTH: 136
<212> TYPE: PRT
<213> ORGANISM: Artificial sequence
<220> FEATURE:
<223> OTHER INFORMATION: Engineered sequence

<400> SEQUENCE: 124

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Gly Pro Gly Ser
        115                 120                 125

Gly Leu Leu Thr Ser Arg Ser Ile
    130                 135
```

<210> SEQ ID NO 125
<211> LENGTH: 408
<212> TYPE: DNA
<213> ORGANISM: Artificial sequence
<220> FEATURE:
<223> OTHER INFORMATION: Engineered sequence

<400> SEQUENCE: 125

```
atgctgcgta ccatcctggg ttcaaaaatc catcgtgcaa cggtgacgca agttgacctg       60
gactatgtgg gttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccgatccggg tagcggtctg ctgacgagcc gtagtatt                   408
```

<210> SEQ ID NO 126
<211> LENGTH: 136
<212> TYPE: PRT
<213> ORGANISM: Artificial sequence
<220> FEATURE:
<223> OTHER INFORMATION: Engineered sequence

<400> SEQUENCE: 126

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Asp Pro Gly Ser
        115                 120                 125

Gly Leu Leu Thr Ser Arg Ser Ile
    130                 135

<210> SEQ ID NO 127
<211> LENGTH: 408
<212> TYPE: DNA
<213> ORGANISM: Artificial sequence
<220> FEATURE:
<223> OTHER INFORMATION: Engineered sequence

<400> SEQUENCE: 127
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat      360
ctggcggaag ccctgccgga gagcggtctg ctgacgagcc gtagtatt                   408

<210> SEQ ID NO 128
<211> LENGTH: 136
<212> TYPE: PRT
<213> ORGANISM: Artificial sequence
<220> FEATURE:
<223> OTHER INFORMATION: Engineered sequence

<400> SEQUENCE: 128

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

```
Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Glu Ser
            115                 120                 125

Gly Leu Leu Thr Ser Arg Ser Ile
        130                 135

<210> SEQ ID NO 129
<211> LENGTH: 408
<212> TYPE: DNA
<213> ORGANISM: Artificial sequence
<220> FEATURE:
<223> OTHER INFORMATION: Engineered sequence

<400> SEQUENCE: 129
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat     360
ctggcggaag ccctgccgcg gagcggtctg ctgacgagcc gtagtatt               408

<210> SEQ ID NO 130
<211> LENGTH: 136
<212> TYPE: PRT
<213> ORGANISM: Artificial sequence
<220> FEATURE:
<223> OTHER INFORMATION: Engineered sequence

<400> SEQUENCE: 130

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Arg Ser
            115                 120                 125

Gly Leu Leu Thr Ser Arg Ser Ile
        130                 135

<210> SEQ ID NO 131
<211> LENGTH: 408
<212> TYPE: DNA
<213> ORGANISM: Artificial sequence
<220> FEATURE:
<223> OTHER INFORMATION: Engineered sequence
```

<400> SEQUENCE: 131

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccctgccggg tagcggtatt ctgacgagcc gtagtatt               408
```

<210> SEQ ID NO 132
<211> LENGTH: 136
<212> TYPE: PRT
<213> ORGANISM: Artificial sequence
<220> FEATURE:
<223> OTHER INFORMATION: Engineered sequence

<400> SEQUENCE: 132

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Ile Leu Thr Ser Arg Ser Ile
    130                 135
```

<210> SEQ ID NO 133
<211> LENGTH: 408
<212> TYPE: DNA
<213> ORGANISM: Artificial sequence
<220> FEATURE:
<223> OTHER INFORMATION: Engineered sequence

<400> SEQUENCE: 133

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggct      300
tacgaaccga aaattgtcca cgtggatgcg gacaaccgca tcgttgccct gggcaatgat      360
ctggcggaag ccctgccggg tagcggtctg ctgacgacgc gtagtatt               408
```

<210> SEQ ID NO 134

<211> LENGTH: 136
<212> TYPE: PRT
<213> ORGANISM: Artificial sequence
<220> FEATURE:
<223> OTHER INFORMATION: Engineered sequence

<400> SEQUENCE: 134

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Thr Arg Ser Ile
    130                 135

<210> SEQ ID NO 135
<211> LENGTH: 408
<212> TYPE: DNA
<213> ORGANISM: Artificial sequence
<220> FEATURE:
<223> OTHER INFORMATION: Engineered sequence

<400> SEQUENCE: 135
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacggatc gtagtatt                  408

<210> SEQ ID NO 136
<211> LENGTH: 136
<212> TYPE: PRT
<213> ORGANISM: Artificial sequence
<220> FEATURE:
<223> OTHER INFORMATION: Engineered sequence

<400> SEQUENCE: 136

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala

```
                50                  55                  60
Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Asp Arg Ser Ile
            130                 135

<210> SEQ ID NO 137
<211> LENGTH: 408
<212> TYPE: DNA
<213> ORGANISM: Artificial sequence
<220> FEATURE:
<223> OTHER INFORMATION: Engineered sequence

<400> SEQUENCE: 137
atgctgcgta ccatcctggg ttcaaaaatc catcgtgcaa cggtgacgca agttgacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg ctgacgagcc gtaatatt                  408

<210> SEQ ID NO 138
<211> LENGTH: 136
<212> TYPE: PRT
<213> ORGANISM: Artificial sequence
<220> FEATURE:
<223> OTHER INFORMATION: Engineered sequence

<400> SEQUENCE: 138

Met Leu Arg Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
                 20                  25                  30

Val His Ala Ala Gly Leu Ile Glu Gly Glu Lys Val Ala Ile Val Asp
             35                  40                  45

Ile Thr Asn Gly Ala Arg Leu Glu Thr Tyr Val Ile Val Gly Asp Ala
         50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Asn Ile
            130                 135
```

<210> SEQ ID NO 139
<211> LENGTH: 408
<212> TYPE: DNA
<213> ORGANISM: Artificial sequence
<220> FEATURE:
<223> OTHER INFORMATION: Engineered sequence

<400> SEQUENCE: 139

```
atgctgcgta ccatcctggg ttcaaaaatc catcgtgcaa cggtgacgca agttgacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg acaaccgca tcgttgccct gggcaatgat     360
ctggcggaag ccctgccggg tagcggtctg ctgacgagcc gtagtgag                  408
```

<210> SEQ ID NO 140
<211> LENGTH: 136
<212> TYPE: PRT
<213> ORGANISM: Artificial sequence
<220> FEATURE:
<223> OTHER INFORMATION: Engineered sequence

<400> SEQUENCE: 140

```
Met Leu Arg Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Glu
    130                 135
```

<210> SEQ ID NO 141
<211> LENGTH: 408
<212> TYPE: DNA
<213> ORGANISM: Artificial sequence
<220> FEATURE:
<223> OTHER INFORMATION: Engineered sequence

<400> SEQUENCE: 141

```
atgctgcgta ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
```

```
tacgaaccgt atattataca cgtgacggcg gacaaccgca tcgttgccct gggcaatgat        360
ctggcggaag ccctgccggg tagcggtctg ctgacgagcc gtagtatt                    408
```

<210> SEQ ID NO 142
<211> LENGTH: 136
<212> TYPE: PRT
<213> ORGANISM: Artificial sequence
<220> FEATURE:
<223> OTHER INFORMATION: Engineered sequence

<400> SEQUENCE: 142

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Tyr Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 143
<211> LENGTH: 408
<212> TYPE: DNA
<213> ORGANISM: Artificial sequence
<220> FEATURE:
<223> OTHER INFORMATION: Engineered sequence

<400> SEQUENCE: 143

```
atgctgcgta ccatcctggg ttcaaaaatc catcgtgcaa cggtgacgca agttgacctg        60
cattatgtgg gttctgtcac gattgatgca gacctggtcc atgcagcagg tctgatcgaa       120
ggtgaaaaag ttgcaattgt cgatatcacc aacggcgctc gtctggaaac gtatgtgatt       180
gttggtgatg cgggcaccgg taacatttgc atcaatggcg cagctgcgca tctgatcaat       240
ccgggtgatc tggtgattat catgagctat ctgcaggcca cggacgccga agcaaaggca       300
tacgaaccga aaattataca cgtgacggcg gacaaccgca tcgttgccct gggcaatgat       360
ctggcggaag ccctgccggg tagcggtctg ctgacgagcc gtagtatt                    408
```

<210> SEQ ID NO 144
<211> LENGTH: 136
<212> TYPE: PRT
<213> ORGANISM: Artificial sequence
<220> FEATURE:
<223> OTHER INFORMATION: Engineered sequence

<400> SEQUENCE: 144

```
Met Leu Arg Thr Ile Leu Gly Ser Lys Ile His Arg Ala Thr Val Thr
1               5                   10                  15
```

Gln Val Asp Leu His Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
        130                 135

<210> SEQ ID NO 145
<211> LENGTH: 408
<212> TYPE: DNA
<213> ORGANISM: Artificial sequence
<220> FEATURE:
<223> OTHER INFORMATION: Engineered sequence

<400> SEQUENCE: 145
atgctgcgta ccatcctggg ttcaaaaatc catcgtgcaa cggtgacgca agttgacctg      60
cattatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccgt atattataca cgtgacggcg gacaaccgca tcgttgccct gggcaatgat     360
ctggcggaag ccctgccggg tagcggtctg ctgacgagcc gtagtatt               408

<210> SEQ ID NO 146
<211> LENGTH: 136
<212> TYPE: PRT
<213> ORGANISM: Artificial sequence
<220> FEATURE:
<223> OTHER INFORMATION: Engineered sequence

<400> SEQUENCE: 146

Met Leu Arg Thr Ile Leu Gly Ser Lys Ile His Arg Ala Thr Val Thr
1               5                   10                  15

Gln Val Asp Leu His Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Tyr Ile Ile His Val Thr Ala Asp Asn
            100                 105                 110

```
Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 147
<211> LENGTH: 408
<212> TYPE: DNA
<213> ORGANISM: Artificial sequence
<220> FEATURE:
<223> OTHER INFORMATION: Engineered sequence

<400> SEQUENCE: 147

```
atgctgcgta ccatcctggg ttcaaaaatc catcgtgcaa cggtgacgca agttgacctg      60
cattatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaagcga aaattataca cgtgacggcg gacaaccgca tcgttgccct gggcaatgat     360
ctggcggaag ccctgccggg tagcggtctg ctgacgagcc gtagtatt                408
```

<210> SEQ ID NO 148
<211> LENGTH: 136
<212> TYPE: PRT
<213> ORGANISM: Artificial sequence
<220> FEATURE:
<223> OTHER INFORMATION: Engineered sequence

<400> SEQUENCE: 148

```
Met Leu Arg Thr Ile Leu Gly Ser Lys Ile His Arg Ala Thr Val Thr
1               5                   10                  15

Gln Val Asp Leu His Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Ala Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 149
<211> LENGTH: 408
<212> TYPE: DNA
<213> ORGANISM: Artificial sequence
<220> FEATURE:
<223> OTHER INFORMATION: Engineered sequence

<400> SEQUENCE: 149

```
atgctgcgta ccatcctggg ttcaaaaatc catcgtgcaa cggtgacgca agttgacctg      60
```

-continued

```
gactatgtgg gttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccgatccgcg tagcggtctg ctgacgcatc gtagtatt                 408
```

<210> SEQ ID NO 150
<211> LENGTH: 136
<212> TYPE: PRT
<213> ORGANISM: Artificial sequence
<220> FEATURE:
<223> OTHER INFORMATION: Engineered sequence

<400> SEQUENCE: 150

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Asp Pro Arg Ser
        115                 120                 125

Gly Leu Leu Thr His Arg Ser Ile
    130                 135
```

<210> SEQ ID NO 151
<211> LENGTH: 408
<212> TYPE: DNA
<213> ORGANISM: Artificial sequence
<220> FEATURE:
<223> OTHER INFORMATION: Engineered sequence

<400> SEQUENCE: 151

```
atgctgtaca ccatcctggg ttcaaaaatc catcgtgcaa cggtgacgca agttgacctg     60
gactatgtgg gttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                 408
```

<210> SEQ ID NO 152
<211> LENGTH: 136
<212> TYPE: PRT
<213> ORGANISM: Artificial sequence
<220> FEATURE:

-continued

<223> OTHER INFORMATION: Engineered sequence

<400> SEQUENCE: 152

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 153
<211> LENGTH: 408
<212> TYPE: DNA
<213> ORGANISM: Artificial sequence
<220> FEATURE:
<223> OTHER INFORMATION: Engineered sequence

<400> SEQUENCE: 153
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggca      300
tacgaaccgt atattataca cgtgacggcg gacaaccgca tcgttgccct gggcaatgat      360
ctggcggaag ccctgccggg tagcggtctg ctgacgagcc gtcatatt              408

<210> SEQ ID NO 154
<211> LENGTH: 136
<212> TYPE: PRT
<213> ORGANISM: Artificial sequence
<220> FEATURE:
<223> OTHER INFORMATION: Engineered sequence

<400> SEQUENCE: 154

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

```
Pro Gly Asp Leu Val Ile Ile Met Ser Tyr Leu Gln Ala Thr Asp Ala
            85                  90                  95

Glu Ala Lys Ala Tyr Glu Pro Tyr Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg His Ile
        130                 135

<210> SEQ ID NO 155
<211> LENGTH: 408
<212> TYPE: DNA
<213> ORGANISM: Artificial sequence
<220> FEATURE:
<223> OTHER INFORMATION: Engineered sequence

<400> SEQUENCE: 155
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccgt atattataca cgtgacggcg gacaaccgca tcgttgccct gggcaatgat     360
ctggcggaag ccctgccggg tagcggtctg ctgacgagcc gtcagatt                  408

<210> SEQ ID NO 156
<211> LENGTH: 136
<212> TYPE: PRT
<213> ORGANISM: Artificial sequence
<220> FEATURE:
<223> OTHER INFORMATION: Engineered sequence

<400> SEQUENCE: 156

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
            85                  90                  95

Glu Ala Lys Ala Tyr Glu Pro Tyr Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Gln Ile
        130                 135

<210> SEQ ID NO 157
<211> LENGTH: 408
<212> TYPE: DNA
<213> ORGANISM: Artificial sequence
```

<220> FEATURE:
<223> OTHER INFORMATION: Engineered sequence

<400> SEQUENCE: 157

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccgt atattataca cgtgacggcg gacaaccgca tcgttgccct gggcaatgat    360
ctggcggaag ccctgccggg tagcggtctg ctgacgagcc gtagttct                 408
```

<210> SEQ ID NO 158
<211> LENGTH: 136
<212> TYPE: PRT
<213> ORGANISM: Artificial sequence
<220> FEATURE:
<223> OTHER INFORMATION: Engineered sequence

<400> SEQUENCE: 158

```
Met Leu Arg Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Tyr Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ser
    130                 135
```

<210> SEQ ID NO 159
<211> LENGTH: 408
<212> TYPE: DNA
<213> ORGANISM: Artificial sequence
<220> FEATURE:
<223> OTHER INFORMATION: Engineered sequence

<400> SEQUENCE: 159

```
atgctgcgta ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccgt atattataca cgtgacggcg gacaaccgca tcgttgccct gggcaatgat    360
ctggcggaag ccctgccggg tagcggtctg ctgacgagcc gtagtctt                 408
```

<210> SEQ ID NO 160
<211> LENGTH: 136
<212> TYPE: PRT
<213> ORGANISM: Artificial sequence
<220> FEATURE:
<223> OTHER INFORMATION: Engineered sequence

<400> SEQUENCE: 160

```
Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Tyr Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 161
<211> LENGTH: 408
<212> TYPE: DNA
<213> ORGANISM: Artificial sequence
<220> FEATURE:
<223> OTHER INFORMATION: Engineered sequence

<400> SEQUENCE: 161

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 162
<211> LENGTH: 136
<212> TYPE: PRT
<213> ORGANISM: Artificial sequence
<220> FEATURE:
<223> OTHER INFORMATION: Engineered sequence

<400> SEQUENCE: 162

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
```

```
                35                  40                  45
Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
            130                 135

<210> SEQ ID NO 163
<211> LENGTH: 408
<212> TYPE: DNA
<213> ORGANISM: Artificial sequence
<220> FEATURE:
<223> OTHER INFORMATION: Engineered sequence

<400> SEQUENCE: 163
atgctgtaca ccatcctggg ttcaaaaatc catcgtgcaa cggtgacgca aagtgacctg     60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                 408

<210> SEQ ID NO 164
<211> LENGTH: 136
<212> TYPE: PRT
<213> ORGANISM: Artificial sequence
<220> FEATURE:
<223> OTHER INFORMATION: Engineered sequence

<400> SEQUENCE: 164

Met Leu Tyr Thr Ile Leu Gly Ser Lys Ile His Arg Ala Thr Val Thr
  1               5                  10                  15

Gln Ser Asp Leu Asp Tyr Val Gly Ser Val Thr Ile Asp Ala Asp Leu
                 20                  25                  30

Val His Ala Ala Gly Leu Ile Glu Gly Glu Lys Val Ala Ile Val Asp
             35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
```

-continued

```
                130                 135
```

<210> SEQ ID NO 165
<211> LENGTH: 408
<212> TYPE: DNA
<213> ORGANISM: Artificial sequence
<220> FEATURE:
<223> OTHER INFORMATION: Engineered sequence

<400> SEQUENCE: 165

```
atgctgtaca ccatcctggg ttcaaaaatc catcgtgcaa cggtgacgca agctgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 166
<211> LENGTH: 136
<212> TYPE: PRT
<213> ORGANISM: Artificial sequence
<220> FEATURE:
<223> OTHER INFORMATION: Engineered sequence

<400> SEQUENCE: 166

```
Met Leu Tyr Thr Ile Leu Gly Ser Lys Ile His Arg Ala Thr Val Thr
1               5                   10                  15

Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 167
<211> LENGTH: 408
<212> TYPE: DNA
<213> ORGANISM: Artificial sequence
<220> FEATURE:
<223> OTHER INFORMATION: Engineered sequence

<400> SEQUENCE: 167

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
```

```
gttggtgatg cgggcaccgg taacatttgc atcaatggcg cagctgcgca tctgatcaat    240
ccgggtgatc tggtgattat catgagctat ctgcaggcca cggacgccga agcaaagttt    300
tacgaaccga aaattataca cgtgacggcg gacaaccgca tcgttgccct gggcaatgat    360
ctggcggaag ccctgccggg tagcggtctg ctgacgagcc gtagtctt                 408
```

<210> SEQ ID NO 168
<211> LENGTH: 136
<212> TYPE: PRT
<213> ORGANISM: Artificial sequence
<220> FEATURE:
<223> OTHER INFORMATION: Engineered sequence

<400> SEQUENCE: 168

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Phe Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 169
<211> LENGTH: 408
<212> TYPE: DNA
<213> ORGANISM: Artificial sequence
<220> FEATURE:
<223> OTHER INFORMATION: Engineered sequence

<400> SEQUENCE: 169

```
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaagtgg    300
tacgaaccga aaattataca cgtgacggcg gacaaccgca tcgttgccct gggcaatgat    360
ctggcggaag ccctgccggg tagcggtctg ctgacgagcc gtagtctt                 408
```

<210> SEQ ID NO 170
<211> LENGTH: 136
<212> TYPE: PRT
<213> ORGANISM: Artificial sequence
<220> FEATURE:
<223> OTHER INFORMATION: Engineered sequence

<400> SEQUENCE: 170

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Trp Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 171
<211> LENGTH: 408
<212> TYPE: DNA
<213> ORGANISM: Artificial sequence
<220> FEATURE:
<223> OTHER INFORMATION: Engineered sequence

<400> SEQUENCE: 171
atgctgtaca ccatcctggg ttcaaaaatc catcgtgcaa cggtgacgca agttgacctg        60
gactatgtgg ttctgtcac gattgatgca gacctggtcc atgcagcagg tctgatcgaa       120
ggtgaaaaag ttgcaattgt cgatatcacc aacggcgctc gtctggaaac gtatgtgatt       180
gttggtgatg cgggcaccgg taacatttgc atcaatggcg cagctgcgca tctgatcaat       240
ccgggtgatc tggtgattat catgagctat ctgcaggcca cggacgccga agcaaaggca       300
tacgaaccga aaattataca cgtgacggcg gacaaccgca tcgttgccct gggcaatgat       360
ctggcggaag ccctgccggg tagcggtctg ctgacgagcc gtagtcgg                    408

<210> SEQ ID NO 172
<211> LENGTH: 136
<212> TYPE: PRT
<213> ORGANISM: Artificial sequence
<220> FEATURE:
<223> OTHER INFORMATION: Engineered sequence

<400> SEQUENCE: 172

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

```
Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Arg
    130                 135

<210> SEQ ID NO 173
<211> LENGTH: 408
<212> TYPE: DNA
<213> ORGANISM: Artificial sequence
<220> FEATURE:
<223> OTHER INFORMATION: Engineered sequence

<400> SEQUENCE: 173
atgctgtaca ccatcctggg ttcaaaaatc catcgtgcaa cggtgacgca agttgacctg       60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggca      300
tacgaaccga aaattataca cgtgacggcg gacaaccgca tcgttgccct gggcaatgat      360
ctggcggaag ccctgccggg tagcggtctg ctgacgagcc gtagtttt                   408

<210> SEQ ID NO 174
<211> LENGTH: 136
<212> TYPE: PRT
<213> ORGANISM: Artificial sequence
<220> FEATURE:
<223> OTHER INFORMATION: Engineered sequence

<400> SEQUENCE: 174

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Phe
    130                 135

<210> SEQ ID NO 175
<211> LENGTH: 408
<212> TYPE: DNA
<213> ORGANISM: Artificial sequence
<220> FEATURE:
<223> OTHER INFORMATION: Engineered sequence

<400> SEQUENCE: 175
```

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg acaaccgcg ttgttgccct gggcaatgat    360
ctggcggaag ccctgccggg tagcggtctg ctgacgagcc gtagtatt               408
```

<210> SEQ ID NO 176
<211> LENGTH: 136
<212> TYPE: PRT
<213> ORGANISM: Artificial sequence
<220> FEATURE:
<223> OTHER INFORMATION: Engineered sequence

<400> SEQUENCE: 176

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Val Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 177
<211> LENGTH: 408
<212> TYPE: DNA
<213> ORGANISM: Artificial sequence
<220> FEATURE:
<223> OTHER INFORMATION: Engineered sequence

<400> SEQUENCE: 177

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg acaaccgca tctttgccct gggcaatgat    360
ctggcggaag ccctgccggg tagcggtctg ctgacgagcc gtagtatt               408
```

<210> SEQ ID NO 178
<211> LENGTH: 136

<212> TYPE: PRT
<213> ORGANISM: Artificial sequence
<220> FEATURE:
<223> OTHER INFORMATION: Engineered sequence

<400> SEQUENCE: 178

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Phe Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 179
<211> LENGTH: 408
<212> TYPE: DNA
<213> ORGANISM: Artificial sequence
<220> FEATURE:
<223> OTHER INFORMATION: Engineered sequence

<400> SEQUENCE: 179
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg acaaccgca tctgggccct gggcaatgat    360
ctggcggaag ccctgccggg tagcggtctg ctgacgagcc gtagtatt               408

<210> SEQ ID NO 180
<211> LENGTH: 136
<212> TYPE: PRT
<213> ORGANISM: Artificial sequence
<220> FEATURE:
<223> OTHER INFORMATION: Engineered sequence

<400> SEQUENCE: 180

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Trp Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 181
<211> LENGTH: 408
<212> TYPE: DNA
<213> ORGANISM: Artificial sequence
<220> FEATURE:
<223> OTHER INFORMATION: Engineered sequence

<400> SEQUENCE: 181
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcgttgat     360
ctggcggaag ccctgccggg tagcggtctg ctgacgagcc gtagtatt                  408

<210> SEQ ID NO 182
<211> LENGTH: 136
<212> TYPE: PRT
<213> ORGANISM: Artificial sequence
<220> FEATURE:
<223> OTHER INFORMATION: Engineered sequence

<400> SEQUENCE: 182

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Val Asp Leu Ala Glu Ala Leu Pro Gly Ser
        115                 120                 125

Gly Leu Leu Thr Ser Arg Ser Ile
    130                 135

<210> SEQ ID NO 183

<210> SEQ ID NO 183
<211> LENGTH: 408
<212> TYPE: DNA
<213> ORGANISM: Artificial sequence
<220> FEATURE:
<223> OTHER INFORMATION: Engineered sequence

<400> SEQUENCE: 183

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg acaaccgca tcgttgccct gggccttgat     360
ctggcggaag ccctgccggg tagcggtctg ctgacgagcc gtagtatt                  408
```

<210> SEQ ID NO 184
<211> LENGTH: 136
<212> TYPE: PRT
<213> ORGANISM: Artificial sequence
<220> FEATURE:
<223> OTHER INFORMATION: Engineered sequence

<400> SEQUENCE: 184

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Leu Asp Leu Ala Glu Ala Leu Pro Gly Ser
        115                 120                 125
Gly Leu Leu Thr Ser Arg Ser Ile
    130                 135
```

<210> SEQ ID NO 185
<211> LENGTH: 408
<212> TYPE: DNA
<213> ORGANISM: Artificial sequence
<220> FEATURE:
<223> OTHER INFORMATION: Engineered sequence

<400> SEQUENCE: 185

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
```

```
tacgaaccga aaattataca cgtgacggcg gacaaccgca tcgttgccct gggcaatgat    360
tgtgcggaag ccctgccggg tagcggtctg ctgacgagcc gtagtatt                 408
```

<210> SEQ ID NO 186
<211> LENGTH: 136
<212> TYPE: PRT
<213> ORGANISM: Artificial sequence
<220> FEATURE:
<223> OTHER INFORMATION: Engineered sequence

<400> SEQUENCE: 186

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Cys Ala Glu Ala Leu Pro Gly Ser
        115                 120                 125

Gly Leu Leu Thr Ser Arg Ser Ile
    130                 135
```

<210> SEQ ID NO 187
<211> LENGTH: 408
<212> TYPE: DNA
<213> ORGANISM: Artificial sequence
<220> FEATURE:
<223> OTHER INFORMATION: Engineered sequence

<400> SEQUENCE: 187

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg gacaaccgca tcgttgccct gggcaatgat   360
attgcggaag ccctgccggg tagcggtctg ctgacgagcc gtagtatt                408
```

<210> SEQ ID NO 188
<211> LENGTH: 136
<212> TYPE: PRT
<213> ORGANISM: Artificial sequence
<220> FEATURE:
<223> OTHER INFORMATION: Engineered sequence

<400> SEQUENCE: 188

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
```

```
            20                  25                  30
Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Ile Ala Glu Ala Leu Pro Gly Ser
        115                 120                 125

Gly Leu Leu Thr Ser Arg Ser Ile
        130                 135
```

<210> SEQ ID NO 189
<211> LENGTH: 408
<212> TYPE: DNA
<213> ORGANISM: Artificial sequence
<220> FEATURE:
<223> OTHER INFORMATION: Engineered sequence

<400> SEQUENCE: 189

```
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg gacaaccgca tcgttgccct gggcaatgat   360
ctggcggaag ccattccggg tagcggtctg ctgacgagcc gtagtatt               408
```

<210> SEQ ID NO 190
<211> LENGTH: 136
<212> TYPE: PRT
<213> ORGANISM: Artificial sequence
<220> FEATURE:
<223> OTHER INFORMATION: Engineered sequence

<400> SEQUENCE: 190

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Ile Pro Gly Ser
```

```
                115                 120                 125
Gly Leu Leu Thr Ser Arg Ser Ile
    130                 135

<210> SEQ ID NO 191
<211> LENGTH: 408
<212> TYPE: DNA
<213> ORGANISM: Artificial sequence
<220> FEATURE:
<223> OTHER INFORMATION: Engineered sequence

<400> SEQUENCE: 191
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgtctgg tagcggtctg ctgacgagcc gtagtatt                  408

<210> SEQ ID NO 192
<211> LENGTH: 136
<212> TYPE: PRT
<213> ORGANISM: Artificial sequence
<220> FEATURE:
<223> OTHER INFORMATION: Engineered sequence

<400> SEQUENCE: 192

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Ser Gly Ser
        115                 120                 125

Gly Leu Leu Thr Ser Arg Ser Ile
    130                 135

<210> SEQ ID NO 193
<211> LENGTH: 408
<212> TYPE: DNA
<213> ORGANISM: Artificial sequence
<220> FEATURE:
<223> OTHER INFORMATION: Engineered sequence

<400> SEQUENCE: 193
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
```

```
ggtgaaaaag ttgcaattgt cgatatcacc aacggcgctc gtctggaaac gtatgtgatt        180
gttggtgatg cgggcaccgg taacatttgc atcaatggcg cagctgcgca tctgatcaat        240
ccgggtgatc tggtgattat catgagctat ctgcaggcca cggacgccga agcaaaggca        300
tacgaaccga aaattataca cgtgacggcg gacaaccgca tcgttgccct gggcaatgat        360
ctggcggaag ccctgccgga tagcggtctg ctgacgagcc gtagtatt                      408
```

<210> SEQ ID NO 194
<211> LENGTH: 136
<212> TYPE: PRT
<213> ORGANISM: Artificial sequence
<220> FEATURE:
<223> OTHER INFORMATION: Engineered sequence

<400> SEQUENCE: 194

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Asp Ser
        115                 120                 125

Gly Leu Leu Thr Ser Arg Ser Ile
    130                 135
```

<210> SEQ ID NO 195
<211> LENGTH: 408
<212> TYPE: DNA
<213> ORGANISM: Artificial sequence
<220> FEATURE:
<223> OTHER INFORMATION: Engineered sequence

<400> SEQUENCE: 195

```
atgctgtaca ccatcctggg ttcaaaaatc catcgtgcaa cggtgacgca agttgacctg         60
gactatgtgg ttctgtcac gattgatgca gacctggtcc atgcagcagg tctgatcgaa        120
ggtgaaaaag ttgcaattgt cgatatcacc aacggcgctc gtctggaaac gtatgtgatt        180
gttggtgatg cgggcaccgg taacatttgc atcaatggcg cagctgcgca tctgatcaat        240
ccgggtgatc tggtgattat catgagctat ctgcaggcca cggacgccga agcaaaggca        300
tacgaaccga aaattataca cgtgacggcg gacaaccgca tcgttgccct gggcaatgat        360
ctggcggaag ccctgccgat tagcggtctg ctgacgagcc gtagtatt                      408
```

<210> SEQ ID NO 196
<211> LENGTH: 136
<212> TYPE: PRT
<213> ORGANISM: Artificial sequence
<220> FEATURE:
<223> OTHER INFORMATION: Engineered sequence

<400> SEQUENCE: 196

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Ile Ser
        115                 120                 125

Gly Leu Leu Thr Ser Arg Ser Ile
    130                 135

<210> SEQ ID NO 197
<211> LENGTH: 408
<212> TYPE: DNA
<213> ORGANISM: Artificial sequence
<220> FEATURE:
<223> OTHER INFORMATION: Engineered sequence

<400> SEQUENCE: 197
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccgtc tagcggtctg ctgacgagcc gtagtatt                  408

<210> SEQ ID NO 198
<211> LENGTH: 136
<212> TYPE: PRT
<213> ORGANISM: Artificial sequence
<220> FEATURE:
<223> OTHER INFORMATION: Engineered sequence

<400> SEQUENCE: 198

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

```
Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Ser Ser
        115                 120                 125

Gly Leu Leu Thr Ser Arg Ser Ile
    130                 135
```

<210> SEQ ID NO 199
<211> LENGTH: 408
<212> TYPE: DNA
<213> ORGANISM: Artificial sequence
<220> FEATURE:
<223> OTHER INFORMATION: Engineered sequence

<400> SEQUENCE: 199

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccgta tagcggtctg ctgacgagcc gtagtatt                 408
```

<210> SEQ ID NO 200
<211> LENGTH: 136
<212> TYPE: PRT
<213> ORGANISM: Artificial sequence
<220> FEATURE:
<223> OTHER INFORMATION: Engineered sequence

<400> SEQUENCE: 200

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Tyr Ser
        115                 120                 125

Gly Leu Leu Thr Ser Arg Ser Ile
    130                 135
```

<210> SEQ ID NO 201
<211> LENGTH: 408
<212> TYPE: DNA
<213> ORGANISM: Artificial sequence
<220> FEATURE:

<223> OTHER INFORMATION: Engineered sequence

<400> SEQUENCE: 201

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg acaaccgca tcgttgccct gggcaatgat   360
ctggcggaag ccctgccggg tagcggtctg ctgacggttc gtagtatt              408
```

<210> SEQ ID NO 202
<211> LENGTH: 136
<212> TYPE: PRT
<213> ORGANISM: Artificial sequence
<220> FEATURE:
<223> OTHER INFORMATION: Engineered sequence

<400> SEQUENCE: 202

```
Met Leu Tyr Thr Ile Leu Gly Ser Lys Ile His Arg Ala Thr Val Thr
  1               5                  10                  15
Gln Val Asp Leu Asp Tyr Val Gly Ser Val Thr Ile Asp Ala Asp Leu
             20                  25                  30
Val His Ala Ala Gly Leu Ile Glu Gly Glu Lys Val Ala Ile Val Asp
         35                  40                  45
Ile Thr Asn Gly Ala Arg Leu Glu Thr Tyr Val Ile Val Gly Asp Ala
     50                  55                  60
Gly Thr Gly Asn Ile Cys Ile Asn Gly Ala Ala Ala His Leu Ile Asn
 65                  70                  75                  80
Pro Gly Asp Leu Val Ile Ile Met Ser Tyr Leu Gln Ala Thr Asp Ala
                 85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Val Arg Ser Ile
    130                 135
```

<210> SEQ ID NO 203
<211> LENGTH: 408
<212> TYPE: DNA
<213> ORGANISM: Artificial sequence
<220> FEATURE:
<223> OTHER INFORMATION: Engineered sequence

<400> SEQUENCE: 203

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg acaaccgca tcgttgccct gggcaatgat   360
ctggcggaag ccctgccggg tagcggtctg ctgacgagcc gtagtgag              408
```

```
<210> SEQ ID NO 204
<211> LENGTH: 136
<212> TYPE: PRT
<213> ORGANISM: Artificial sequence
<220> FEATURE:
<223> OTHER INFORMATION: Engineered sequence

<400> SEQUENCE: 204

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Glu
    130                 135

<210> SEQ ID NO 205
<211> LENGTH: 408
<212> TYPE: DNA
<213> ORGANISM: Artificial sequence
<220> FEATURE:
<223> OTHER INFORMATION: Engineered sequence

<400> SEQUENCE: 205
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408

<210> SEQ ID NO 206
<211> LENGTH: 136
<212> TYPE: PRT
<213> ORGANISM: Artificial sequence
<220> FEATURE:
<223> OTHER INFORMATION: Engineered sequence

<400> SEQUENCE: 206

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45
```

```
Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
 65                  70                  75                  80

Pro Gly Asp Leu Val Ile Met Ser Tyr Leu Gln Ala Thr Asp Ala
                 85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
            130                 135
```

<210> SEQ ID NO 207
<211> LENGTH: 408
<212> TYPE: DNA
<213> ORGANISM: Artificial sequence
<220> FEATURE:
<223> OTHER INFORMATION: Engineered sequence

<400> SEQUENCE: 207

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttcgtct gggcaatgat     360
ctggcggaag ccctgccggg tagcggtctg ctgacgagcc gtagtatt               408
```

<210> SEQ ID NO 208
<211> LENGTH: 136
<212> TYPE: PRT
<213> ORGANISM: Artificial sequence
<220> FEATURE:
<223> OTHER INFORMATION: Engineered sequence

<400> SEQUENCE: 208

```
Met Leu Tyr Thr Ile Leu Gly Ser Lys Ile His Arg Ala Thr Val Thr
  1               5                  10                  15

Gln Val Asp Leu Asp Tyr Val Gly Ser Val Thr Ile Asp Ala Asp Leu
                 20                  25                  30

Val His Ala Ala Gly Leu Ile Glu Gly Glu Lys Val Ala Ile Val Asp
             35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
 65                  70                  75                  80

Pro Gly Asp Leu Val Ile Met Ser Tyr Leu Gln Ala Thr Asp Ala
                 85                  90                  95

Glu Ala Lys Ala Tyr Glu Pro Lys Ile Ile His Val Thr Ala Asp Asn
                100                 105                 110

Arg Ile Val Arg Leu Gly Asn Asp Leu Ala Glu Ala Leu Pro Gly Ser
            115                 120                 125

Gly Leu Leu Thr Ser Arg Ser Ile
            130                 135
```

<210> SEQ ID NO 209
<211> LENGTH: 408
<212> TYPE: DNA
<213> ORGANISM: Artificial sequence
<220> FEATURE:
<223> OTHER INFORMATION: Engineered sequence

<400> SEQUENCE: 209

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggca      300
tacgaaccga aaattataca cgtgacggcg acaaccgca tcgttgtgct gggcaatgat      360
ctggcggaag ccctgccggg tagcggtctg ctgacgagcc gtagtatt                   408
```

<210> SEQ ID NO 210
<211> LENGTH: 136
<212> TYPE: PRT
<213> ORGANISM: Artificial sequence
<220> FEATURE:
<223> OTHER INFORMATION: Engineered sequence

<400> SEQUENCE: 210

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Val Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 211
<211> LENGTH: 408
<212> TYPE: DNA
<213> ORGANISM: Artificial sequence
<220> FEATURE:
<223> OTHER INFORMATION: Engineered sequence

<400> SEQUENCE: 211

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
```

```
ccgggtgatc tggtgattat catgagctat ctgcaggcca cggacgccga agcaaaggca    300
tacgaaccga aaattataca cgtgacggcg gacaaccgca tcgttgccct gcgtaatgat    360
ctggcggaag ccctgccggg tagcggtctg ctgacgagcc gtagtatt                 408
```

<210> SEQ ID NO 212
<211> LENGTH: 136
<212> TYPE: PRT
<213> ORGANISM: Artificial sequence
<220> FEATURE:
<223> OTHER INFORMATION: Engineered sequence

<400> SEQUENCE: 212

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Arg Asn Asp Leu Ala Glu Ala Leu Pro Gly Ser
        115                 120                 125

Gly Leu Leu Thr Ser Arg Ser Ile
    130                 135
```

<210> SEQ ID NO 213
<211> LENGTH: 408
<212> TYPE: DNA
<213> ORGANISM: Artificial sequence
<220> FEATURE:
<223> OTHER INFORMATION: Engineered sequence

<400> SEQUENCE: 213

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gtgtaatgat    360
ctggcggaag ccctgccggg tagcggtctg ctgacgagcc gtagtatt                 408
```

<210> SEQ ID NO 214
<211> LENGTH: 136
<212> TYPE: PRT
<213> ORGANISM: Artificial sequence
<220> FEATURE:
<223> OTHER INFORMATION: Engineered sequence

<400> SEQUENCE: 214

```
Met Leu Tyr Thr Ile Leu Gly Ser Lys Ile His Arg Ala Thr Val Thr
```

```
                1               5                   10                  15
            Gln Val Asp Leu Asp Tyr Val Gly Ser Val Thr Ile Asp Ala Asp Leu
                        20                  25                  30

Val His Ala Ala Gly Leu Ile Glu Gly Glu Lys Val Ala Ile Val Asp
                        35                  40                  45

Ile Thr Asn Gly Ala Arg Leu Glu Thr Tyr Val Ile Val Gly Asp Ala
                        50                  55                  60

Gly Thr Gly Asn Ile Cys Ile Asn Gly Ala Ala His Leu Ile Asn
             65                 70                  75                  80

Pro Gly Asp Leu Val Ile Ile Met Ser Tyr Leu Gln Ala Thr Asp Ala
                            85                  90                  95

Glu Ala Lys Ala Tyr Glu Pro Lys Ile Ile His Val Thr Ala Asp Asn
                            100                 105                 110

Arg Ile Val Ala Leu Cys Asn Asp Leu Ala Glu Ala Leu Pro Gly Ser
                            115                 120                 125

Gly Leu Leu Thr Ser Arg Ser Ile
                            130                 135
```

<210> SEQ ID NO 215
<211> LENGTH: 408
<212> TYPE: DNA
<213> ORGANISM: Artificial sequence
<220> FEATURE:
<223> OTHER INFORMATION: Engineered sequence

<400> SEQUENCE: 215

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg taagggtctg ctgacgagcc gtagtatt                  408
```

<210> SEQ ID NO 216
<211> LENGTH: 136
<212> TYPE: PRT
<213> ORGANISM: Artificial sequence
<220> FEATURE:
<223> OTHER INFORMATION: Engineered sequence

<400> SEQUENCE: 216

```
            Met Leu Tyr Thr Ile Leu Gly Ser Lys Ile His Arg Ala Thr Val Thr
             1               5                   10                  15

Gln Val Asp Leu Asp Tyr Val Gly Ser Val Thr Ile Asp Ala Asp Leu
                            20                  25                  30

Val His Ala Ala Gly Leu Ile Glu Gly Glu Lys Val Ala Ile Val Asp
                            35                  40                  45

Ile Thr Asn Gly Ala Arg Leu Glu Thr Tyr Val Ile Val Gly Asp Ala
                            50                  55                  60

Gly Thr Gly Asn Ile Cys Ile Asn Gly Ala Ala His Leu Ile Asn
             65                 70                  75                  80

Pro Gly Asp Leu Val Ile Ile Met Ser Tyr Leu Gln Ala Thr Asp Ala
                            85                  90                  95

Glu Ala Lys Ala Tyr Glu Pro Lys Ile Ile His Val Thr Ala Asp Asn
```

```
                100              105              110
Arg Ile Val Ala Leu Gly Asn Asp Leu Ala Glu Ala Leu Pro Gly Lys
            115                  120                  125

Gly Leu Leu Thr Ser Arg Ser Ile
        130                 135

<210> SEQ ID NO 217
<211> LENGTH: 408
<212> TYPE: DNA
<213> ORGANISM: Artificial sequence
<220> FEATURE:
<223> OTHER INFORMATION: Engineered sequence

<400> SEQUENCE: 217
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct ggcaatgat      360 ctggcggaag ccctgccggg tcttggtctg ctgacgagcc gtagtatt                  408

<210> SEQ ID NO 218
<211> LENGTH: 136
<212> TYPE: PRT
<213> ORGANISM: Artificial sequence
<220> FEATURE:
<223> OTHER INFORMATION: Engineered sequence

<400> SEQUENCE: 218

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Leu
        115                 120                 125

Gly Leu Leu Thr Ser Arg Ser Ile
    130                 135

<210> SEQ ID NO 219
<211> LENGTH: 408
<212> TYPE: DNA
<213> ORGANISM: Artificial sequence
<220> FEATURE:
<223> OTHER INFORMATION: Engineered sequence

<400> SEQUENCE: 219
```

```
atgctgtaca ccatcctggg ttcaaaaatc catcgtgcaa cggtgacgca agttgacctg        60
gactatgtgg gttctgtcac gattgatgca gacctggtcc atgcagcagg tctgatcgaa       120
ggtgaaaaag ttgcaattgt cgatatcacc aacggcgctc gtctggaaac gtatgtgatt       180
gttggtgatg cgggcaccgg taacatttgc atcaatggcg cagctgcgca tctgatcaat       240
ccgggtgatc tggtgattat catgagctat ctgcaggcca cggacgccga agcaactgca       300
tacgaaccga aaattataca cgtgacggcg gacaaccgca tcgttgccct gggcaatgat       360
ctggcggaag ccctgccggg tagcggtctg ctgacgagcc gtagtatt                    408
```

```
<210> SEQ ID NO 220
<211> LENGTH: 136
<212> TYPE: PRT
<213> ORGANISM: Artificial sequence
<220> FEATURE:
<223> OTHER INFORMATION: Engineered sequence

<400> SEQUENCE: 220
```

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Thr Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

```
<210> SEQ ID NO 221
<211> LENGTH: 408
<212> TYPE: DNA
<213> ORGANISM: Artificial sequence
<220> FEATURE:
<223> OTHER INFORMATION: Engineered sequence

<400> SEQUENCE: 221
atgctgtaca ccatcctggg ttcaaaaatc catcgtgcaa cggtgacgca agttgacctg        60
gactatgtgg gttctgtcac gattgatgca gacctggtcc atgcagcagg tctgatcgaa       120
ggtgaaaaag ttgcaattgt cgatatcacc aacggcgctc gtctggaaac gtatgtgatt       180
gttggtgatg cgggcaccgg taacatttgc atcaatggcg cagctgcgca tctgatcaat       240
ccgggtgatc tggtgattat catgagctat ctgcaggcca cggacgccga agcagatgca       300
tacgaaccga aaattataca cgtgacggcg gacaaccgca tcgttgccct gggcaatgat       360
ctggcggaag ccctgccggg tagcggtctg ctgacgagcc gtagtatt                    408
```

```
<210> SEQ ID NO 222
<211> LENGTH: 136
<212> TYPE: PRT
```

<213> ORGANISM: Artificial sequence
<220> FEATURE:
<223> OTHER INFORMATION: Engineered sequence

<400> SEQUENCE: 222

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Asp Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 223
<211> LENGTH: 408
<212> TYPE: DNA
<213> ORGANISM: Artificial sequence
<220> FEATURE:
<223> OTHER INFORMATION: Engineered sequence

<400> SEQUENCE: 223

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcatcggca     300
tacgaaccga aaattataca cgtgacggcg gacaaccgca tcgttgccct gggcaatgat     360
ctggcggaag ccctgccggg tagcggtctg ctgacgagcc gtagtatt                  408
```

<210> SEQ ID NO 224
<211> LENGTH: 136
<212> TYPE: PRT
<213> ORGANISM: Artificial sequence
<220> FEATURE:
<223> OTHER INFORMATION: Engineered sequence

<400> SEQUENCE: 224

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60
```

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Ser Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
        130                 135

<210> SEQ ID NO 225
<211> LENGTH: 408
<212> TYPE: DNA
<213> ORGANISM: Artificial sequence
<220> FEATURE:
<223> OTHER INFORMATION: Engineered sequence

<400> SEQUENCE: 225
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg acaaccgca tcgttgccct gggcaatgat     360
ctgggtgaag ccctgccggg tagcggtctg ctgacgagcc gtagtatt               408

<210> SEQ ID NO 226
<211> LENGTH: 136
<212> TYPE: PRT
<213> ORGANISM: Artificial sequence
<220> FEATURE:
<223> OTHER INFORMATION: Engineered sequence

<400> SEQUENCE: 226

Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
                 20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Gly Glu Ala Leu Pro Gly Ser
        115                 120                 125

Gly Leu Leu Thr Ser Arg Ser Ile
        130                 135

<210> SEQ ID NO 227
<211> LENGTH: 408

<212> TYPE: DNA
<213> ORGANISM: Artificial sequence
<220> FEATURE:
<223> OTHER INFORMATION: Engineered sequence

<400> SEQUENCE: 227

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaag ccctgccggg tagcggtctg ctgacgagcc gtagtatt                  408
```

<210> SEQ ID NO 228
<211> LENGTH: 136
<212> TYPE: PRT
<213> ORGANISM: Artificial sequence
<220> FEATURE:
<223> OTHER INFORMATION: Engineered sequence

<400> SEQUENCE: 228

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
                20                  25                  30
Val His Ala Ala Gly Leu Ile Glu Gly Glu Lys Val Ala Ile Val Asp
            35                  40                  45
Ile Thr Asn Gly Ala Arg Leu Glu Thr Tyr Val Ile Val Gly Asp Ala
        50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ser Glu Ala Leu Pro Gly Ser
        115                 120                 125
Gly Leu Leu Thr Ser Arg Ser Ile
    130                 135
```

<210> SEQ ID NO 229
<211> LENGTH: 408
<212> TYPE: DNA
<213> ORGANISM: Artificial sequence
<220> FEATURE:
<223> OTHER INFORMATION: Engineered sequence

<400> SEQUENCE: 229

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
```

```
ctggcggaag ccctgccggg tagcggtctg ctgtatagcc gtagtatt          408
```

<210> SEQ ID NO 230
<211> LENGTH: 136
<212> TYPE: PRT
<213> ORGANISM: Artificial sequence
<220> FEATURE:
<223> OTHER INFORMATION: Engineered sequence

<400> SEQUENCE: 230

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Tyr Ser Arg Ser Ile
    130                 135
```

<210> SEQ ID NO 231
<211> LENGTH: 408
<212> TYPE: DNA
<213> ORGANISM: Artificial sequence
<220> FEATURE:
<223> OTHER INFORMATION: Engineered sequence

<400> SEQUENCE: 231

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg acaaccgca tcgttgccct gggcaatgat      360
ctggcggaag ccctgccggg tagcggtctg ctgccgagcc gtagtatt                  408
```

<210> SEQ ID NO 232
<211> LENGTH: 136
<212> TYPE: PRT
<213> ORGANISM: Artificial sequence
<220> FEATURE:
<223> OTHER INFORMATION: Engineered sequence

<400> SEQUENCE: 232

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30
```

Val His Ala Ala Gly Leu Ile Glu Gly Glu Lys Val Ala Ile Val Asp
         35                  40                  45

Ile Thr Asn Gly Ala Arg Leu Glu Thr Tyr Val Ile Val Gly Asp Ala
     50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
             100                 105                 110

Arg Ile Val Ala Leu Gly Asn Asp Leu Ala Glu Ala Leu Pro Gly Ser
             115                 120                 125

Gly Leu Leu Pro Ser Arg Ser Ile
        130                 135

<210> SEQ ID NO 233
<211> LENGTH: 408
<212> TYPE: DNA
<213> ORGANISM: Artificial sequence
<220> FEATURE:
<223> OTHER INFORMATION: Engineered sequence

<400> SEQUENCE: 233
atgctgtaca ccatcctggg ttcaaaaatc catcgtgcaa cggtgacgca agttgacctg     60
gactatgtgg ttctgtcac gattgatgca gacctgattc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg acaaccgca tcgttgccct gggcaatgat    360
ctggcggaag ccctgccggg tagcggtctg ctgacgagcc gtagtatt              408

<210> SEQ ID NO 234
<211> LENGTH: 136
<212> TYPE: PRT
<213> ORGANISM: Artificial sequence
<220> FEATURE:
<223> OTHER INFORMATION: Engineered sequence

<400> SEQUENCE: 234

Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
             20                  25                  30

Ile His Ala Ala Gly Leu Ile Glu Gly Lys Val Ala Ile Val Asp
         35                  40                  45

Ile Thr Asn Gly Ala Arg Leu Glu Thr Tyr Val Ile Val Gly Asp Ala
     50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
             100                 105                 110

Arg Ile Val Ala Leu Gly Asn Asp Leu Ala Glu Ala Leu Pro Gly Ser
             115                 120                 125

Gly Leu Leu Thr Ser Arg Ser Ile
    130                 135

<210> SEQ ID NO 235
<211> LENGTH: 408
<212> TYPE: DNA
<213> ORGANISM: Artificial sequence
<220> FEATURE:
<223> OTHER INFORMATION: Engineered sequence

<400> SEQUENCE: 235
atgctgtaca ccatcctggg ttcaaaaatc catcgtgcaa cggtgacgca agttgacctg      60
gactatgtgg gttctgtcac gattgatgca gacctggtcc tggcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg acaaccgca tcgttgccct gggcaatgat      360
ctggcggaag ccctgccggg tagcggtctg ctgacgagcc gtagtatt                  408

<210> SEQ ID NO 236
<211> LENGTH: 136
<212> TYPE: PRT
<213> ORGANISM: Artificial sequence
<220> FEATURE:
<223> OTHER INFORMATION: Engineered sequence

<400> SEQUENCE: 236

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val Leu Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 237
<211> LENGTH: 408
<212> TYPE: DNA
<213> ORGANISM: Artificial sequence
<220> FEATURE:
<223> OTHER INFORMATION: Engineered sequence

<400> SEQUENCE: 237
atgctgtaca ccatcctggg ttcaaaaatc catcgtgcaa cggtgacgca agttgacctg      60
gactatgtgg gttctgtcac gattgatgca gacctggtct tgcagcagg tctgatcgaa      120

```
ggtgaaaaag ttgcaattgt cgatatcacc aacggcgctc gtctggaaac gtatgtgatt        180
gttggtgatg cgggcaccgg taacatttgc atcaatggcg cagctgcgca tctgatcaat        240
ccgggtgatc tggtgattat catgagctat ctgcaggcca cggacgccga agcaaaggca        300
tacgaaccga aaattataca cgtgacggcg gacaaccgca tcgttgccct gggcaatgat        360
ctggcggaag ccctgccggg tagcggtctg ctgacgagcc gtagtatt                     408
```

<210> SEQ ID NO 238
<211> LENGTH: 136
<212> TYPE: PRT
<213> ORGANISM: Artificial sequence
<220> FEATURE:
<223> OTHER INFORMATION: Engineered sequence

<400> SEQUENCE: 238

```
Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
            20                  25                  30

Val Tyr Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 239
<211> LENGTH: 408
<212> TYPE: DNA
<213> ORGANISM: Artificial sequence
<220> FEATURE:
<223> OTHER INFORMATION: Engineered sequence

<400> SEQUENCE: 239

```
atgctgtaca ccatcctggg ttcaaaaatc catcgtgcaa cggtgacgca agttgacctg         60
gactatgtgg gttctgtcac gattgatgca gacctggtcc atgcagcagg tctgcttgaa        120
ggtgaaaaag ttgcaattgt cgatatcacc aacggcgctc gtctggaaac gtatgtgatt        180
gttggtgatg cgggcaccgg taacatttgc atcaatggcg cagctgcgca tctgatcaat        240
ccgggtgatc tggtgattat catgagctat ctgcaggcca cggacgccga agcaaaggca        300
tacgaaccga aaattataca cgtgacggcg gacaaccgca tcgttgccct gggcaatgat        360
ctggcggaag ccctgccggg tagcggtctg ctgacgagcc gtagtatt                     408
```

<210> SEQ ID NO 240
<211> LENGTH: 136
<212> TYPE: PRT
<213> ORGANISM: Artificial sequence
<220> FEATURE:
<223> OTHER INFORMATION: Engineered sequence

<400> SEQUENCE: 240

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Leu Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 241
<211> LENGTH: 408
<212> TYPE: DNA
<213> ORGANISM: Artificial sequence
<220> FEATURE:
<223> OTHER INFORMATION: Engineered sequence

<400> SEQUENCE: 241
atgctgtaca ccatcctggg ttcaaaaatc catcgtgcaa cggtgacgca agttgacctg      60
gactatgtgg ttctgtcac gattgatgca gacctggtcc atgcagcagg tctgcgggaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg acaaccgca tcgttgccct gggcaatgat     360
ctggcggaag ccctgccggg tagcggtctg ctgacgagcc gtagtatt               408

<210> SEQ ID NO 242
<211> LENGTH: 136
<212> TYPE: PRT
<213> ORGANISM: Artificial sequence
<220> FEATURE:
<223> OTHER INFORMATION: Engineered sequence

<400> SEQUENCE: 242

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala 85                  90                  95
Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 243
<211> LENGTH: 408
<212> TYPE: DNA
<213> ORGANISM: Artificial sequence
<220> FEATURE:
<223> OTHER INFORMATION: Engineered sequence

<400> SEQUENCE: 243
atgctgtaca ccatcctggg ttcaaaaatc catcgtgcaa cggtgacgca agttgacctg      60
gactatgtgg ttctgtcac gattgatgca gacctggtcc atgcagcagg tctgatggaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408

<210> SEQ ID NO 244
<211> LENGTH: 136
<212> TYPE: PRT
<213> ORGANISM: Artificial sequence
<220> FEATURE:
<223> OTHER INFORMATION: Engineered sequence

<400> SEQUENCE: 244

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Met Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 245
<211> LENGTH: 408
<212> TYPE: DNA
<213> ORGANISM: Artificial sequence
<220> FEATURE:
<223> OTHER INFORMATION: Engineered sequence

<400> SEQUENCE: 245

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacattaag atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408
```

<210> SEQ ID NO 246
<211> LENGTH: 136
<212> TYPE: PRT
<213> ORGANISM: Artificial sequence
<220> FEATURE:
<223> OTHER INFORMATION: Engineered sequence

<400> SEQUENCE: 246

```
Met Leu Tyr Thr Ile Leu Gly Ser Lys Ile His Arg Ala Thr Val Thr
  1               5                  10                  15

Gln Val Asp Leu Asp Tyr Val Gly Ser Val Thr Ile Asp Ala Asp Leu
             20                  25                  30

Val His Ala Ala Gly Leu Ile Glu Gly Glu Lys Val Ala Ile Val Asp
         35                  40                  45

Ile Thr Asn Gly Ala Arg Leu Glu Thr Tyr Val Ile Val Gly Asp Ala
     50                  55                  60

Gly Thr Gly Asn Ile Lys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 247
<211> LENGTH: 408
<212> TYPE: DNA
<213> ORGANISM: Artificial sequence
<220> FEATURE:
<223> OTHER INFORMATION: Engineered sequence

<400> SEQUENCE: 247

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
atgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408
```

<210> SEQ ID NO 248
<211> LENGTH: 136
<212> TYPE: PRT
<213> ORGANISM: Artificial sequence
<220> FEATURE:
<223> OTHER INFORMATION: Engineered sequence

<400> SEQUENCE: 248

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Met Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 249
<211> LENGTH: 408
<212> TYPE: DNA
<213> ORGANISM: Artificial sequence
<220> FEATURE:
<223> OTHER INFORMATION: Engineered sequence

<400> SEQUENCE: 249

```
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
gttggtgatc tggtgattat catgagctat ctgcaggcca cggacgccga agcaaaggca    300
tacgaaccga aaattataca cgtgacggcg acaaccgca tcgttgccct gggcaatgat    360
ctggcggaag ccctgccggg tagcggtctg ctgacgagcc gtagtatt               408
```

<210> SEQ ID NO 250
<211> LENGTH: 136
<212> TYPE: PRT
<213> ORGANISM: Artificial sequence
<220> FEATURE:
<223> OTHER INFORMATION: Engineered sequence

<400> SEQUENCE: 250

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45
```

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Val Gly Asp Leu Val Ile Ile Met Ser Tyr Leu Gln Ala Thr Asp Ala
                    85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 251
<211> LENGTH: 408
<212> TYPE: DNA
<213> ORGANISM: Artificial sequence
<220> FEATURE:
<223> OTHER INFORMATION: Engineered sequence

<400> SEQUENCE: 251
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctgaaaac gtatgtgatt    180
gttggtgatg cgggcaccgg taacatttgc atcaatggcg cagctgcgca tctgatcaat    240
attggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                408

<210> SEQ ID NO 252
<211> LENGTH: 136
<212> TYPE: PRT
<213> ORGANISM: Artificial sequence
<220> FEATURE:
<223> OTHER INFORMATION: Engineered sequence

<400> SEQUENCE: 252

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Ile Gly Asp Leu Val Ile Ile Met Ser Tyr Leu Gln Ala Thr Asp Ala
                    85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 253
<211> LENGTH: 408
<212> TYPE: DNA
<213> ORGANISM: Artificial sequence
<220> FEATURE:
<223> OTHER INFORMATION: Engineered sequence

<400> SEQUENCE: 253

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ttgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt                 408
```

<210> SEQ ID NO 254
<211> LENGTH: 136
<212> TYPE: PRT
<213> ORGANISM: Artificial sequence
<220> FEATURE:
<223> OTHER INFORMATION: Engineered sequence

<400> SEQUENCE: 254

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Leu Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 255
<211> LENGTH: 408
<212> TYPE: DNA
<213> ORGANISM: Artificial sequence
<220> FEATURE:
<223> OTHER INFORMATION: Engineered sequence

<400> SEQUENCE: 255

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
```

```
gctggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                 408
```

<210> SEQ ID NO 256
<211> LENGTH: 136
<212> TYPE: PRT
<213> ORGANISM: Artificial sequence
<220> FEATURE:
<223> OTHER INFORMATION: Engineered sequence

<400> SEQUENCE: 256

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Ala Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 257
<211> LENGTH: 408
<212> TYPE: DNA
<213> ORGANISM: Artificial sequence
<220> FEATURE:
<223> OTHER INFORMATION: Engineered sequence

<400> SEQUENCE: 257

```
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggtta cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                  408
```

<210> SEQ ID NO 258
<211> LENGTH: 136
<212> TYPE: PRT
<213> ORGANISM: Artificial sequence
<220> FEATURE:
<223> OTHER INFORMATION: Engineered sequence

<400> SEQUENCE: 258

```
Met Leu Tyr Thr Ile Leu Gly Ser Lys Ile His Arg Ala Thr Val Thr
1               5                   10                  15
```

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Val Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 259
<211> LENGTH: 408
<212> TYPE: DNA
<213> ORGANISM: Artificial sequence
<220> FEATURE:
<223> OTHER INFORMATION: Engineered sequence

<400> SEQUENCE: 259
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcttgcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408

<210> SEQ ID NO 260
<211> LENGTH: 136
<212> TYPE: PRT
<213> ORGANISM: Artificial sequence
<220> FEATURE:
<223> OTHER INFORMATION: Engineered sequence

<400> SEQUENCE: 260

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Leu Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 261
<211> LENGTH: 408
<212> TYPE: DNA
<213> ORGANISM: Artificial sequence
<220> FEATURE:
<223> OTHER INFORMATION: Engineered sequence

<400> SEQUENCE: 261
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctggttgcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt                  408

<210> SEQ ID NO 262
<211> LENGTH: 136
<212> TYPE: PRT
<213> ORGANISM: Artificial sequence
<220> FEATURE:
<223> OTHER INFORMATION: Engineered sequence

<400> SEQUENCE: 262

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Val Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 263
<211> LENGTH: 408
<212> TYPE: DNA
<213> ORGANISM: Artificial sequence
<220> FEATURE:
<223> OTHER INFORMATION: Engineered sequence

<400> SEQUENCE: 263
atgctgtaca ccatcctggg ttcaaaaatc catcgtgcaa cggtgacgca agttgacctg      60

```
aattatgtgg gttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                 408
```

<210> SEQ ID NO 264
<211> LENGTH: 136
<212> TYPE: PRT
<213> ORGANISM: Artificial sequence
<220> FEATURE:
<223> OTHER INFORMATION: Engineered sequence

<400> SEQUENCE: 264

```
Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 265
<211> LENGTH: 408
<212> TYPE: DNA
<213> ORGANISM: Artificial sequence
<220> FEATURE:
<223> OTHER INFORMATION: Engineered sequence

<400> SEQUENCE: 265

```
atgctgtaca ccatcctggg ttcaaaaatc catcgtgcaa cggtgacgca agttgacctg     60
gactatgtgg ttctgtcac gattgatggt gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                 408
```

<210> SEQ ID NO 266
<211> LENGTH: 136
<212> TYPE: PRT
<213> ORGANISM: Artificial sequence
<220> FEATURE:
<223> OTHER INFORMATION: Engineered sequence

<400> SEQUENCE: 266

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Gly Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 267
<211> LENGTH: 408
<212> TYPE: DNA
<213> ORGANISM: Artificial sequence
<220> FEATURE:
<223> OTHER INFORMATION: Engineered sequence

<400> SEQUENCE: 267
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg tgctatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408

<210> SEQ ID NO 268
<211> LENGTH: 136
<212> TYPE: PRT
<213> ORGANISM: Artificial sequence
<220> FEATURE:
<223> OTHER INFORMATION: Engineered sequence

<400> SEQUENCE: 268

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Ala Ile Cys Ile Asn Gly Ala Ala Ala His Leu Ile Asn

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 269
<211> LENGTH: 408
<212> TYPE: DNA
<213> ORGANISM: Artificial sequence
<220> FEATURE:
<223> OTHER INFORMATION: Engineered sequence

<400> SEQUENCE: 269
atgctgtaca ccatcctggg ttcaaaaatc catcgtgcaa cggtgacgca agttgacctg    60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taagatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt                408

<210> SEQ ID NO 270
<211> LENGTH: 136
<212> TYPE: PRT
<213> ORGANISM: Artificial sequence
<220> FEATURE:
<223> OTHER INFORMATION: Engineered sequence

<400> SEQUENCE: 270

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Lys Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135

<210> SEQ ID NO 271
<211> LENGTH: 408
<212> TYPE: DNA

<213> ORGANISM: Artificial sequence
<220> FEATURE:
<223> OTHER INFORMATION: Engineered sequence

<400> SEQUENCE: 271

```
atgctgtaca ccatcctggg ttcaaaaatc catcgtgcaa cggtgacgca agttgacctg    60
gactatgtgg ttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg tcggatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg gacaaccgca tcgttgccct gggcaatgat   360
ctggcggaag ccctgccggg tagcggtctg ctgacgagcc gtagtatt              408
```

<210> SEQ ID NO 272
<211> LENGTH: 136
<212> TYPE: PRT
<213> ORGANISM: Artificial sequence
<220> FEATURE:
<223> OTHER INFORMATION: Engineered sequence

<400> SEQUENCE: 272

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Arg Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 273
<211> LENGTH: 408
<212> TYPE: DNA
<213> ORGANISM: Artificial sequence
<220> FEATURE:
<223> OTHER INFORMATION: Engineered sequence

<400> SEQUENCE: 273

```
atgctgtaca ccatcctggg ttcaaaaatc catcgtgcaa cggtgacgca agttgacctg    60
gactatgtgg ttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg tgagatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg gacaaccgca tcgttgccct gggcaatgat   360
```

```
ctggcggaag ccctgccggg tagcggtctg ctgacgagcc gtagtatt            408
```

<210> SEQ ID NO 274
<211> LENGTH: 136
<212> TYPE: PRT
<213> ORGANISM: Artificial sequence
<220> FEATURE:
<223> OTHER INFORMATION: Engineered sequence

<400> SEQUENCE: 274

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Glu Ile Cys Ile Asn Gly Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 275
<211> LENGTH: 408
<212> TYPE: DNA
<213> ORGANISM: Artificial sequence
<220> FEATURE:
<223> OTHER INFORMATION: Engineered sequence

<400> SEQUENCE: 275

```
atgctgtaca ccatcctggg ttcaaaaatc catcgtgcaa cggtgacgca agttgacctg    60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcttt    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtatt             408
```

<210> SEQ ID NO 276
<211> LENGTH: 136
<212> TYPE: PRT
<213> ORGANISM: Artificial sequence
<220> FEATURE:
<223> OTHER INFORMATION: Engineered sequence

<400> SEQUENCE: 276

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30
```

Val His Ala Ala Gly Leu Ile Glu Gly Glu Lys Val Ala Ile Val Asp
    35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Phe
 65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
130                 135

<210> SEQ ID NO 277
<211> LENGTH: 408
<212> TYPE: DNA
<213> ORGANISM: Artificial sequence
<220> FEATURE:
<223> OTHER INFORMATION: Engineered sequence

<400> SEQUENCE: 277
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat tatcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt                  408

<210> SEQ ID NO 278
<211> LENGTH: 136
<212> TYPE: PRT
<213> ORGANISM: Artificial sequence
<220> FEATURE:
<223> OTHER INFORMATION: Engineered sequence

<400> SEQUENCE: 278

Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
                20                  25                  30

Val His Ala Ala Gly Leu Ile Glu Gly Glu Lys Val Ala Ile Val Asp
            35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Tyr Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135

<210> SEQ ID NO 279
<211> LENGTH: 408
<212> TYPE: DNA
<213> ORGANISM: Artificial sequence
<220> FEATURE:
<223> OTHER INFORMATION: Engineered sequence

<400> SEQUENCE: 279
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga gtattataca cgtgacggcg acaaccgca tcgttgccct gggcaatgat    360
ctggcggaag ccctgccggg tagcggtctg ctgacgagcc gtagtatt              408

<210> SEQ ID NO 280
<211> LENGTH: 136
<212> TYPE: PRT
<213> ORGANISM: Artificial sequence
<220> FEATURE:
<223> OTHER INFORMATION: Engineered sequence

<400> SEQUENCE: 280

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Ser Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 281
<211> LENGTH: 408
<212> TYPE: DNA
<213> ORGANISM: Artificial sequence
<220> FEATURE:
<223> OTHER INFORMATION: Engineered sequence

<400> SEQUENCE: 281
atgctgtaca ccatcctggg ttcaaaaatc catcgtgcaa cggtgacgca agttgacctg     60
gactatgtgg ttctgtcac gattgatgca gacctggtcc atgcagcagg tctgatcgaa    120
ggtgaaaaag ttgcaattgt cgatatcacc aacggcgctc gtctggaaac gtatgtgatt    180

```
gttggtgatg cgggcaccgg taacatttgc atcaatggcg cagctgcgca tctgatcaat      240
ccgggtgatc tggtgattat catgagctat ctgcaggcca cggacgccga agcaaaggca      300
tacaagccga aaattataca cgtgacggcg gacaaccgca tcgttgccct gggcaatgat      360
ctggcggaag ccctgccggg tagcggtctg ctgacgagcc gtagtatt                   408
```

<210> SEQ ID NO 282
<211> LENGTH: 136
<212> TYPE: PRT
<213> ORGANISM: Artificial sequence
<220> FEATURE:
<223> OTHER INFORMATION: Engineered sequence

<400> SEQUENCE: 282

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Lys Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 283
<211> LENGTH: 408
<212> TYPE: DNA
<213> ORGANISM: Artificial sequence
<220> FEATURE:
<223> OTHER INFORMATION: Engineered sequence

<400> SEQUENCE: 283

```
atgctgtaca ccatcctggg ttcaaaaatc catcgtgcaa cggtgacgca agttgacctg       60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacttgccga aaattataca cgtgacggcg gacaaccgca tcgttgccct gggcaatgat     360
ctggcggaag ccctgccggg tagcggtctg ctgacgagcc gtagtatt                  408
```

<210> SEQ ID NO 284
<211> LENGTH: 136
<212> TYPE: PRT
<213> ORGANISM: Artificial sequence
<220> FEATURE:
<223> OTHER INFORMATION: Engineered sequence

<400> SEQUENCE: 284

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Leu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
        130                 135
```

<210> SEQ ID NO 285
<211> LENGTH: 408
<212> TYPE: DNA
<213> ORGANISM: Artificial sequence
<220> FEATURE:
<223> OTHER INFORMATION: Engineered sequence

<400> SEQUENCE: 285

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga atattataca cgtgacggcg gacaaccgca tcgttgccct gggcaatgat     360
ctggcggaag ccctgccggg tagcggtctg ctgacgagcc gtagtatt               408
```

<210> SEQ ID NO 286
<211> LENGTH: 136
<212> TYPE: PRT
<213> ORGANISM: Artificial sequence
<220> FEATURE:
<223> OTHER INFORMATION: Engineered sequence

<400> SEQUENCE: 286

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95
```

```
Glu Ala Lys Ala Tyr Glu Pro Asn Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 287
<211> LENGTH: 408
<212> TYPE: DNA
<213> ORGANISM: Artificial sequence
<220> FEATURE:
<223> OTHER INFORMATION: Engineered sequence

<400> SEQUENCE: 287
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
taccagccga aaattataca cgtgacggcg gacaaccgca tcgttgccct gggcaatgat     360
ctggcggaag ccctgccggg tagcggtctg ctgacgagcc gtagtatt               408

<210> SEQ ID NO 288
<211> LENGTH: 136
<212> TYPE: PRT
<213> ORGANISM: Artificial sequence
<220> FEATURE:
<223> OTHER INFORMATION: Engineered sequence

<400> SEQUENCE: 288

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Gln Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 289
<211> LENGTH: 408
<212> TYPE: DNA
<213> ORGANISM: Artificial sequence
<220> FEATURE:
<223> OTHER INFORMATION: Engineered sequence
```

<400> SEQUENCE: 289

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacacgccga aaattataca cgtgacggcg gacaaccgca tcgttgccct gggcaatgat     360
ctggcggaag ccctgccggg tagcggtctg ctgacgagcc gtagtatt                  408
```

<210> SEQ ID NO 290
<211> LENGTH: 136
<212> TYPE: PRT
<213> ORGANISM: Artificial sequence
<220> FEATURE:
<223> OTHER INFORMATION: Engineered sequence

<400> SEQUENCE: 290

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Thr Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 291
<211> LENGTH: 408
<212> TYPE: DNA
<213> ORGANISM: Artificial sequence
<220> FEATURE:
<223> OTHER INFORMATION: Engineered sequence

<400> SEQUENCE: 291

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacgctt gacaaccgca tcgttgccct gggcaatgat     360
ctggcggaag ccctgccggg tagcggtctg ctgacgagcc gtagtatt                  408
```

<210> SEQ ID NO 292

```
<211> LENGTH: 136
<212> TYPE: PRT
<213> ORGANISM: Artificial sequence
<220> FEATURE:
<223> OTHER INFORMATION: Engineered sequence

<400> SEQUENCE: 292

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Met Ser Tyr Leu Gln Ala Thr Asp Ala
                85                  90                  95

Glu Ala Lys Ala Tyr Glu Pro Lys Ile Ile His Val Thr Leu Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 293
<211> LENGTH: 408
<212> TYPE: DNA
<213> ORGANISM: Artificial sequence
<220> FEATURE:
<223> OTHER INFORMATION: Engineered sequence

<400> SEQUENCE: 293
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcaggcca cggacgccga agcaaaggca      300
tacgaaccga aaattataca cgtgacgatg gacaaccgca tcgttgccct gggcaatgat      360
ctggcggaag ccctgccggg tagcggtctg ctgacgagcc gtagtatt              408

<210> SEQ ID NO 294
<211> LENGTH: 136
<212> TYPE: PRT
<213> ORGANISM: Artificial sequence
<220> FEATURE:
<223> OTHER INFORMATION: Engineered sequence

<400> SEQUENCE: 294

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
```

```
                50                  55                  60
Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Met Asp Asn
                100                 105                 110

Arg Ile Val Ala Leu Gly Asn Asp Leu Ala Glu Ala Leu Pro Gly Ser
                115                 120                 125

Gly Leu Leu Thr Ser Arg Ser Ile
    130                 135

<210> SEQ ID NO 295
<211> LENGTH: 408
<212> TYPE: DNA
<213> ORGANISM: Artificial sequence
<220> FEATURE:
<223> OTHER INFORMATION: Engineered sequence

<400> SEQUENCE: 295
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacgtcg gacaaccgca tcgttgccct gggcaatgat     360
ctggcggaag ccctgccggg tagcggtctg ctgacgagcc gtagtatt                  408

<210> SEQ ID NO 296
<211> LENGTH: 136
<212> TYPE: PRT
<213> ORGANISM: Artificial sequence
<220> FEATURE:
<223> OTHER INFORMATION: Engineered sequence

<400> SEQUENCE: 296

Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
                 20                  25                  30

Val His Ala Ala Gly Leu Ile Glu Gly Glu Lys Val Ala Ile Val Asp
                 35                  40                  45

Ile Thr Asn Gly Ala Arg Leu Glu Thr Tyr Val Ile Val Gly Asp Ala
     50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ser Asp Asn
                100                 105                 110

Arg Ile Val Ala Leu Gly Asn Asp Leu Ala Glu Ala Leu Pro Gly Ser
                115                 120                 125

Gly Leu Leu Thr Ser Arg Ser Ile
    130                 135
```

<210> SEQ ID NO 297
<211> LENGTH: 408
<212> TYPE: DNA
<213> ORGANISM: Artificial sequence
<220> FEATURE:
<223> OTHER INFORMATION: Engineered sequence

<400> SEQUENCE: 297

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg cgaaccgca tcgttgccct gggcaatgat     360
ctggcggaag ccctgccggg tagcggtctg ctgacgagcc gtagtatt                  408
```

<210> SEQ ID NO 298
<211> LENGTH: 136
<212> TYPE: PRT
<213> ORGANISM: Artificial sequence
<220> FEATURE:
<223> OTHER INFORMATION: Engineered sequence

<400> SEQUENCE: 298

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Ala Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Ile
    130                 135
```

<210> SEQ ID NO 299
<211> LENGTH: 408
<212> TYPE: DNA
<213> ORGANISM: Artificial sequence
<220> FEATURE:
<223> OTHER INFORMATION: Engineered sequence

<400> SEQUENCE: 299

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
```

```
tacgaaccga aaattataca cgtgacggcg cagaaccgca tcgttgccct gggcaatgat    360
ctggcggaag ccctgccggg tagcggtctg ctgacgagcc gtagtatt                408
```

<210> SEQ ID NO 300
<211> LENGTH: 136
<212> TYPE: PRT
<213> ORGANISM: Artificial sequence
<220> FEATURE:
<223> OTHER INFORMATION: Engineered sequence

<400> SEQUENCE: 300

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Gln Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135
```

<210> SEQ ID NO 301
<211> LENGTH: 408
<212> TYPE: DNA
<213> ORGANISM: Artificial sequence
<220> FEATURE:
<223> OTHER INFORMATION: Engineered sequence

<400> SEQUENCE: 301

```
atgctgtaca ccatcctggg ttcaaaaatc catcgtgcaa cggtgacgca agttgacctg    60
gactatgtgg gttctgtcac gattgatgca gacctggtcc atgcagcagg tctgatcgaa   120
ggtgaaaaag ttgcaattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg gacaaccgca tcgttgccct gggcaatgat   360
ctggcggaaa cgctgccggg tagcggtctg ctgacgagcc gtagtatt                408
```

<210> SEQ ID NO 302
<211> LENGTH: 136
<212> TYPE: PRT
<213> ORGANISM: Artificial sequence
<220> FEATURE:
<223> OTHER INFORMATION: Engineered sequence

<400> SEQUENCE: 302

```
Met Leu Tyr Thr Ile Leu Gly Ser Lys Ile His Arg Ala Thr Val Thr
1               5                   10                  15
```

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Thr Leu Pro Gly Ser
        115                 120                 125

Gly Leu Leu Thr Ser Arg Ser Ile
    130                 135

<210> SEQ ID NO 303
<211> LENGTH: 408
<212> TYPE: DNA
<213> ORGANISM: Artificial sequence
<220> FEATURE:
<223> OTHER INFORMATION: Engineered sequence

<400> SEQUENCE: 303
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttgcagttgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtatt               408

<210> SEQ ID NO 304
<211> LENGTH: 136
<212> TYPE: PRT
<213> ORGANISM: Artificial sequence
<220> FEATURE:
<223> OTHER INFORMATION: Engineered sequence

<400> SEQUENCE: 304

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Val Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135

<210> SEQ ID NO 305
<211> LENGTH: 408
<212> TYPE: DNA
<213> ORGANISM: Artificial sequence
<220> FEATURE:
<223> OTHER INFORMATION: Engineered sequence

<400> SEQUENCE: 305
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg acaaccgca tcgttgccct gggcaatgat     360
ctggcggaag ccctgccggg tagcggtctg ctgacgagcc gtagtctt               408

<210> SEQ ID NO 306
<211> LENGTH: 136
<212> TYPE: PRT
<213> ORGANISM: Artificial sequence
<220> FEATURE:
<223> OTHER INFORMATION: Engineered sequence

<400> SEQUENCE: 306

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 307
<211> LENGTH: 408
<212> TYPE: DNA
<213> ORGANISM: Artificial sequence
<220> FEATURE:
<223> OTHER INFORMATION: Engineered sequence

<400> SEQUENCE: 307
atgctgtaca ccatcctggg ttcaaaaatc catcgtgcaa cggtgacgca agttgacctg      60

-continued

```
gactatgtgg gttctgtcac gattgatgca gacctggtcc atgcagcagg tctgcgtgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                  408
```

<210> SEQ ID NO 308
<211> LENGTH: 136
<212> TYPE: PRT
<213> ORGANISM: Artificial sequence
<220> FEATURE:
<223> OTHER INFORMATION: Engineered sequence

<400> SEQUENCE: 308

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 309
<211> LENGTH: 408
<212> TYPE: DNA
<213> ORGANISM: Artificial sequence
<220> FEATURE:
<223> OTHER INFORMATION: Engineered sequence

<400> SEQUENCE: 309

```
atgctgtaca ccatcctggg ttcaaaaatc catcgtgcaa cggtgacgca agttgacctg     60
aattatgtgg ttctgtcac gattgatgca gacctggtcc atgcagcagg tctgatcgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                  408
```

<210> SEQ ID NO 310
<211> LENGTH: 136
<212> TYPE: PRT
<213> ORGANISM: Artificial sequence
<220> FEATURE:

<223> OTHER INFORMATION: Engineered sequence

<400> SEQUENCE: 310

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 311
<211> LENGTH: 408
<212> TYPE: DNA
<213> ORGANISM: Artificial sequence
<220> FEATURE:
<223> OTHER INFORMATION: Engineered sequence

<400> SEQUENCE: 311
atgctgtaca ccatcctggg ttcaaaaatc catcgtgcaa cggtgacgca agttgacctg      60
aattatgtgg ttctgtcac gattgatgca gacctggtcc atgcagcagg tctgatcgaa      120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaag ccattccggg tagcggtctg ctgacgagcc gtagtctt                  408

<210> SEQ ID NO 312
<211> LENGTH: 136
<212> TYPE: PRT
<213> ORGANISM: Artificial sequence
<220> FEATURE:
<223> OTHER INFORMATION: Engineered sequence

<400> SEQUENCE: 312

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

```
Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Ala Ile Pro Gly Ser
        115                 120                 125

Gly Leu Leu Thr Ser Arg Ser Leu
    130                 135

<210> SEQ ID NO 313
<211> LENGTH: 408
<212> TYPE: DNA
<213> ORGANISM: Artificial sequence
<220> FEATURE:
<223> OTHER INFORMATION: Engineered sequence

<400> SEQUENCE: 313
atgctgtaca ccatcctggg ttcaaaaatc catcgtgcaa cggtgacgca agttgacctg      60
gactatgtgg ttctgtcac gattgatgca gacctggtcc atgcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaaa cgctgccggg tagcggtctg ctgacgagcc gtagtctt                  408

<210> SEQ ID NO 314
<211> LENGTH: 136
<212> TYPE: PRT
<213> ORGANISM: Artificial sequence
<220> FEATURE:
<223> OTHER INFORMATION: Engineered sequence

<400> SEQUENCE: 314

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Thr Leu Pro Gly Ser
        115                 120                 125

Gly Leu Leu Thr Ser Arg Ser Leu
    130                 135

<210> SEQ ID NO 315
<211> LENGTH: 408
<212> TYPE: DNA
<213> ORGANISM: Artificial sequence
```

<220> FEATURE:
<223> OTHER INFORMATION: Engineered sequence

<400> SEQUENCE: 315

```
atgctgtaca ccatcctggg ttcaaaaatc catcgtgcaa cggtgacgca agttgacctg    60
aattatgtgg ttctgtcac gattgatgca gacctggtcc atgcagcagg tctgcgtgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct ggcaatgat    360
ctgtctgaag ccctgccggg tagcggtctg ctgacgagcc gtagtctt              408
```

<210> SEQ ID NO 316
<211> LENGTH: 136
<212> TYPE: PRT
<213> ORGANISM: Artificial sequence
<220> FEATURE:
<223> OTHER INFORMATION: Engineered sequence

<400> SEQUENCE: 316

```
Met Leu Tyr Thr Ile Leu Gly Ser Lys Ile His Arg Ala Thr Val Thr
1               5                   10                  15
Gln Val Asp Leu Asn Tyr Val Gly Ser Val Thr Ile Asp Ala Asp Leu
            20                  25                  30
Val His Ala Ala Gly Leu Arg Glu Gly Glu Lys Val Gln Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ser Glu Ala Leu Pro Gly Ser
        115                 120                 125
Gly Leu Leu Thr Ser Arg Ser Leu
    130                 135
```

<210> SEQ ID NO 317
<211> LENGTH: 408
<212> TYPE: DNA
<213> ORGANISM: Artificial sequence
<220> FEATURE:
<223> OTHER INFORMATION: Engineered sequence

<400> SEQUENCE: 317

```
atgctgtaca ccatcctggg ttcaaaaatc catcgtgcaa cggtgacgca agttgacctg    60
aattatgtgg ttctgtcac gattgatgca gacctggtcc atgcagcagg tctgatcgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaaa cgctgccggg tagcggtctg ctgacgagcc gtagtctt              408
```

<210> SEQ ID NO 318
<211> LENGTH: 136
<212> TYPE: PRT
<213> ORGANISM: Artificial sequence
<220> FEATURE:
<223> OTHER INFORMATION: Engineered sequence

<400> SEQUENCE: 318

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Thr Leu Pro Gly Ser
        115                 120                 125

Gly Leu Leu Thr Ser Arg Ser Leu
    130                 135

<210> SEQ ID NO 319
<211> LENGTH: 408
<212> TYPE: DNA
<213> ORGANISM: Artificial sequence
<220> FEATURE:
<223> OTHER INFORMATION: Engineered sequence

<400> SEQUENCE: 319
atgctgtaca ccatcctggg ttcaaaaatc catcgtgcaa cggtgacgca agttgacctg      60
aattatgtgg ttctgtcac gattgatgca gacctggtcc atgcagcagg tctgatcgaa     120
ggtgaaaaag ttccaattgt cgatatcacc aacggcgctc gtctggaaac gtatgtgatt     180
gttggtgatg cgggcaccgg taacattttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaag cccttccggg tagcggtctg ctgacgagcc gtagtctt                  408

<210> SEQ ID NO 320
<211> LENGTH: 136
<212> TYPE: PRT
<213> ORGANISM: Artificial sequence
<220> FEATURE:
<223> OTHER INFORMATION: Engineered sequence

<400> SEQUENCE: 320

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Pro Ile Val Asp

```
                35                  40                  45
Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Ala Leu Pro Gly Ser
        115                 120                 125

Gly Leu Leu Thr Ser Arg Ser Leu
    130                 135

<210> SEQ ID NO 321
<211> LENGTH: 408
<212> TYPE: DNA
<213> ORGANISM: Artificial sequence
<220> FEATURE:
<223> OTHER INFORMATION: Engineered sequence

<400> SEQUENCE: 321
atgctgtaca ccatcctggg ttcaaaaatc catcgtgcaa cggtgacgca agttgacctg      60
gactatgtgg ttctgtcac gattgatgca gacctggtcc atgcagcagg tctgcgtgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccattccggg tagcggtctg ctgacgagcc gtagtctt               408

<210> SEQ ID NO 322
<211> LENGTH: 136
<212> TYPE: PRT
<213> ORGANISM: Artificial sequence
<220> FEATURE:
<223> OTHER INFORMATION: Engineered sequence

<400> SEQUENCE: 322

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Ile Pro Gly Ser
        115                 120                 125

Gly Leu Leu Thr Ser Arg Ser Leu
```

```
        130             135

<210> SEQ ID NO 323
<211> LENGTH: 408
<212> TYPE: DNA
<213> ORGANISM: Artificial sequence
<220> FEATURE:
<223> OTHER INFORMATION: Engineered sequence

<400> SEQUENCE: 323
atgctgtaca ccatcctggg ttcaaaaatc catcgtgcaa cggtgacgca agttgacctg      60
gactatgtgg gttctgtcac gattgatgca gacctggtcc atgcagcagg tctgcgtgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaag ccattccggg tagcggtctg ctgacgagcc gtagtctt                 408

<210> SEQ ID NO 324
<211> LENGTH: 136
<212> TYPE: PRT
<213> ORGANISM: Artificial sequence
<220> FEATURE:
<223> OTHER INFORMATION: Engineered sequence

<400> SEQUENCE: 324

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Ala Ile Pro Gly Ser
        115                 120                 125

Gly Leu Leu Thr Ser Arg Ser Leu
    130                 135

<210> SEQ ID NO 325
<211> LENGTH: 408
<212> TYPE: DNA
<213> ORGANISM: Artificial sequence
<220> FEATURE:
<223> OTHER INFORMATION: Engineered sequence

<400> SEQUENCE: 325
atgctgtaca ccatcctggg ttcaaaaatc catcgtgcaa cggtgacgca agttgacctg      60
aattatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
```

```
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctgtctgaaa cgattccggg tagcggtctg ctgacgagcc gtagtctt                 408
```

```
<210> SEQ ID NO 326
<211> LENGTH: 136
<212> TYPE: PRT
<213> ORGANISM: Artificial sequence
<220> FEATURE:
<223> OTHER INFORMATION: Engineered sequence

<400> SEQUENCE: 326
```

```
Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Thr Ile Pro Gly Ser
        115                 120                 125

Gly Leu Leu Thr Ser Arg Ser Leu
    130                 135
```

```
<210> SEQ ID NO 327
<211> LENGTH: 408
<212> TYPE: DNA
<213> ORGANISM: Artificial sequence
<220> FEATURE:
<223> OTHER INFORMATION: Engineered sequence

<400> SEQUENCE: 327
atgctgtaca ccatcctggg ttcaaaaatc catcgtgcaa cggtgacgca agttgacctg     60
aattatgtgg gttctgtcac gattgatgca gacctggtcc atgcagcagg tctgcgtgaa    120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctgtctgaag ccctgccggg tagcggtctg ctgacgagcc gtagtctt                 408
```

```
<210> SEQ ID NO 328
<211> LENGTH: 136
<212> TYPE: PRT
<213> ORGANISM: Artificial sequence
<220> FEATURE:
<223> OTHER INFORMATION: Engineered sequence

<400> SEQUENCE: 328
```

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Arg Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Ala Leu Pro Gly Ser
        115                 120                 125

Gly Leu Leu Thr Ser Arg Ser Leu
    130                 135

<210> SEQ ID NO 329
<211> LENGTH: 408
<212> TYPE: DNA
<213> ORGANISM: Artificial sequence
<220> FEATURE:
<223> OTHER INFORMATION: Engineered sequence

<400> SEQUENCE: 329
atgctgtaca ccatcctggg ttcaaaaatc catcgtgcaa cggtgacgca agttgacctg      60
aattatgtgg ttctgtcac gattgatgca gacctggtcc atgcagcagg tctgcgtgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaag ccattccggg tagcggtctg ctgacgagcc gtagtctt               408

<210> SEQ ID NO 330
<211> LENGTH: 136
<212> TYPE: PRT
<213> ORGANISM: Artificial sequence
<220> FEATURE:
<223> OTHER INFORMATION: Engineered sequence

<400> SEQUENCE: 330

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Arg Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ser Glu Ala Ile Pro Gly Ser
            115                 120                 125

Gly Leu Leu Thr Ser Arg Ser Leu
        130                 135

<210> SEQ ID NO 331
<211> LENGTH: 408
<212> TYPE: DNA
<213> ORGANISM: Artificial sequence
<220> FEATURE:
<223> OTHER INFORMATION: Engineered sequence

<400> SEQUENCE: 331
atgctgtaca ccatcctggg ttcaaaaatc catcgtgcaa cggtgacgca agttgacctg      60
gactatgtgg ttctgtcac gattgatgca gacctggtcc tggcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408

<210> SEQ ID NO 332
<211> LENGTH: 136
<212> TYPE: PRT
<213> ORGANISM: Artificial sequence
<220> FEATURE:
<223> OTHER INFORMATION: Engineered sequence

<400> SEQUENCE: 332

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val Leu Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
        130                 135

<210> SEQ ID NO 333
<211> LENGTH: 408
<212> TYPE: DNA
<213> ORGANISM: Artificial sequence
<220> FEATURE:
<223> OTHER INFORMATION: Engineered sequence

<400> SEQUENCE: 333

```
atgctgtaca ccatcctggg ttcaaaaatc catcgtgcaa cggtgacgca agttgacctg     60
gactatgtgg gttctgtcac gattgatgca gacctggtcc tggcagcagg tctgatcgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattgtaca cgtgacggcg gacaaccgca tcgttgccct gggcaatgat    360
ctggcggaag ccctgccggg tagcggtctg ctgacgagcc gtagtctt                 408
```

<210> SEQ ID NO 334
<211> LENGTH: 136
<212> TYPE: PRT
<213> ORGANISM: Artificial sequence
<220> FEATURE:
<223> OTHER INFORMATION: Engineered sequence

<400> SEQUENCE: 334

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val Leu Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 335
<211> LENGTH: 408
<212> TYPE: DNA
<213> ORGANISM: Artificial sequence
<220> FEATURE:
<223> OTHER INFORMATION: Engineered sequence

<400> SEQUENCE: 335

```
atgctgtaca ccatcctggg ttcaaaaatc catcgtgcaa cggtgacgca agttgacctg     60
gactatgtgg gttctgtcac gattgatgca gacctggtcc atgcagcagg tctgatcgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattatca cgtgacggcg cagaaccgca tcgttgccct gggcaatgat    360
ctggcggaag ccctgccggg tagcggtctg ctgacgagcc gtagtctt                 408
```

<210> SEQ ID NO 336
<211> LENGTH: 136

```
<212> TYPE: PRT
<213> ORGANISM: Artificial sequence
<220> FEATURE:
<223> OTHER INFORMATION: Engineered sequence

<400> SEQUENCE: 336

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Gln Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 337
<211> LENGTH: 408
<212> TYPE: DNA
<213> ORGANISM: Artificial sequence
<220> FEATURE:
<223> OTHER INFORMATION: Engineered sequence

<400> SEQUENCE: 337
atgctgtaca ccatcctggg ttcaaaaatc catcgtgcaa cggtgacgca agttgacctg      60
gactatgtgg gttctgtcac gattgatgca gacctgattc atgcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408

<210> SEQ ID NO 338
<211> LENGTH: 136
<212> TYPE: PRT
<213> ORGANISM: Artificial sequence
<220> FEATURE:
<223> OTHER INFORMATION: Engineered sequence

<400> SEQUENCE: 338

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Ile His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60
```

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 339
<211> LENGTH: 408
<212> TYPE: DNA
<213> ORGANISM: Artificial sequence
<220> FEATURE:
<223> OTHER INFORMATION: Engineered sequence

<400> SEQUENCE: 339
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcttgtta cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408

<210> SEQ ID NO 340
<211> LENGTH: 136
<212> TYPE: PRT
<213> ORGANISM: Artificial sequence
<220> FEATURE:
<223> OTHER INFORMATION: Engineered sequence

<400> SEQUENCE: 340

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Leu Val Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 341

<211> LENGTH: 408
<212> TYPE: DNA
<213> ORGANISM: Artificial sequence
<220> FEATURE:
<223> OTHER INFORMATION: Engineered sequence

<400> SEQUENCE: 341

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggtta cggacgccga agcaaaggca     300
tacgaaccga aaattataca cgtgacggcg acaaccgca tcgttgccct gggcaatgat      360
ctggcggaag ccctgccggg tagcggtctg ctgacgagcc gtagtctt                  408
```

<210> SEQ ID NO 342
<211> LENGTH: 136
<212> TYPE: PRT
<213> ORGANISM: Artificial sequence
<220> FEATURE:
<223> OTHER INFORMATION: Engineered sequence

<400> SEQUENCE: 342

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Val Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Leu
    130                 135
```

<210> SEQ ID NO 343
<211> LENGTH: 408
<212> TYPE: DNA
<213> ORGANISM: Artificial sequence
<220> FEATURE:
<223> OTHER INFORMATION: Engineered sequence

<400> SEQUENCE: 343

```
atgctgtaca ccatcctggg ttcaaaaatc catcgtgcaa cggtgacgca agttgacctg      60
gactatgtgg ttctgtcac gattgatgca gacctggtct atgcagcagg tctgatcgaa      120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
```

```
tacgaaccga aaattataca cgtgacggcg gacaaccgca tcgttgccct gggcaatgat    360
ctggcggaag ccctgccggg tagcggtctg ctgacgagcc gtagtctt               408
```

<210> SEQ ID NO 344
<211> LENGTH: 136
<212> TYPE: PRT
<213> ORGANISM: Artificial sequence
<220> FEATURE:
<223> OTHER INFORMATION: Engineered sequence

<400> SEQUENCE: 344

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val Tyr Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 345
<211> LENGTH: 408
<212> TYPE: DNA
<213> ORGANISM: Artificial sequence
<220> FEATURE:
<223> OTHER INFORMATION: Engineered sequence

<400> SEQUENCE: 345

```
atgctgtaca ccatcctggg ttcaaaaatc catcgtgcaa cggtgacgca agttgacctg     60
gactatgtgg gttctgtcac gattgatgca gacctggtca tggcagcagg tctgatcgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                408
```

<210> SEQ ID NO 346
<211> LENGTH: 136
<212> TYPE: PRT
<213> ORGANISM: Artificial sequence
<220> FEATURE:
<223> OTHER INFORMATION: Engineered sequence

<400> SEQUENCE: 346

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
```

```
            20                  25                  30
Val Met Ala Ala Gly Leu Ile Glu Gly Glu Lys Val Gln Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
            130             135
```

<210> SEQ ID NO 347
<211> LENGTH: 408
<212> TYPE: DNA
<213> ORGANISM: Artificial sequence
<220> FEATURE:
<223> OTHER INFORMATION: Engineered sequence

<400> SEQUENCE: 347

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttcaggttgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 348
<211> LENGTH: 136
<212> TYPE: PRT
<213> ORGANISM: Artificial sequence
<220> FEATURE:
<223> OTHER INFORMATION: Engineered sequence

<400> SEQUENCE: 348

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Val Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
```

115                 120                 125
Gly Leu Leu Thr Ser Arg Ser Leu
    130                 135

<210> SEQ ID NO 349
<211> LENGTH: 408
<212> TYPE: DNA
<213> ORGANISM: Artificial sequence
<220> FEATURE:
<223> OTHER INFORMATION: Engineered sequence

<400> SEQUENCE: 349
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccgcg tagcggtctg ctgacgagcc gtagtctt              408

<210> SEQ ID NO 350
<211> LENGTH: 136
<212> TYPE: PRT
<213> ORGANISM: Artificial sequence
<220> FEATURE:
<223> OTHER INFORMATION: Engineered sequence

<400> SEQUENCE: 350

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
            85                  90                  95

Glu Ala Lys Ala Tyr Glu Pro Lys Ile Ile His Val Thr Ala Asp Asn
        100                 105                 110

Arg Ile Val Ala Leu Gly Asn Asp Leu Ala Glu Ala Leu Pro Arg Ser
    115                 120                 125

Gly Leu Leu Thr Ser Arg Ser Leu
    130                 135

<210> SEQ ID NO 351
<211> LENGTH: 408
<212> TYPE: DNA
<213> ORGANISM: Artificial sequence
<220> FEATURE:
<223> OTHER INFORMATION: Engineered sequence

<400> SEQUENCE: 351
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120

```
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg acaaccgca tcgttgccct gggcaatgat    360
ctggcggaag ccctgccgtt tagcggtctg ctgacgagcc gtagtctt                 408
```

<210> SEQ ID NO 352
<211> LENGTH: 136
<212> TYPE: PRT
<213> ORGANISM: Artificial sequence
<220> FEATURE:
<223> OTHER INFORMATION: Engineered sequence

<400> SEQUENCE: 352

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Phe Ser
        115                 120                 125

Gly Leu Leu Thr Ser Arg Ser Leu
    130                 135
```

<210> SEQ ID NO 353
<211> LENGTH: 408
<212> TYPE: DNA
<213> ORGANISM: Artificial sequence
<220> FEATURE:
<223> OTHER INFORMATION: Engineered sequence

<400> SEQUENCE: 353

```
atgctgtaca ccatcctggg ttcaaaaatc catcgtgcaa cggtgacgca agttgacctg     60
aattatgtgg ttctgtcac gattgatgca gacctggtcc atgcagcagg tctgcgtgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggca    300
tacgaaccga aaattataca cgtgacggcg acaaccgca tcgttgccct gggcaatgat    360
ctggcggaag ccattccggg tagcggtctg ctgacgagcc gtagtctt                 408
```

<210> SEQ ID NO 354
<211> LENGTH: 136
<212> TYPE: PRT
<213> ORGANISM: Artificial sequence
<220> FEATURE:
<223> OTHER INFORMATION: Engineered sequence

<400> SEQUENCE: 354

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Ile Pro Gly Ser
        115                 120                 125

Gly Leu Leu Thr Ser Arg Ser Leu
    130                 135

<210> SEQ ID NO 355
<211> LENGTH: 408
<212> TYPE: DNA
<213> ORGANISM: Artificial sequence
<220> FEATURE:
<223> OTHER INFORMATION: Engineered sequence

<400> SEQUENCE: 355
atgctgtaca ccatcctggg ttcaaaaatc catcgtgcaa cggtgacgca agttgacctg      60
aattatgtgg ttctgtcac gattgatgca gacctggtcc atgcagcagg tctgatcgaa      120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctgtctgaaa cgctgccggg tagcggtctg ctgacgagcc gtagtctt                  408

<210> SEQ ID NO 356
<211> LENGTH: 136
<212> TYPE: PRT
<213> ORGANISM: Artificial sequence
<220> FEATURE:
<223> OTHER INFORMATION: Engineered sequence

<400> SEQUENCE: 356

Met Leu Tyr Thr Ile Leu Gly Ser Lys Ile His Arg Ala Thr Val Thr
1               5                   10                  15

Gln Val Asp Leu Asn Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

-continued

```
Pro Gly Asp Leu Val Ile Ile Met Ser Tyr Leu Gln Ala Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ser Glu Thr Leu Pro Gly Ser
        115                 120                 125

Gly Leu Leu Thr Ser Arg Ser Leu
    130                 135

<210> SEQ ID NO 357
<211> LENGTH: 408
<212> TYPE: DNA
<213> ORGANISM: Artificial sequence
<220> FEATURE:
<223> OTHER INFORMATION: Engineered sequence

<400> SEQUENCE: 357
atgctgtaca ccatcctggg ttcaaaaatc catcgtgcaa cggtgacgca agttgacctg      60
gactatgtgg gttctgtcac gattgatgca gacctgattc atgcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcttgcca cggacgccga agcaaaggca     300
tacgaaccga aaattataca cgttacggcg gacaaccgat cgttgccct gggcaatgat      360 ctggcggaag ccctgccggg tagcggtctg ctgacgagcc gtagtctt                  408

<210> SEQ ID NO 358
<211> LENGTH: 136
<212> TYPE: PRT
<213> ORGANISM: Artificial sequence
<220> FEATURE:
<223> OTHER INFORMATION: Engineered sequence

<400> SEQUENCE: 358

Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Ile His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Leu Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 359
<211> LENGTH: 408
<212> TYPE: DNA
<213> ORGANISM: Artificial sequence
<220> FEATURE:
```

<223> OTHER INFORMATION: Engineered sequence

<400> SEQUENCE: 359

```
atgctgtaca ccatcctggg ttcaaaaatc catcgtgcaa cggtgacgca agttgacctg      60
gactatgtgg gttctgtcac gattgatgca gacctggtcc atgcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat tatcttgcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 360
<211> LENGTH: 136
<212> TYPE: PRT
<213> ORGANISM: Artificial sequence
<220> FEATURE:
<223> OTHER INFORMATION: Engineered sequence

<400> SEQUENCE: 360

```
Met Leu Tyr Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Arg Glu Gly Glu Lys Val Gln Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Tyr Leu Ala Thr Asp Ala
                85                  90                  95
Glu Ala Lys Ala Tyr Glu Pro Lys Ile Ile His Val Thr Ala Asp Asn
            100                 105                 110
Arg Ile Val Ala Leu Gly Asn Asp Leu Ala Glu Ala Leu Pro Gly Ser
        115                 120                 125
Gly Leu Leu Thr Ser Arg Ser Leu
    130                 135
```

<210> SEQ ID NO 361
<211> LENGTH: 408
<212> TYPE: DNA
<213> ORGANISM: Artificial sequence
<220> FEATURE:
<223> OTHER INFORMATION: Engineered sequence

<400> SEQUENCE: 361

```
atgctgtaca ccatcctggg ttcaaaaatc catcgtgcaa cggtgacgca agttgacctg      60
gactatgtgg gttctgtcac gattgatgca gacctgattc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 362
<211> LENGTH: 136
<212> TYPE: PRT
<213> ORGANISM: Artificial sequence
<220> FEATURE:
<223> OTHER INFORMATION: Engineered sequence

<400> SEQUENCE: 362

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Ile His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 363
<211> LENGTH: 408
<212> TYPE: DNA
<213> ORGANISM: Artificial sequence
<220> FEATURE:
<223> OTHER INFORMATION: Engineered sequence

<400> SEQUENCE: 363

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat tatcttgcca cggacgccga agcaaaggca     300
tacgaaccga aaattataca cgtgacggcg cagaaccgca tcgttgccct gggcaatgat     360
ctggcggaag ccctgccggg tagcggtctg ctgacgagcc gtagtctt               408
```

<210> SEQ ID NO 364
<211> LENGTH: 136
<212> TYPE: PRT
<213> ORGANISM: Artificial sequence
<220> FEATURE:
<223> OTHER INFORMATION: Engineered sequence

<400> SEQUENCE: 364

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45
```

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Tyr Leu Ala Thr Asp Ala
                     85                  90                  95

Glu Ala Lys Ala Tyr Glu Pro Lys Ile Ile His Val Thr Ala Gln Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
            130                 135

<210> SEQ ID NO 365
<211> LENGTH: 408
<212> TYPE: DNA
<213> ORGANISM: Artificial sequence
<220> FEATURE:
<223> OTHER INFORMATION: Engineered sequence

<400> SEQUENCE: 365
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat tatcaggcca cggacgccga agcaaaggca     300
tacgaaccga aaattataca cgtgacggcg acaaccgca tcgttgccct gggcaatgat     360
ctggcggaag ccctgccggg tagcggtctg ctgacgagcc gtagtctt             408

<210> SEQ ID NO 366
<211> LENGTH: 136
<212> TYPE: PRT
<213> ORGANISM: Artificial sequence
<220> FEATURE:
<223> OTHER INFORMATION: Engineered sequence

<400> SEQUENCE: 366

Met Leu Tyr Thr Ile Leu Gly Ser Lys Ile His Arg Ala Thr Val Thr
  1               5                  10                  15

Gln Val Asp Leu Asp Tyr Val Gly Ser Val Thr Ile Asp Ala Asp Leu
             20                  25                  30

Val His Ala Ala Gly Leu Ile Glu Gly Glu Lys Val Gln Ile Val Asp
         35                  40                  45

Ile Thr Asn Gly Ala Arg Leu Glu Thr Tyr Val Ile Val Gly Asp Ala
 50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Tyr Gln Ala Thr Asp Ala
                     85                  90                  95

Glu Ala Lys Ala Tyr Glu Pro Lys Ile Ile His Val Thr Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Leu
            130                 135

<210> SEQ ID NO 367
<211> LENGTH: 408
<212> TYPE: DNA
<213> ORGANISM: Artificial sequence
<220> FEATURE:
<223> OTHER INFORMATION: Engineered sequence

<400> SEQUENCE: 367

```
atgctgtaca ccatcctggg ttcaaaaatc catcgtgcaa cggtgacgca agttgacctg      60
gactatgtgg gttctgtcac gattgatgca gacctggtcc tggcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggtta cggacgccga agcaaaggca     300
tacgaaccga aaattataca cgtgacggcg acaaccgca tcgttgccct gggcaatgat      360
ctggcggaag ccctgccggg tagcggtctg ctgacgagcc gtagtctt                  408
```

<210> SEQ ID NO 368
<211> LENGTH: 136
<212> TYPE: PRT
<213> ORGANISM: Artificial sequence
<220> FEATURE:
<223> OTHER INFORMATION: Engineered sequence

<400> SEQUENCE: 368

```
Met Leu Tyr Thr Ile Leu Gly Ser Lys Ile His Arg Ala Thr Val Thr
1               5                  10                  15

Gln Val Asp Leu Asp Tyr Val Gly Ser Val Thr Ile Asp Ala Asp Leu
            20                  25                  30

Val Leu Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Val Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 369
<211> LENGTH: 408
<212> TYPE: DNA
<213> ORGANISM: Artificial sequence
<220> FEATURE:
<223> OTHER INFORMATION: Engineered sequence

<400> SEQUENCE: 369

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
```

```
ccgggtgatc tggtgattat catgagctat ctggttgcca cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                 408
```

<210> SEQ ID NO 370
<211> LENGTH: 136
<212> TYPE: PRT
<213> ORGANISM: Artificial sequence
<220> FEATURE:
<223> OTHER INFORMATION: Engineered sequence

<400> SEQUENCE: 370

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Val Ala Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 371
<211> LENGTH: 408
<212> TYPE: DNA
<213> ORGANISM: Artificial sequence
<220> FEATURE:
<223> OTHER INFORMATION: Engineered sequence

<400> SEQUENCE: 371

```
atgctgtaca ccatcctggg ttcaaaaatc catcgtgcaa cggtgacgca agttgacctg     60
gactatgtgg ttctgtcac gattgatgca gacctgattc atgcagcagg tctgcgtgaa    120
ggtgaaaaag ttcagattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggtta cggacgccga agcaaaggca    300
tacgaaccga aaattataca cgtgacggcg gacaaccgca tcgttgccct gggcaatgat    360
ctggcggaag ccctgccggg tagcggtctg ctgacgagcc gtagtctt                 408
```

<210> SEQ ID NO 372
<211> LENGTH: 136
<212> TYPE: PRT
<213> ORGANISM: Artificial sequence
<220> FEATURE:
<223> OTHER INFORMATION: Engineered sequence

<400> SEQUENCE: 372

Met Leu Tyr Thr Ile Leu Gly Ser Lys Ile His Arg Ala Thr Val Thr

```
                1               5                  10                  15
            Gln Val Asp Leu Asp Tyr Val Gly Ser Val Thr Ile Asp Ala Asp Leu
                            20                  25                  30

Ile His Ala Ala Gly Leu Arg Glu Gly Glu Lys Val Gln Ile Val Asp
                            35                  40                  45

Ile Thr Asn Gly Ala Arg Leu Glu Thr Tyr Val Ile Val Gly Asp Ala
                 50                  55                  60

Gly Thr Gly Asn Ile Cys Ile Asn Gly Ala Ala His Leu Ile Asn
             65                  70                  75                  80

Pro Gly Asp Leu Val Ile Ile Met Ser Tyr Leu Gln Val Thr Asp Ala
                             85                  90                  95

Glu Ala Lys Ala Tyr Glu Pro Lys Ile Ile His Val Thr Ala Asp Asn
                           100                 105                 110

Arg Ile Val Ala Leu Gly Asn Asp Leu Ala Glu Ala Leu Pro Gly Ser
                           115                 120                 125

Gly Leu Leu Thr Ser Arg Ser Leu
                           130                 135
```

<210> SEQ ID NO 373
<211> LENGTH: 408
<212> TYPE: DNA
<213> ORGANISM: Artificial sequence
<220> FEATURE:
<223> OTHER INFORMATION: Engineered sequence

<400> SEQUENCE: 373

```
atgctgtaca ccatcctggg ttcaaaaatc catcgtgcaa cggtgacgca agttgacctg      60
gactatgtgg gttctgtcac gattgatgca gacctggtcc atgcagcagg tctgcgtgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcttgtta cggacgccga agcaaaggca     300
tacgaaccga gtattataca cgtgacggcg gacaaccgca tcgttgccct gggcaatgat     360
ctggcggaag ccctgccggg tagcggtctg ctgacgagcc gtagtctt                  408
```

<210> SEQ ID NO 374
<211> LENGTH: 136
<212> TYPE: PRT
<213> ORGANISM: Artificial sequence
<220> FEATURE:
<223> OTHER INFORMATION: Engineered sequence

<400> SEQUENCE: 374

```
            Met Leu Tyr Thr Ile Leu Gly Ser Lys Ile His Arg Ala Thr Val Thr
             1               5                  10                  15

Gln Val Asp Leu Asp Tyr Val Gly Ser Val Thr Ile Asp Ala Asp Leu
                            20                  25                  30

Val His Ala Ala Gly Leu Arg Glu Gly Glu Lys Val Gln Ile Val Asp
                            35                  40                  45

Ile Thr Asn Gly Ala Arg Leu Glu Thr Tyr Val Ile Val Gly Asp Ala
                 50                  55                  60

Gly Thr Gly Asn Ile Cys Ile Asn Gly Ala Ala His Leu Ile Asn
             65                  70                  75                  80

Pro Gly Asp Leu Val Ile Ile Met Ser Tyr Leu Leu Val Thr Asp Ala
                             85                  90                  95

Glu Ala Lys Ala Tyr Glu Pro Ser Ile Ile His Val Thr Ala Asp Asn
```

```
                100               105               110
Arg Ile Val Ala Leu Gly Asn Asp Leu Ala Glu Ala Leu Pro Gly Ser
            115               120               125

Gly Leu Leu Thr Ser Arg Ser Leu
        130               135
```

<210> SEQ ID NO 375
<211> LENGTH: 408
<212> TYPE: DNA
<213> ORGANISM: Artificial sequence
<220> FEATURE:
<223> OTHER INFORMATION: Engineered sequence

<400> SEQUENCE: 375

```
atgctgtaca ccatcctggg ttcaaaaatc catcgtgcaa cggtgacgca agttgacctg      60
gactatgtgg gttctgtcac gattgatgca gacctggtcc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat tatcttgtta cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt                  408
```

<210> SEQ ID NO 376
<211> LENGTH: 136
<212> TYPE: PRT
<213> ORGANISM: Artificial sequence
<220> FEATURE:
<223> OTHER INFORMATION: Engineered sequence

<400> SEQUENCE: 376

```
Met Leu Tyr Thr Ile Leu Gly Ser Lys Ile His Arg Ala Thr Val Thr
1               5                  10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Tyr Leu Val Thr Asp Ala
                85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 377
<211> LENGTH: 408
<212> TYPE: DNA
<213> ORGANISM: Artificial sequence
<220> FEATURE:
<223> OTHER INFORMATION: Engineered sequence

<400> SEQUENCE: 377

```
atgctgtaca ccatcctggg ttcaaaaatc catcgtgcaa cggtgacgca agttgacctg    60
gactatgtgg ttctgtcac gattgatgca gacctggtcc atgcagcagg tctgcgtgaa   120
ggtgaaaaag ttcagattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcaggcca cggacgccga agcaaaggca   300
tacgaaccga aaattataca cgtgacggcg cagaaccgca tcgttgccct gggcaatgat   360
ctggcggaag ccctgccggg tagcggtctg ctgacgagcc gtagtctt              408
```

<210> SEQ ID NO 378
<211> LENGTH: 136
<212> TYPE: PRT
<213> ORGANISM: Artificial sequence
<220> FEATURE:
<223> OTHER INFORMATION: Engineered sequence

<400> SEQUENCE: 378

```
Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
            20                  25                  30

Val His Ala Ala Gly Leu Arg Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Ile His Val Thr Ala Gln Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 379
<211> LENGTH: 408
<212> TYPE: DNA
<213> ORGANISM: Artificial sequence
<220> FEATURE:
<223> OTHER INFORMATION: Engineered sequence

<400> SEQUENCE: 379

```
atgctgtaca ccatcctggg ttcaaaaatc catcgtgcaa cggtgacgca agttgacctg    60
gactatgtgg ttctgtcac gattgatgca gacctggtcc atgcagcagg tctgatcgaa   120
ggtgaaaaag ttcagattgt cgatatcacc aacggcgctc gtctggaaac gtatgtgatt   180
gttggtgatg cgggcaccgg taacatttgc atcaatggcg cagctgcgca tctgatcaat   240
ccgggtgatc tggtgattat catgagctat ctgcttgcca cggacgccga agcaaaggca   300
tacgaaccga aaattataca cgtgacggcg cggaaccgca tcgttgccct gggcaatgat   360
ctggcggaag ccctgccggg tagcggtctg ctgacgagcc gtagtctt              408
```

<210> SEQ ID NO 380
<211> LENGTH: 136
<212> TYPE: PRT

<213> ORGANISM: Artificial sequence
<220> FEATURE:
<223> OTHER INFORMATION: Engineered sequence

<400> SEQUENCE: 380

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Leu Ala Thr Asp Ala
                85                  90                  95

Glu Ala Lys Ala Tyr Glu Pro Lys Ile Ile His Val Thr Ala Arg Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135
```

<210> SEQ ID NO 381
<211> LENGTH: 408
<212> TYPE: DNA
<213> ORGANISM: Artificial sequence
<220> FEATURE:
<223> OTHER INFORMATION: Engineered sequence

<400> SEQUENCE: 381

```
atgctgtaca ccatcctggg ttcaaaaatc catcgtgcaa cggtgacgca agttgacctg      60
gactatgtgg gttctgtcac gattgatgca gacctgattc atgcagcagg tctgatcgaa     120
ggtgaaaaag ttcagattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggtta cggacgccga agcaaaggca     300
tacgaaccga aaattataca cgtgacggcg gacaaccgca tcgttgccct gggcaatgat     360
ctggcggaag ccctgccggg tagcggtctg ctgacgagcc gtagtctt               408
```

<210> SEQ ID NO 382
<211> LENGTH: 136
<212> TYPE: PRT
<213> ORGANISM: Artificial sequence
<220> FEATURE:
<223> OTHER INFORMATION: Engineered sequence

<400> SEQUENCE: 382

```
Met Leu Tyr Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Ile His Ala Ala Gly Leu Ile Glu Gly Glu Lys Val Gln Ile Val Asp
        35                  40                  45

Ile Thr Asn Gly Ala Arg Leu Glu Thr Tyr Val Ile Val Gly Asp Ala
    50                  55                  60
```

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Gln Val Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 383
<211> LENGTH: 408
<212> TYPE: DNA
<213> ORGANISM: Artificial sequence
<220> FEATURE:
<223> OTHER INFORMATION: Engineered sequence

<400> SEQUENCE: 383

```
atgctgtaca ccatcctggg ttcaaaaatc catcgtgcaa cggtgacgca agttgacctg      60
gactatgtgg ttctgtcac gattgatgca gacctggtcc atgcagcagg tctgatcgaa      120
ggtgaaaaag ttcagattgt cgatatcacc aacggcgctc gtctggaaac gtatgtgatt      180
gttggtgatg cgggcaccgg taacatttgc atcaatggcg cagctgcgca tctgatcaat      240
ccgggtgatc tggtgattat catgagctat ctgcttgtta cggacgccga agcaaaggca      300
tacgaaccga aaattataca cgtgacggcg acaaccgca tcgttgccct gggcaatgat      360
ctggcggaag ccctgccggg tagcggtctg ctgacgagcc gtagtctt                  408
```

<210> SEQ ID NO 384
<211> LENGTH: 136
<212> TYPE: PRT
<213> ORGANISM: Artificial sequence
<220> FEATURE:
<223> OTHER INFORMATION: Engineered sequence

<400> SEQUENCE: 384

Met Leu Tyr Thr Ile Leu Gly Ser Lys Ile His Arg Ala Thr Val Thr
 1               5                  10                  15

Gln Val Asp Leu Asp Tyr Val Gly Ser Val Thr Ile Asp Ala Asp Leu
                20                  25                  30

Val His Ala Ala Gly Leu Ile Glu Gly Glu Lys Val Gln Ile Val Asp
            35                  40                  45

Ile Thr Asn Gly Ala Arg Leu Glu Thr Tyr Val Ile Val Gly Asp Ala
        50                  55                  60

Gly Thr Gly Asn Ile Cys Ile Asn Gly Ala Ala His Leu Ile Asn
 65                  70                  75                  80

Pro Gly Asp Leu Val Ile Ile Met Ser Tyr Leu Leu Val Thr Asp Ala
                 85                  90                  95

Glu Ala Lys Ala Tyr Glu Pro Lys Ile Ile His Val Thr Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Leu
    130                 135

<210> SEQ ID NO 385
<211> LENGTH: 354

<212> TYPE: DNA
<213> ORGANISM: Artificial sequence
<220> FEATURE:
<223> OTHER INFORMATION: Engineered sequence

<400> SEQUENCE: 385

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttgccct gggc            354
```

<210> SEQ ID NO 386
<211> LENGTH: 118
<212> TYPE: PRT
<213> ORGANISM: Artificial sequence
<220> FEATURE:
<223> OTHER INFORMATION: Engineered sequence

<400> SEQUENCE: 386

```
Met Leu Arg Thr Ile Leu Gly Ser Lys Ile His Arg Ala Thr Val Thr
1               5                   10                  15
Gln Val Asp Leu Asp Tyr Val Gly Ser Val Thr Ile Asp Ala Asp Leu
            20                  25                  30
Val His Ala Ala Gly Leu Ile Glu Gly Glu Lys Val Ala Ile Val Asp
        35                  40                  45
Ile Thr Asn Gly Ala Arg Leu Glu Thr Tyr Val Ile Val Gly Asp Ala
    50                  55                  60
Gly Thr Gly Asn Ile Cys Ile Asn Gly Ala Ala Ala His Leu Ile Asn
65                  70                  75                  80
Pro Gly Asp Leu Val Ile Ile Met Ser Tyr Leu Gln Ala Thr Asp Ala
                85                  90                  95
Glu Ala Lys Ala Tyr Glu Pro Lys Ile Val His Val Asp Ala Asp Asn
            100                 105                 110
Arg Ile Val Ala Leu Gly
        115
```

<210> SEQ ID NO 387
<211> LENGTH: 375
<212> TYPE: DNA
<213> ORGANISM: Artificial sequence
<220> FEATURE:
<223> OTHER INFORMATION: Engineered sequence

<400> SEQUENCE: 387

```
atgctgcgta ccatcctggg ttcaaaaatc catcgtgcaa cggtgacgca agttgacctg      60
gactatgtgg ttctgtcac cattgatgca gacctggtcc atgcagcagg tctgatcgaa      120
ggtgaaaaag ttgcaattgt cgatatcacc aacggcgctc gtctggaaac gtatgtgatt    180
gttggtgatg cgggcaccgg taacatttgc atcaatggcg cagctgcgca tctgatcaat    240
ccgggtgatc tggtgattat catgagctat ctgcaggcca cggacgccga agcaaaggct    300
tacgaaccga aaattgtcca cgtggatgcg gacaaccgca tcgttgccct gggcaatgat    360
ctggcggaag ccctg                                                        375
```

<210> SEQ ID NO 388
<211> LENGTH: 125
<212> TYPE: PRT
<213> ORGANISM: Artificial sequence
<220> FEATURE:
<223> OTHER INFORMATION: Engineered sequence

<400> SEQUENCE: 388

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu
        115                 120                 125

<210> SEQ ID NO 389
<211> LENGTH: 390
<212> TYPE: DNA
<213> ORGANISM: Artificial sequence
<220> FEATURE:
<223> OTHER INFORMATION: Engineered sequence

<400> SEQUENCE: 389
atgctgcgta ccatcctggg ttcaaaaatc catcgtgcaa cggtgacgca agttgacctg      60
gactatgtgg gttctgtcac cattgatgca gacctggtcc atgcagcagg tctgatcgaa     120
ggtgaaaaag ttgcaattgt cgatatcacc aacggcgctc gtctggaaac gtatgtgatt     180
gttggtgatg cgggcaccgg taacatttgc atcaatggcg cagctgcgca tctgatcaat     240
ccgggtgatc tggtgattat catgagctat ctgcaggcca cggacgccga agcaaaggct     300
tacgaaccga aaattgtcca cgtggatgcg gacaaccgca tcgttgccct gggcaatgat     360
ctggcggaag ccctgccggg tagcggtctg                                      390

<210> SEQ ID NO 390
<211> LENGTH: 130
<212> TYPE: PRT
<213> ORGANISM: Artificial sequence
<220> FEATURE:
<223> OTHER INFORMATION: Engineered sequence

<400> SEQUENCE: 390

Met Leu Arg Thr Ile Leu Gly Ser Lys Ile His Arg Ala Thr Val Thr
1               5                   10                  15

Gln Val Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

-continued

```
Gly Thr Gly Asn Ile Cys Ile Asn Gly Ala Ala Ala His Leu Ile Asn
65                  70                  75                  80

Pro Gly Asp Leu Val Ile Ile Met Ser Tyr Leu Gln Ala Thr Asp Ala
            85                  90                  95

Glu Ala Lys Ala Tyr Glu Pro Lys Ile Val His Val Asp Ala Asp Asn
            100             105                 110

Arg Ile Val Ala Leu Gly Asn Asp Leu Ala Glu Ala Leu Pro Gly Ser
        115                 120                 125

Gly Leu
    130
```

ENGINEERED DECARBOXYLASE POLYPEPTIDES AND THEIR APPLICATION IN PREPARING BETA-ALANINE

PRIORITY

This application corresponds to the U.S. National phase of International Application No. PCT/CN2018/108478, filed Sep. 28, 2018, which, in turn, claims priority to Chinese Patent Application No. 2017 10924714.5 filed Oct. 1, 2017, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Feb. 21, 2020, is named LNK_212US_SEQ_LIST_TXT.txt and is 377,943 bytes in size.

TECHNICAL FIELD OF THE PRESENT INVENTION

The invention relates to the field of bioengineering technology, and particularly relates to sequences of an engineered decarboxylase for producing β-alanine, and its preparation method and reaction process.

BACKGROUND OF THE PRESENT INVENTION

β-alanine, also known as β-aminopropionic acid, was discovered in 1972 by Ross and Monroe in uracil degradation products. It is a non-proteinogenic amino acid and the only beta-type amino acid found in nature. The main physiological activity of β-alanine is the synthesis of pantothenic acid and coenzyme A which are involved in the metabolism of proteins, fats and sugars. It is also involved in synthesis of carnosine and promoting the formation of antibodies in the body, and exerts biological functions such as antioxidation and reduction of immune response. Modern medical research has found that, in the mammalian nervous system, β-alanine acts as a neurotransmitter in the brain, an activator of ion channels, and can also treat liver damage caused by tissue hypoxia. In the field of fine chemicals, β-alanine is used for the synthesis of poly(β-alanine), plating buffers, dyes, etc. In the pharmaceutical industry, β-alanine can be used as an intermediate in many drugs, such as calcium pantothenate, a vitamin B group, and is a component of coenzyme A necessary for various metabolisms. In addition, N-(2,5-II Chloro-4-cyanothiobenzene)-β-alanine is an effective antifungal agent. So β-alanine has a wide range of applications and market prospects.

β-alanine can be obtained by hydrolysis and refining of sericin, gelatin, zein and the like, but the source of such raw materials is limited and the cost is high. Currently, β-alanine is mainly produced by chemical methods in the industry, including: (1) acrylonitrile method; (2) acrylic acid method; (3) succinimide (succinimide) degradation method; (4) β-aminopropionitrile method. However, using chemical methods are prone to produce polluting gases, and some reaction are done under conditions of high temperature and high pressure, producing toxic by-products, which results in difficulty in purification process.

Compared with the chemical method, the enzymatic method for producing 3-alanine has the characteristics of simple process, convenient purification and pollution-free. It has become a hot research topic in recent years, but the enzymatic conversion reported so far suffers from low enzyme activity, low conversion rate, substrate inhibition or other issues.

Chinese Journal of <<Amino Acids and Bioresources>>, Vol. 27, No. 1, 2005, pp. 52-55, published an article entitled "Synthesis and Application of β-Aminopropionic Acid" (β-Alanine also called β-Aminopropionic acid). This article reported that Chuan Liyang et al. used a nitrilase-producing microorganism to catalyze the hydrolysis of β-aminopropionitrile to produce β-alanine, and the β-alanine product concentration was 4.2 g/L. Toshio Shinichiro et al. used microorganism for conversion of β-aminopropanol to β-alanine, and the product concentration reached 4 g/L. However, the productivity by the above biological method is low, and it is difficult to meet the requirements of industrial production. According to the principle of catalytic reaction, L-aspartic acid-α-decarboxylase can catalyze the conversion of L-aspartic acid to β-alanine and carbon dioxide. This method is simple, and has little environmental pollution.

However, the L-aspartate-α-decarboxylases found in nature are low in activity or stability, and are usually inhibited by the substrate (L-aspartic acid) or product (β-alanine), which results in insufficient yield and cannot meet the economic requirements of industrial production.

SUMMARY OF THE PRESENT INVENTION

In order to solve the problems existing in the current chemical process for producing β-alanine, the present invention provides an economical and efficient solution using enzymatic conversion which features high product concentration, mild reaction conditions and environmental friendliness. It is easy to operate and easy to be scaled up in industrial setting, so it has a good industrial application prospect.

Scheme 1.
Decarboxylase catalyzes the conversion of L-aspartic acid to β-alanine

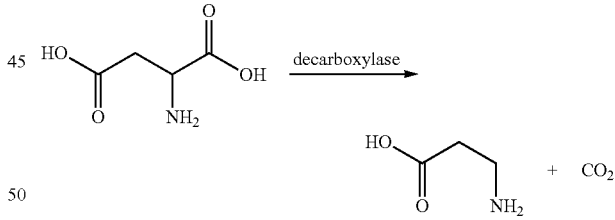

In the first aspect, the present invention provides a novel engineered decarboxylase polypeptide. These engineered decarboxylase polypeptides are derived from artificial directed-evolution process of a poor wild-type decarboxylase, through substitutions, insertions, or deletions of a certain number of amino acid residues. This wild-type decarboxylase is L-aspartate-α-decarboxylase and is derived from *Corynebacterium glutamicum* which consists of 136 amino acids and has the sequence shown in SEQ ID No. 2. The wild type L-aspartate-α-decarboxylase showed low activity and poor stability, and L-aspartic acid (substrate) and β-alanine (product) have inhibition on its activity.

As measured by the inventors, under the reaction condition of the L-aspartic acid loading of 100 g/L and the wet cell (which expressed SEQ ID No: 2) loading of 20 g/L (pH 7.0, 40° C.), the wild-type L-aspartate-α-decarboxylase lost activity in 4 hours after the reaction starts, and the conversion was ≤30%.

In some embodiments, engineered decarboxylase polypeptides of the present disclosure are capable of converting L-aspartic acid to β-alanine with an activity at least equal to or greater than that of SEQ ID No: 2. The engineered decarboxylase polypeptides provided by the present invention has higher activity and/or stability than that of the wild type decarboxylase corresponding to SEQ ID NO: 2, and are capable of catalyzing the conversion of L-aspartic acid to carbon dioxide and β-alanine (Scheme 1) more efficiently. The engineered decarboxylase polypeptides provided by the present invention are capable of catalyzing the conversion of L-aspartic acid to carbon dioxide and β-alanine without being inhibited even at a high substrate (L-aspartic acid) concentration or product (β-alanine) concentration. These engineered decarboxylase polypeptides may comprise an amino acid sequence that differs in one or more residues compared to the sequence of SEQ ID NO: 2 in the residue position: X2, X3, X4, X6, X8, X15, X18, X21, X29, X30, X33, X34, X39, X40, X45, X46, X53, X64, X67, X68, X70, X80, X81, X91, X92, X93, X99, X100, X102, X103, X104, X106, X109, X110, X111, X113, X114, X115, X116, X117, X118, X119, X121, X122, X124, X125, X126, X127, X128, X130, X132, X133, X135, X136. The engineered decarboxylase polypeptides comprise an amino acid sequence comprising at least one of the following features (these features are substitutions of amino acid residues with the reference sequence of SEQ ID NO: 2): L2F, L2S, R3Y, T4S, L6M, S8G, V15T, V15I, A18S, A18V, D21H, D21N, D29S, D29T, A30G, V33I, H34L, H34Y, H34M, I39L, I39R, I39M, E40I, E40V, A45Q, A45L, A45P, I46C, I46V, A53D, A53E, A64W, G67N, G67F, N68A, N68K, N68R, N68E, C70K, N80F, P81M, P81V, P81I, P81L, P81A, L91Y, Q92L, Q92V, A93V, K99N, K99T, K99D, K99S, A100L, A100F, A100W, E102T, E102K, E102L, E102Q, P103A, K104Y, K104S, K104N, V106L, V106I, D109T, A110L, A110M, A110S, D111A, D111Q, D111R, R113G, I114S, I114P, I114N, I114W, I114V, V115C, V115F, V115W, A116N, A116R, A116V, L117Y, L117F, G118R, G118C, N119P, N119A, N119V, N119L, L121G, L121S, L121T, L121C, L121I, A122G, A122S, A124D, A124G, A124H, A124T, L125G, L125D, L125I, P126S, G127E, G127R, G127D, G127I, G127S, G127F, S128K, S128L, L130I, T132Y, T132P, S133T, S133D, S133H, S133V, S135N, S135H, S135Q, I136E, I136S, I136L, I136R, I136F; Or, in addition to the abovementioned differences, engineered decarboxylase polypeptides comprise insertions or deletions of 1, 2, 3, 4, 5, 6, 7, 8, 9, 10, 11, 12, 13, 14, 15, 16, 18, 20, 21, 22, 23, 24, 25 or more amino acid residues.

More specifically, in some embodiments, the engineered decarboxylase polypeptides which were improved over SEQ ID NO: 2 comprises a sequence corresponding to SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390.

In some embodiments, the engineered decarboxylase polypeptides comprise an amino acid sequence that is at least 80%, 85%, 86%, 87%, 88%, 89%, 90%, 91%, 92%, 93%, 94%, 95%, 96%, 97%, 98%, 99% or more identical to the reference sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390.

The identity between two amino acid sequences or two nucleotide sequences can be obtained by commonly used algorithms in the art and can be calculated according to default parameters by using NCBI Blastp and Blastn software, or by using the Clustal W algorithm (Nucleic Acid Research, 22 (22): 4673-4680, 1994).

For example, using the Clustal W algorithm, the amino acid sequence identity of SEQ ID NO: 2 to SEQ ID NO: 374 is 92.6%.

In another aspect, this invention provides polynucleotide sequences encoding engineered decarboxylase polypeptides. In some embodiments, a polynucleotide can be part of an expression vector having one or more control sequences for the expression of an engineered decarboxylase polypeptide. In some embodiments, polynucleotides can comprise sequences corresponding to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389.

As known to people skilled in the art, due to the degeneracy of the nucleotide codons, the polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390 are not limited to SEQ ID No: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389. The polynucleotide sequences of the engineered decarboxylase polypeptides of the present invention may also be any other polynucleotide sequences encoding amino acid sequences SEQ ID No: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390.

In another aspect, this disclosure provides polynucleotides comprising sequences encoding engineered decarboxylase polypeptides, expression vectors and host cells capable of expressing engineered decarboxylase polypeptides. In some embodiments, the host cell can be bacterial host cell, such as E. coli. The host cell can be used to express and isolate the engineered decarboxylase described herein, or alternatively be directly used in the reaction for conversion of substrates to products.

In some embodiments, the engineered decarboxylase in the form of whole cell, crude extract, isolated enzyme, or purified enzyme can be used alone or in an immobilized form, such as immobilization on a resin.

The present disclosure also provides the process of preparing an amino compound of formula (I) using the engineered decarboxylase polypeptides disclosed herein to convert an amino acid of formula (II):

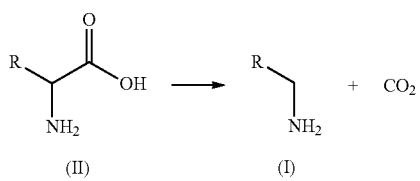

wherein R is an optionally substituted or unsubstituted $C_1$-$C_8$ hydrocarbyl, or an optionally substituted or unsubstituted aryl or heteroaryl; the process comprising that, amino acid substrates of formula (II) were contacted with the decarboxylase polypeptides under suitable reaction conditions, wherein the decarboxylase polypeptides are the engineered decarboxylase polypeptides as described herein. In some embodiments, the engineered decarboxylase polypeptides have at least 80%, 85%, 86%, 87%, 88%, 89%, 90%, 91%, 92%, 93%, 94%, 95%, 96%, 97%, 98%, 99% or more of sequence identity to SEQ ID NO: 2 and are capable of converting a compound of formula (II) to the compound of formula (I) at higher conversion compared to SEQ ID NO: 2.

In some embodiments, the engineered decarboxylase polypeptides can be used in the process of preparing β-alanine:

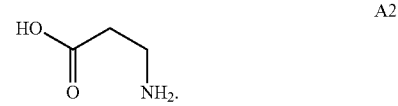

In these embodiments, the process comprising that, under suitable reaction conditions, the compound of formula A1:

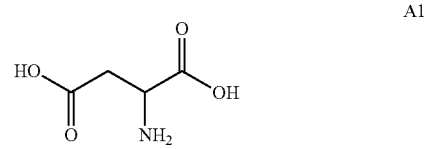

were contacted with the engineered decarboxylase polypeptides disclosed herein.

Specific embodiments of engineered decarboxylase polypeptides for use in this process are further provided in the examples. An engineered decarboxylase polypeptide that can be used in the above process can comprise one or more sequences selected from the amino acid sequences corresponding to SEQ ID NO:4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390.

Any of the processes for the preparation of a compound of formula (I) or a compound of formula A2 using an engineered polypeptide as disclosed herein can be performed under a range of suitable reaction conditions, which including, but not limited to, pH, temperature, buffer, solvent system, substrate loading, polypeptide loading, pressure, and reaction time range. For example, in some embodiments, preparing a compound of formula (I) or a compound of formula A2 can be performed, wherein suitable reaction conditions include: (a) about 10 g/L to about 200 g/L of a substrate compound (e.g., compound (II) or A1); (b) about 0.5 g/L to about 10 g/L of engineered polypeptide, or about 1 g/L to about 100 g/L of wet cells expressing the engineered polypeptides; (c) 0% (v/v) to about 60% (v/v) of organic solvent, including but not limited to, dimethyl sulfoxide (DMSO), dimethylformamide (DMF), isopropyl acetate, Methanol, ethanol, propanol or isopropanol (IPA); (d) a pH of about 4.0 to about 8.0; and (e) a temperature of about 10° C. to about 60° C.

DETAILED DESCRIPTION OF THE PRESENT INVENTION

1. Definitions

Unless expressly defined otherwise, technical and scientific terms used in this disclosure have the meanings that are commonly understood by people skilled in the art.

"Protein", "polypeptide" and "peptide" are used interchangeably herein to denote a polymer of at least two amino acids covalently linked by an amide bond, regardless of length or post-translational modification (e.g., glycosylation, phosphorylation, lipidation, myristoylation, ubiquitination, etc.). This definition includes D-amino acids and L-amino acids, as well as mixtures of D-amino acids and L-amino acids.

L-aspartate and L-aspartic acid are used interchangeably herein.

"Engineered decarboxylase", "engineered decarboxylase polypeptide", "improved decarboxylase polypeptide" and "engineered polypeptide" are used interchangeably herein.

"Bacteria" or "wet cells" refers to host cells which expresses a polypeptide or engineered polypeptide, including the wet cells obtained in the preparation procedures shown in Example 2 and Example 8.

"Polynucleotide" and "nucleic acid" are used interchangeably herein.

"Coding sequence" refers to that portion of a nucleic acid (e.g., a gene) that encodes an amino acid sequence of a protein.

"Naturally occurring" or "wild-type" refers to the form found in nature. For example, a naturally-occurring or wild-type polypeptide or polynucleotide sequence is a sequence that is present in an organism that can be isolated from sources in nature and which has not been intentionally modified by manual procedures.

"Recombinant" or "engineered" or "non-naturally occurring" when used with reference to, for example, a cell, nucleic acid or polypeptide, refers to a material or material corresponding to the native form of the material, that has been modified in a manner that would not otherwise exist in nature, or is identical thereto but produced or derived from synthetic material and/or by manipulation using recombinant techniques.

"Sequence identity" and "homology" are used interchangeably herein to refer to comparisons between polynucleotide sequences or polypeptide sequences ("sequence identity" and "homology" are generally expressed as a percentage), and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage can be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity.

Those skilled in the art will appreciate that there are many established algorithms available to align two sequences. The optimal alignment of sequences for comparison can be conducted, for example, by the local homology algorithm of Smith and Waterman, 1981, Adv. Appl. Math. 2: 482, by the Homology alignment algorithm of Needleman and Wunsch, 1970, J. Mol. Biol. 48: 443, by the search for similarity method of Pearson and Lipman, 1988, Proc. Natl. Acad. Sci. USA 85: 2444, by computerized implementations of these algorithms (GAP, BESTFIT, FASTA, and TFASTA in the GCG Wisconsin Package) or by visual inspection (see generally, Current Protocols in Molecular Biology, FM Ausubel et al. eds., Current Protocols, a Joint Venture between Greene Publishing Associates, Inc. and John Wiley & Sons, Inc., (1995 Supplement) (Ausubel)). Examples of algorithms that are suitable for determining the percent sequence identity and percent sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively.

Software for performing BLAST analysis is publicly available through the National Center for Biotechnology Information website. The algorithm involves first identifying high scoring sequence pairs (HSPs) by identifying short words of length W in the query sequence, which either match or satisfy some positive-valued threshold scores T when aligned with a word of the same length in the database sequence. T is referred to as, the neighborhood word score threshold (Altschul et al., Supra). These initial neighborhood word hits serve as seeds for initiating searches to find longer HSPs that contain them. The word hits are then extended in both directions along each sequence for as far as the cumulative alignment score can be increased. For nucleotide sequences, the cumulative scores are calculated using the parameters M (reward score for matched pair of residues; always>0) and N (penalty score for mismatched residues; always<0).

For amino acid sequences, a scoring matrix is used to calculate the cumulative score. The extension of the word hits in each direction are halted when: the cumulative alignment score falls off by the quality X from its maximum achieved value; the cumulative score goes 0 or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, the expected value (E) of 10, M=5, N=-4, and a comparison of both strands as a default value. For amino acid sequences, the BLASTP program uses as defaults the wordlength (W) of 3, the expected value (E) of 10 and the BLOSUM62 scoring matrix (see Henikoff and Henikoff, 1989, Proc Natl Acad Sci USA 89: 10915). Exemplary determination of sequence alignments and % sequence identity can employ the BESTFIT or GAP programs in the GCG Wisconsin Software package (Accelrys, Madison Wis.), using the default parameters provided.

"Reference sequence" refers to a defined sequence that is used as a basis for sequence comparison. The reference sequence may be a subset of a larger sequence, for example, a full-length gene or a fragment of a polypeptide sequence. In general, a reference sequence is at least 20 nucleotides or amino acid residues in length, at least 25 residues in length, at least 50 residues in length, or the full length of the nucleic acid or polypeptide. Because two polynucleotides or polypeptides may each (1) comprise a sequence (i.e., a portion of the complete sequence) that is similar between two sequences, and (2) may further comprise sequences that is divergent between the two sequences, sequence comparisons between two (or more) polynucleotides or polypeptides are typically performed by comparing the sequences of the two polynucleotides or polypeptides over a "comparison window" to identify and compare local regions of sequence similarity. In some embodiments, a "reference sequence" is not intended to be limited to a wild-type sequence, and may comprise engineered or altered sequences. For example, "a reference sequence with leucine at the residue corresponding to X39 based on SEQ ID NO: 2" refers to a reference sequence wherein the corresponding residue at position X39 in SEQ ID NO: 2 which is proline, has been altered to leucine.

A "comparison window" refers to a conceptual segment of at least about 20 contiguous nucleotide positions or amino acid residues, wherein the sequence may be compared to a reference sequence of at least 20 contiguous nucleotides or amino acids and wherein the portions of the sequence in the comparison window may comprise additions or deletions (i.e., gaps) of 20% or less as compared to a reference sequence (which does not comprise additions or deletions) for optimal alignment of the two sequences. The comparison window can be longer than 20 contiguous residues, and optionally include 30, 40, 50, 100 or more residues.

In the context of the numbering for a given amino acid or polynucleotide sequence, "corresponding to," "reference to" or "relative to" refers to the numbering of the residues of a specified reference when the given amino acid or polynucleotide sequence is compared to the reference sequence. In other words, the residue number or residue position of a given sequence is designated with respect to the reference sequence, rather than by the actual numerical position of the residue within the given amino acid or polynucleotide sequence.

For example, a given amino acid sequence such as an engineered decarboxylase can be aligned to a reference sequence by introducing gaps to optimize residue matches between the two sequences. In these cases, although there are gaps, the numbering of the residue in a given amino acid or polynucleotide sequence is made with respect to the reference sequence to which they have been aligned.

"Amino acid difference" or "residue difference" refers to the difference in amino acid residues at a position of a polypeptide sequence relative to the amino acid residue at a corresponding position in the reference sequence. The positions of amino acid differences are generally referred to herein as "Xn", where n refers to the corresponding position in the reference sequence on which the residue differences are based. For example, "a residue difference at position X39 as compared to SEQ ID NO: 2" refers to the difference in amino acid residues at the polypeptide position corresponding to position 39 of SEQ ID NO: 2. Thus, if the reference polypeptide of SEQ ID NO: 2 has a proline at position 39, then "a residue difference at position X39 as compared to SEQ ID NO: 2" refers to an amino acid substitution of any residue other than proline at the position of the polypeptide corresponding to position 39 of SEQ ID NO: 2. In most of the examples herein, the specific amino acid residue difference at the position is indicated as "XnY", wherein "Xn" specified to the corresponding position as described above, and "Y" is the single letter identifier of the amino acid found in the engineered polypeptide (i.e., a different residue than in the reference polypeptide). In some examples (e.g., in Table 1), the present disclosure also provides specific amino acid differences denoted by the conventional notation "AnB", where A is a single letter identifier of a residue in the reference sequence, "n" is the number of residue position in the reference sequence, and B is the single letter identifier for the residue substitution in the sequence of the engineered polypeptide. In some examples, an engineered polypeptide of this disclosure may comprise one or more amino acid residue differences relative to a reference sequence, which is indicated by a list of specific positions at which residue differences are present relative to a reference sequence. In some embodiments, more than one amino acid residue can be used in a specific residue position of an engineered polypeptide, the various amino acid residues that can be used are separated by a "/" (e.g., X39L/X39A).

"Deletion" refers to the modification of a polypeptide by removing one or more amino acids from a reference polypeptide. Deletions can include the removal of one or more amino acids, two or more amino acids, five or more amino acids, ten or more amino acids, fifteen or more amino acids, or twenty or more amino acids, up to 10% of the total number of amino acids of the enzyme, or up to 20% of the total number of amino acids making up the reference enzyme while retaining the enzymatic activity of the engineered decarboxylase and/or retaining the improved properties of the engineered decarboxylase. Deletion may involve the internal portion and/or the terminal portion of the polypeptide.

In various embodiments, deletions may include a contiguous segment or may be discontinuous.

"Insertion" refers to the modification of a polypeptide by adding one or more amino acids from a reference polypeptide. In some embodiments, the improved engineered decarboxylase comprises insertions of one or more amino acids to a naturally-occurring decarboxylase polypeptide as well as insertions of one or more amino acids to other engineered decarboxylase polypeptides. It can be inserted in the internal portions of the polypeptide or inserted to the carboxyl or amino terminus. As used herein, insertions include fusion proteins known in the art. The insertion can be a contiguous segment of amino acids or separated by one or more amino acids in naturally-occurring or engineered polypeptides.

"Fragment" as used herein refers to a polypeptide having an amino terminal and/or carboxyl terminal deletion, but where the remaining amino acid sequence is identical to the corresponding position in the sequence. Fragments may be at least 10 amino acids long, at least 20 amino acids long, at least 50 amino acids long or longer, and up to 70%, 80%, 90%, 95%, 98% and 99% of the full-length decarboxylase polypeptide.

An "isolated polypeptide" refers to a polypeptide that is substantially separated from other substances with which it is naturally associated, such as proteins, lipids, and polynucleotides. The term comprises polypeptides that have been removed or purified from their naturally occurring environment or expression system (e.g., in host cells or in vitro synthesis). Engineered decarboxylase polypeptides may be present in the cell, in the cell culture medium, or prepared in various forms, such as lysates or isolated preparations. As such, in some embodiments, the engineered decarboxylase polypeptide may be an isolated polypeptide.

"Improved enzyme properties" refers to an enzyme property that is better or more desirable for a specific purpose as compared to a reference decarboxylase such as a wild-type decarboxylase or another improved engineered decarboxylase. Improved enzyme properties are exhibited by engineered decarboxylase polypeptides in this disclosure. Enzyme properties that are expected to be improved include, but are not limited to, enzyme activity (which can be expressed as a percentage of substrate conversion), thermal stability, solvent stability, pH activity characteristics, cofactor requirements, tolerance to inhibitors (e.g., substrate or product inhibition), stereospecificity and stereoselectivity (including enantioselectivity or diastereoselectivity).

"Conversion" refers to the enzymatic transformation of a substrate to the corresponding product. "Percent conversion" or "conversion" refers to the percentage of substrate that is converted to product within a period of time under the specified conditions. Thus, "enzymatic activity" or "activity" of a decarboxylase polypeptide can be expressed as the "percent conversion" of the substrate to the product.

"Thermostable" means that a decarboxylase polypeptide that retains similar activity (e.g., greater than 50%) after being exposed to an elevated temperature (e.g., 30-80° C.) for a period of time (0.5-24 h).

"Solvent-stable" refers to a decarboxylase polypeptide that maintains similar activity (for example more than 50% to 80%) after exposure to varying solvent (ethanol, isopropanol, dimethylsulfoxide (DMSO), tetrahydrofuran, 2-Methyltetrahydrofuran, acetone, toluene, butyl acetate, methyl tert-butyl ether, etc.) for a period of time (e.g., 0.5-24 hours).

"Suitable reaction conditions" refer to those conditions (e.g., enzyme loading, substrate loading, cofactor loading, temperature, pH, buffer, co-solvent, etc.) in the biocatalytic reaction system, under which the decarboxylase polypeptide of the present disclosure can convert a substrate to a desired product compound.

Exemplary "suitable reaction conditions" are provided in the present disclosure and illustrated by examples.

"Hydrocarbyl" refers to a straight or branched hydrocarbon group. The number of subscripts following the symbol "C" specifies the number of carbon atoms that a particular group may contain. For example, "$C_1$-$C_8$" refers to a straight or branched chain hydrocarbyl group having 1 to 8 carbon atoms. Hydrocarbyl groups may optionally be substituted with one or more substituent groups.

"Aryl" means a monovalent aromatic hydrocarbon radical of 6 to about 20 carbon atoms. "Heteroaryl" and "heteroaromatic" refer to an aryl group in which one or more of the carbon atoms of the parent aromatic ring system is/are replaced by a heteroatom (O, N, or S). "Substituted", when used to modify a specified group or radical, means that one or more hydrogen atoms of the specified group or radical are each replaced, independently of one another, by identical or different substituents. "Substituted hydrocarbyl, aryl, or heteroaryl" refers to a hydrocarbyl, aryl, or heteroaryl group in which one or more hydrogen atoms are replaced by other substituents. "Optional" or "optionally" means that the described event or circumstance may or may not occur; for example, "optionally substituted aryl" refers to an aryl group that may or may not be substituted. This description includes both substituted aryl groups and unsubstituted aryl groups.

As used herein, "compound" refers to any compound encompassed by the structural formulas and/or chemical names indicated with the compounds disclosed herein. Compounds may be identified by their chemical structure and/or chemical name. When the chemical structure and chemical name conflict, the chemical structure determines the identity of the compound. Unless specifically stated or indicated otherwise, the chemical structures described herein encompass all possible isomeric forms of the described compounds.

2. Engineered Decarboxylase Polypeptides

The present invention provides amino acid sequences of engineered decarboxylase that are useful for catalyzing the conversion of L-aspartic acid to β-alanine under industrial-relevant conditions. The present disclosure also provides polynucleotides encoding engineered decarboxylase polypeptides.

Compared to the wild-type decarboxylase, the engineered decarboxylase polypeptide provided by the invention has better activity and stability, and overcomes the inhibition of L-aspartic acid and/or β-alanine on the enzyme, the use of the engineered polypeptides of the present invention for the preparation of β-alanine results in higher unit activity, lower cost, and has good industrial application prospects.

Table 1 below illustrates the engineered decarboxylase polypeptides developed by the present invention. Each row gives the nucleotide sequence number and amino acid sequence number of a particular engineered decarboxylase polypeptide, as well as the residue differences compared to SEQ ID No: 2. The catalytic performance of each of the exemplified engineered decarboxylase polypeptides (the overall performance in the reaction, combining activity, stability, and performance against substrate or product inhibition) is indicated by "+", with the specific meanings given in Table 2.

TABLE 1

| Polynucleotide SEQ ID No | Amino acid SEQ ID No | Residue difference relative to SEQ ID NO: 2 | Catalytic performance |
|---|---|---|---|
| 1 | 2 | — | |
| 3 | 4 | V15T; | + |
| 5 | 6 | V15I; | + |
| 7 | 8 | A18S; | + |
| 9 | 10 | A18V; | + |
| 11 | 12 | D21H; | + |
| 13 | 14 | E40I; | + |
| 15 | 16 | E40V; | + |
| 17 | 18 | A45Q; | + |
| 19 | 20 | A45L; | + |
| 21 | 22 | I45C; | + |
| 23 | 24 | A53D; | + |
| 25 | 26 | A53E; | + |

TABLE 1-continued

| Polynucleotide SEQ ID No | Amino acid SEQ ID No | Residue difference relative to SEQ ID NO: 2 | Catalytic performance |
|---|---|---|---|
| 27 | 28 | D29S; | + |
| 29 | 30 | A64W; | + |
| 31 | 32 | G67N; | + |
| 33 | 34 | A100L; | + |
| 35 | 36 | P103A; | + |
| 37 | 38 | E102T; | + |
| 39 | 40 | V106L; | + |
| 41 | 42 | V106I; | + |
| 43 | 44 | D109T; | + |
| 45 | 46 | K104Y;R113G; | + |
| 47 | 48 | A18V;G67F;D109T; | ++ |
| 49 | 50 | A18V;D29T;V106I;D109T; | ++ |
| 51 | 52 | A18V;D109T; | ++ |
| 53 | 54 | A18V;V106I;D109T; | ++ |
| 55 | 56 | A18V;V106I; | ++ |
| 57 | 58 | A18V;A100L;V106I; | ++ |
| 59 | 60 | A18V;D29T;D109T; | ++ |
| 51 | 52 | A18V;E102T; | ++ |
| 53 | 54 | A18V;V106I;D109T; | ++ |
| 55 | 56 | A18V;V106I; | ++ |
| 57 | 58 | A18V;A100L;V106I; | ++ |
| 59 | 60 | A18V;D29T;DD109T; | ++ |
| 61 | 62 | A18V;E102T; | ++ |
| 63 | 64 | A18V;P103A;K104Y; | ++ |
| 65 | 66 | A18V;D29T;K104Y; | ++ |
| 67 | 68 | A18V;G67F;E102T; | ++ |
| 69 | 70 | A18V;K104Y; | ++ |
| 71 | 72 | A18V;G67F;P103A; | ++ |
| 73 | 74 | A18V;E40I;E102T;K104Y; | ++ |
| 75 | 76 | A18V;E40I;P103A; | ++ |
| 77 | 78 | L2F;A18V; | ++ |
| 79 | 80 | L2S;A18V; | ++ |
| 81 | 82 | T4S;A18V; | ++ |
| 83 | 84 | L6M;A18V; | ++ |
| 85 | 56 | S8G;A18V; | ++ |
| 87 | 88 | A18V;I114S; | ++ |
| 89 | 90 | A18V;V115C; | ++ |
| 91 | 92 | A18V;I114P; | ++ |
| 93 | 94 | A18V;I114N; | ++ |
| 95 | 96 | A18V;I114W; | ++ |
| 97 | 98 | A18V;K99N;I114N; | ++ |
| 99 | 100 | A18V;A116H; | ++ |
| 101 | 102 | A18V;L117Y; | ++ |
| 103 | 104 | A18V;L117F; | ++ |
| 105 | 106 | A18V;N119P; | ++ |
| 107 | 108 | A18V;N119A; | ++ |
| 109 | 110 | A18V;N119V | ++ |
| 111 | 112 | A18V;L121G; | ++ |
| 113 | 114 | A18V;L121S; | ++ |
| 115 | 116 | A18V;L121T; | ++ |
| 117 | 118 | A18V;A124D; | ++ |
| 119 | 120 | A18V;A124G; | ++ |
| 121 | 122 | A18V;A124H; | ++ |
| 123 | 124 | A18V;L125G; | ++ |
| 125 | 126 | A18V;L125D; | ++ |
| 127 | 128 | A18V;G127E; | ++ |
| 129 | 130 | A18V;G127R; | ++ |
| 131 | 132 | A18V;L130I; | ++ |
| 133 | 134 | A18V;S133T; | ++ |
| 135 | 136 | A18V;S133D; | ++ |
| 137 | 138 | A18V;S135N; | ++ |
| 139 | 140 | A18V;I136E; | ++ |
| 141 | 142 | A18V;K104Y;V106I;D109T; | +++ |
| 143 | 144 | A18V;D21H;V106I;D109T; | +++ |
| 145 | 146 | A18V;D21H;K104Y;V106I;D109T; | +++ |
| 147 | 148 | A18V;D21H;P103A;V106I;D109T; | +++ |
| 149 | 150 | A18V;V106I;D109T;L125D;G127R;S133H; | +++ |
| 151 | 152 | R3Y;A18V;V106I;D109T; | +++ |
| 153 | 154 | A18V;K104Y;V106I;D109T;S135H; | +++ |
| 155 | 156 | A18V;K104Y;V106I;D109T;S135Q; | +++ |
| 157 | 158 | A18V;K104Y;V106I;D109T;I136S; | +++ |
| 159 | 160 | A18V;K104Y;V106I;D109T;I136L; | +++ |
| 161 | 162 | R3Y;A18V;V106I;D109T;I136L; | +++ |
| 163 | 164 | R3Y;A18S;V106I;D109T;I136L; | +++ |
| 165 | 166 | R3Y;V106I;D109T;I136L; | +++ |

TABLE 1-continued

| Polynucleotide SEQ ID No | Amino acid SEQ ID No | Residue difference relative to SEQ ID NO: 2 | Catalytic performance |
|---|---|---|---|
| 167 | 168 | R3Y;A18V;A100F;V106I;D109T;I136L; | +++ |
| 169 | 170 | R3Y;A18V;A100W;V106I;D109T;I136L; | +++ |
| 171 | 172 | R3Y;A18V;V106I;D109T;I136R; | +++ |
| 173 | 174 | R3Y;A18V;V106I;D109T;I136F; | +++ |
| 175 | 176 | R3Y;A18V;V106I;D109T;I114V; | ++++ |
| 177 | 178 | R3Y;A18V;V106I;D109T;V115F; | ++++ |
| 179 | 180 | R3Y;A18V;V106I;D109T;V115W; | ++++ |
| 181 | 182 | R3Y;A18V;V106I;D109T;N119V; | ++++ |
| 183 | 184 | R3Y;A18V;V106I;D109T;N119L; | ++++ |
| 185 | 186 | R3Y;A18V;V106I;D109T;L121C; | ++++ |
| 187 | 188 | R3Y;A18V;V106I;D109T;L121I; | ++++ |
| 189 | 190 | R3Y;A18V;V106I;D109T;L125I; | ++++ |
| 191 | 192 | R3Y;A18V;V106I;D109T;P126S; | ++++ |
| 193 | 194 | R3Y;A18V;V106I;D109T;G127D; | ++++ |
| 195 | 196 | R3Y;A18V;V106I;D109T;G127I; | ++++ |
| 197 | 198 | R3Y;A18V;V106I;D109T;G127S; | ++++ |
| 199 | 200 | R3Y;A18V;V106I;D109T;G127Y; | ++++ |
| 201 | 202 | R3Y;A18V;V106I;D109T;S133V; | ++++ |
| 203 | 204 | R3Y;A18V;V106I;D109T;I136E; | ++++ |
| 205 | 206 | R3Y;A18V;A45Q;V106I;D109T; | ++++ |
| 207 | 208 | R3Y;A18V;V106I;D109T;A116R; | ++++ |
| 209 | 210 | R3Y;A18V;V106I;D109T;A116V; | ++++ |
| 211 | 212 | R3Y;A18V;V106I;D109T;G118R; | ++++ |
| 213 | 214 | R3Y;A18V;V106I;D109T;G118C; | ++++ |
| 215 | 216 | R3Y;A18V;V106I;D109T;S128K; | ++++ |
| 217 | 218 | R3Y;A18V;V106I;D109T;S128L; | ++++ |
| 219 | 220 | R3Y;A18V;K99T;V106I;D109T; | ++++ |
| 221 | 222 | R3Y;A18V;K99D;V106I;D109T; | ++++ |
| 223 | 224 | R3Y;A18V;K99S;V106I;D109T; | ++++ |
| 225 | 226 | R3Y;A18V;V106I;D109T;A122F; | ++++ |
| 227 | 228 | R3Y;A18V;V106I;D109T;A122S; | ++++ |
| 229 | 230 | R3Y;A18V;V106I;D109T;T132Y; | ++++ |
| 231 | 232 | R3Y;A18V;V106I;D109T;T132P; | ++++ |
| 233 | 234 | R3Y;A18V;V33I;V106I;D109T; | ++++ |
| 235 | 236 | R3Y;A18V;H34L;V106I;D109T; | ++++ |
| 237 | 238 | R3Y;A18V;H34Y;V106I;D109T; | ++++ |
| 239 | 240 | R3Y;A18V;I39L;V106I;D109T; | ++++ |
| 241 | 242 | R3Y;A18V;I39R;V106I;D109T; | ++++ |
| 243 | 244 | R3Y;A18V;I39M;V106I;D109T; | ++++ |
| 245 | 246 | R3Y;A18V;C70K;V106I;D109T; | ++++ |
| 247 | 248 | R3Y;A18V;P81M;V106I;D109T; | ++++ |
| 249 | 250 | R3Y;A18V;P81V;V106I;D109T; | ++++ |
| 251 | 252 | R3Y;A18V;P81I;V106I;D109T; | ++++ |
| 253 | 254 | R3Y;A18V;P81L;V106I;D109T; | ++++ |
| 255 | 256 | R3Y;A18V;P81A;V106I;D109T; | ++++ |
| 257 | 258 | R3Y;A18V;A93V;V106I;D109T; | ++++ |
| 259 | 260 | R3Y;A18V;Q92L;V106I;D109T; | ++++ |
| 261 | 262 | R3Y;A18V;Q92V;V106I;D109T; | ++++ |
| 263 | 264 | R3Y;A18V;D21N;V106I;D109T; | ++++ |
| 265 | 266 | R3Y;A18V;A30G;V106I;D109T; | ++++ |
| 267 | 268 | R3Y;A18V;N68A;V106I;D109T; | ++++ |
| 269 | 270 | R3Y;A18V;N68K;V106I;D109T; | ++++ |
| 271 | 272 | R3Y;A18V;N68R;V106I;D109T; | ++++ |
| 273 | 274 | R3Y;A18V;N68E;V106I;D109T; | ++++ |
| 275 | 276 | R3Y;A18V;N80F;V106I;D109T; | ++++ |
| 277 | 278 | R3Y;A18V;L91Y;V106I;D109T; | ++++ |
| 277 | 278 | R3Y;A18V;L91Y;V106I;D109T; | ++++ |
| 279 | 280 | R3Y;A18V;K104S;V106I;D109T; | ++++ |
| 281 | 282 | R3Y;A18V;E102K;V106I;D109T; | ++++ |
| 283 | 284 | R3Y;A18V;E102L;V106I;D109T; | ++++ |
| 285 | 286 | R3Y;A18V;K104N;V106I;D109T; | ++++ |
| 287 | 288 | R3Y;A18V;E102Q;V106I;D109T; | ++++ |
| 289 | 290 | R3Y;A18V;E102T;V106I;D109T; | ++++ |
| 291 | 292 | R3Y;A18V;V106I;D109T;A110L; | ++++ |
| 293 | 294 | R3Y;A18V;V106I;D109T;A110M; | ++++ |
| 295 | 296 | R3Y;A18V;V106I;D109T;A110S; | ++++ |
| 297 | 298 | R3Y;A18V;V106I;D109T;D111A; | ++++ |
| 299 | 300 | R3Y;A18V;V106I;D109T;D111Q; | ++++ |
| 301 | 302 | R3Y;A18V;V106I;D109T;A124T; | ++++ |
| 303 | 304 | R3Y;A18V;I46V;V;106I;D109T; | ++++ |
| 305 | 306 | R3Y;A18V;A45Q;V106I;D109T;I136L | +++++ |
| 307 | 308 | R3Y;A18V;I39R;A45Q;V106I;D109T;I136L | +++++ |
| 309 | 310 | R3Y;A18V;D21N;A45Q;V106I;D109T;I136L | +++++ |
| 311 | 312 | R3Y;A18V;D21N;A45Q;V106I;D109T;A122S;L125I;I136L | +++++ |
| 313 | 314 | R3Y;A18V;I39R;A45Q;V106I;D109T;A124T;I136L | +++++ |

TABLE 1-continued

| Polynucleotide SEQ ID No | Amino acid SEQ ID No | Residue difference relative to SEQ ID NO: 2 | Catalytic performance |
|---|---|---|---|
| 315 | 316 | R3Y;A18V;D21N;I39R;A45Q;V106I;D109T;A122S;I136L | +++++ |
| 317 | 318 | R3Y;A18V;D21N;A45Q;V106I;D109T;A124T;I136L | +++++ |
| 319 | 320 | R3Y;A18V;D21N;A45P;V106I;D109T;A122S;I136L | +++++ |
| 321 | 322 | R3Y;A18V;I39R;V106I;D109T;L125I;I136L | +++++ |
| 323 | 324 | R3Y;A18V;I39R;V106I;D109T;A122S;L125I;I136L | +++++ |
| 325 | 326 | R3Y;A18V;D21N;V106I;D109T;A122S;A124T;L125I;I136L | +++++ |
| 327 | 328 | R3Y;A18V;D21N;I39R;V106I;D109T;A122S;I136L | +++++ |
| 329 | 330 | R3Y;A18V;D21N;I39R;V106I;D109T;A122S;L125I;I136L | +++++ |
| 331 | 332 | R3Y;A18V;H34L;A45Q;V106I;D109T;I136L | +++++ |
| 333 | 334 | R3Y;A18V;H34L;A45Q;D109T;I136L | +++++ |
| 335 | 336 | R3Y;A18V;A45Q;V106I;D109T;D111Q;I136L | +++++ |
| 337 | 338 | R3Y;A18V;V33I;I39R;A45Q;V106I;D109T;I136L | +++++ |
| 339 | 340 | R3Y;A18V;Q92L;A93V;V106I;D109T;I136L | +++++ |
| 341 | 342 | R3Y;A18V;A93V;V106I;D109T;I136L | +++++ |
| 343 | 344 | R3Y;A18V;H34Y;A45Q;V106I;D109T;I136L | +++++ |
| 345 | 346 | R3Y;A18V;H34M;A45Q;V106I;D109T;I136L | +++++ |
| 347 | 348 | R3Y;A18V;A45Q;I46V;V106I;D109T;I136L | +++++ |
| 349 | 350 | R3Y;A18V;A45Q;V106I;D109T;G127R;I136L | +++++ |
| 351 | 352 | R3Y;A18V;A45Q;V106I;D109T;G127F;I136L | +++++ |
| 353 | 354 | R3Y;A18V;D21N;I39R;A45Q;V106I;D109T;L125I;I136L | +++++ |
| 355 | 356 | R3Y;A18V;D21N;A45Q;V106I;D109T;A122S;A124T;I136L | +++++ |
| 357 | 358 | R3Y;A18V;V33I;I39R;A45Q;Q92L;V106I;D109T;I136L | +++++ |
| 359 | 360 | R3Y;A18V;I39R;A45Q;L91Y;Q92L;V106I;D109T;I136L | +++++ |
| 361 | 362 | R3Y;A18V;V33I;A45Q;V106I;D109T;I136L | +++++ |
| 363 | 364 | R3Y;A18V;A45Q;L91Y;Q92L;V106I;D109T;D111Q;I136L | +++++ |
| 365 | 366 | R3Y;A18V;A45Q;L91Y;V106I;D109T;I136L | +++++ |
| 367 | 368 | R3Y;A18V;H34L;I39R;A45Q;A93V;V106I;D109T;I136L | +++++ |
| 369 | 370 | R3Y;A18V;A45Q;Q92V;V106I;D109T;I136L | +++++ |
| 371 | 372 | R3Y;A18V;V33I;I39R;A45Q;A93V;V106I;D109T;I136L | +++++ |
| 373 | 374 | R3Y;A18V;I39R;A45Q;Q92L;A93V;K104S;V106I;D109T;I136L | +++++ |
| 375 | 376 | R3Y;A18V;A45Q;L91Y;Q92L;A93V;V106I;D109T;I136L | +++++ |
| 377 | 378 | R3Y;A18V;I39R;A45Q;V106I;D109T;D111Q;I136L | +++++ |
| 379 | 380 | R3Y;A18V;A45Q;Q92L;V106I;D109T;D111R;I136L | +++++ |
| 381 | 382 | R3Y;A18V;V33I;A45Q;A93V;V106I;D109T;I136L | +++++ |
| 383 | 384 | R3Y;A18V;A45Q;Q92L;A93V;V106I;D109T;I136L | +++++ |

TABLE 2

| Catalytic performance | Description | Reaction condition |
|---|---|---|
| + | Conversion ≥50%, reaction time ≤24 hours | Wet cell 2 g/L, substrate(L-aspartic acid) 20 g/L, pH 7.0~pH 8.0, 40 C.° |
| ++ | Conversion ≥50%, reaction time ≤24 hours | Wet cell 20 g/L, substrate(L-aspartic acid) 100 g/L, pH 7.0~pH 8.0, 50 C.° |
| +++ | Conversion ≥70%, reaction time ≤24 hours | Wet cell 20 g/L, substrate(L-aspartic acid) 100 g/L, pH 6.0~pH 7.0, 50 C.° |
| ++++ | Conversion ≥90%, reaction time ≤24 hours | Wet cell 20 g/L, substrate(L-aspartic acid) 100 g/L, pH 6.0~pH 7.0, 50 C.° |
| +++++ | Conversion ≥95%, reaction time ≤24 hours | Wet cell 20 g/L, substrate(L-aspartic acid) 150 g/L, pH 6.0~pH 7.0, 50 C.° |

The amino acid sequences listed in Table 1 i.e., the even sequence identifiers of SEQ ID NO: 2 to 384) each contain 136 amino acid residues. SEQ ID NO: 386, 388, or 390 has a different number of deletion or substitution of amino acid residues as compared to SEQ ID No: 2. Under the reaction conditions shown in Table 2, the engineered decarboxylase polypeptide of SEQ ID NO: 386, 388, or 390 has higher catalytic performance than that of SEQ ID No: 2. The wet cells described in Table 2 refer to wet cells in which the decarboxylase polypeptide corresponding to the amino acid sequence in Table 1 was expressed in equal amount.

3. Polynucleotides, Control Sequences, Expression Vectors and Host Cells that can be Used to Produce Engineered Decarboxylase Polypeptides In another aspect, this disclosure provides polynucleotides encoding engineered polypeptides having decarboxylase activity described herein. The polynucleotides can be linked to one or more heterologous regulatory sequences that control gene expression to produce recombinant polynucleotides that are capable of expressing the engineered polypeptides.

Expression constructs comprising a heterologous polynucleotide encoding an engineered decarboxylase may be introduced into a suitable host cell to express the corresponding engineered decarboxylase polypeptide.

As apparent to one skilled in the art, the availability of protein sequences and knowledge of codons corresponding to a variety of amino acids provide an illustration of all possible polynucleotides that encode the protein sequence of interest. The degeneracy of the genetic code, in which the same amino acid is encoded by selectable or synonymous codons, allows for the production of an extremely large number of polynucleotides, all of which encode the engineered decarboxylase polypeptides disclosed herein. Thus, upon determination of a particular amino acid sequence, one skilled in the art can generate any number of different polynucleotides by merely modifying one or more codons in a manner that does not alter the amino acid sequence of the protein. In this regard, this disclosure specifically contemplates each and every possible alteration of a polynucleotide that can be made by selecting a combination based on possible codon selections, for any of the polypeptides disclosed herein, comprising those amino acid sequences of exemplary engineered polypeptides listed in Table 1, and any of the polypeptides disclosed as even sequence identifiers of SEQ ID NO: 4 to 390 in the Sequence Listing incorporated by reference, all of which are believed to be particularly public.

In various embodiments, the codons are preferably selected to accommodate the host cell in which the recombinant protein is produced. For example, codons preferred for bacteria are used to express genes in bacteria; codons preferred for yeast are used to express genes in yeast; and codons preferred for mammals are used for gene expression in mammalian cells.

In some embodiments, the polynucleotides encode polypeptides comprising amino acid sequences that are at least about 80%, 85%, 86%, 87%, 88%, 89%, 90%, 91%, 92%, 93%, 94%, 95%, 96%, 97%, 98%, 99% or more identical to a reference sequence that is an even sequence identifier of SEQ ID NO: 4-390, wherein the polypeptides have decarboxylase activity and one or more of the improved properties described herein, for example, the ability to convert compound A1 to compound A2 with increased activity compared to the polypeptide of SEQ ID NO: 2.

In some embodiments, the polynucleotides encode engineered decarboxylase polypeptides comprising amino acid sequences having a percentage of identity described above and having one or more amino acid residue differences as compared to SEQ ID NO: 2. In some embodiments, the present disclosure provides engineered polypeptides having decarboxylase activity, wherein the engineered polypeptides comprise a combination that has at least 80% sequence identity to the reference sequence of SEQ ID NO: 2 with residue differences that is selected from the following positions: X2, X3, X4, X6, X8, X15, X18, X21, X29, X30, X33, X34, X39, X40, X45, X46, X53, X64, X67, X68, X70, X80, X81, X91, X92, X93, X99, X100, X102, X103, X104, X106, X109, X110, X111, X113, X114, X115, X116, X117, X118, X119, X121, X122, X124, X125, X126, X127, X128, X130, X132, X133, X135, X136.

In some embodiments, the polynucleotide encoding the engineered decarboxylase polypeptide comprises sequences having odd sequence identifier of SEQ ID NOs: 3-389.

In some embodiments, the polynucleotides encode polypeptides as described herein; but at the nucleotide level, the polynucleotides have about 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to reference polynucleotides encoding engineered decarboxylase polypeptides as described herein. In some embodiments, the reference polynucleotides are selected from the sequences having the odd sequence identifiers of SEQ ID NO: 3-389.

The isolated polynucleotides encoding engineered decarboxylase polypeptides can be manipulated to enable the expression of the engineered polypeptides in a variety of ways, which comprises further modification of the sequences by codon optimization to improve expression, insertion into suitable expression elements with or without additional control sequences, and transformation into a host cell suitable for expression and production of the engineered polypeptides.

Depending on the expression vector, manipulation of the isolated polynucleotide prior to insertion of the isolated polynucleotide into the vector may be desirable or necessary. Techniques for modifying polynucleotides and nucleic acid sequences using recombinant DNA methods are well known in the art. Guidance is provided below: Sambrook et al., 2001, Molecular Cloning: A Laboratory Manual, Third Edition, Cold Spring Harbor Laboratory Press; and Current Protocols in Molecular Biology, Ausubel. F. Eds., Greene Pub. Associates, 1998, 2010 Year update.

In another aspect, this disclosure also relates to recombinant expression vectors, depending on the type of host they are to be introduced into, including a polynucleotide encoding an engineered decarboxylase polypeptide or variant thereof, and one or more expression regulatory regions, such as promoters and terminators, origin of replication and the like. Alternatively, the nucleic acid sequence of the present disclosure can be expressed by inserting the nucleic acid sequence or the nucleic acid construct comprising the sequence into an appropriate expression vector. In generating the expression vector, the coding sequence is located in the vector such that the coding sequence is linked to a suitable control sequence for expression.

The recombinant expression vector can be any vector (e.g., a plasmid or virus) that can be conveniently used in recombinant DNA procedures and can result in the expression of a polynucleotide sequence. The choice of vector will generally depend on the compatibility of the vector with the host cell to be introduced into. The vector can be linear or closed circular plasmid. The expression vector may be an autonomously replicating vector, i.e., a vector that exists as an extrachromosomal entity whose replication is independent of chromosomal replication such as plasmids, extrachromosomal elements, minichromosomes, or artificial chromosomes. The vector may contain any elements for ensuring self-replication. Alternatively, the vector may be a vector that, when introduced into a host cell, integrates into the genome and replicates with the chromosome into which it is integrated. Moreover, a single vector or plasmid or two or more vectors or plasmids that together comprise the total DNA to be introduced into the genome of the host cell may be used.

Many expression vectors useful to the embodiments of the present disclosure are commercially available. An exemplary expression vector can be prepared by inserting a polynucleotide encoding an engineered decarboxylase polypeptide to plasmid pACYC-Duet-1 (Novagen).

In another aspect, this disclosure provides host cells comprising polynucleotides encoding engineered decarboxylase polypeptides of the present disclosure. The polynucleotide is linked to one or more control sequences for expression of decarboxylase polypeptides in a host cell. Host cells for expression of polypeptides encoded by the expression vectors of the present disclosure are well known in the art, including, but not limited to, bacterial cells such as *E. coli, Arthrobacter* KNK168, *Streptomyces,* and *Salmonella typhimurium* cells; fungal cells such as yeast cells (e.g., *Saccharomyces cerevisiae* or *Pichia pastoris*); insect cells such as *Drosophila* S2 and *Spodoptera* Sf9 cells; animal cells such as CHO, COS, BHK, 293 and Bowes melanoma cells; and plant cells. An exemplary host cell is *E. coli* BL21 (DE3). The above host cells may be wild-type or may be engineered cells through genomic edition, such as knockout of the wild-type decarboxylase gene carried in the host cell's genome. Suitable media and growth conditions for the above host cells are well known in the art.

Polynucleotides used to express engineered decarboxylases can be introduced into cells by a variety of methods known in the art. Techniques comprise, among others, electroporation, bio-particle bombardment, liposome-mediated transfection, calcium chloride transfection, and protoplast fusion. Different methods of introducing polynucleotides into cells are obvious to those skilled in the art.

4. Process of Producing an Engineered Decarboxylase Polypeptide

Engineered decarboxylase can be obtained by subjecting a polynucleotide encoding a decarboxylase to mutagenesis and/or directed evolution. An exemplary direction evolution technique can be found in "Biocatalysis for the Pharmaceutical Industry: Discovery, Development, and Manufacturing" (2009 John Wiley & Sons Asia (Pte) Ltd. ISBN: 978-0-470-82314-9).

When the sequence of an engineered polypeptide is known, the encoding polynucleotide may be prepared by standard solid-phase methods according to known synthetic methods. In some embodiments, fragments of up to about 100 bases can be synthesized separately and then ligated (e.g., by enzymatic or chemical ligation methods or polymerase-mediated methods) to form any desired contiguous sequence. For example, the polynucleotides and oligonucleotides of the present disclosure can be prepared by chemical synthesis using, for example, the classic phosphoramidite methods described by Beaucage et al., 1981, Tet Lett 22: 1859-69, or Matthes et al. People, 1984, EMBO J. 3: 801-05, as typically practiced in automated synthesis methods. According to the phosphoramidite method, oligonucleotides are synthesized, purified, annealed, ligated, and cloned into a suitable vector, for example, in an automated DNA synthesizer. In addition, essentially any nucleic acid is available from any of a variety of commercial sources.

In some embodiments, the present disclosure also provides a process for preparing or producing an engineered decarboxylase polypeptide that is capable of converting Compound A1 to Compound A2 under suitable reaction conditions, wherein the process comprises culturing a host cell capable of expressing a polynucleotide encoding an engineered polypeptide under culture conditions suitable for the expression of the polypeptide, and these host cells can be directly applied to the process of converting the compound A1 into the compound A2 in the form of wet cell. In some embodiments, the process of preparing a polypeptide further comprises isolating the polypeptide. Engineered polypeptides may be expressed in suitable cells and isolated (or recovered) from the host cell and/or culture medium using any one or more of the well-known techniques for protein purification, the techniques for protein purification include, among others, lysozyme treatment, ultrasonication, homogenization, filtration, salting out, ultracentrifugation and chromatography.

5. Methods of Using an Engineered Decarboxylase and Compounds Prepared Therewith In another aspect, the engineered decarboxylase polypeptides described herein can catalyze the decarboxylation of an amino acid to form an amino compound.

The present disclosure also provides process of preparing a wide range of compounds (1) or structural analogs thereof using an engineered decarboxylase polypeptide disclosed herein. In some embodiments, engineered decarboxylase polypeptides can be used in a process of preparing a compound of structural formula (I):

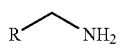
(I)

wherein R is optionally substituted or unsubstituted $C_1$-$C_8$ alkyl, or optionally substituted or unsubstituted aryl or heteroaryl; the process herein comprises that, under suitable reaction conditions, the amino acid substrate of formula (II):

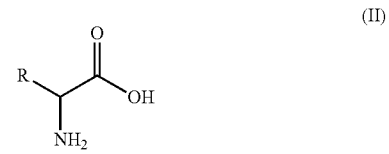
(II)

are contacted with decarboxylase polypeptide, wherein the decarboxylase polypeptide is an engineered decarboxylase polypeptide described herein. In some embodiments, the engineered decarboxylase polypeptide has at least 80%, 85%, 86%, 87%, 88%, 89%, 90%, 91%, 92%, 93%, 94%, 95%, 96%, 97%, 98%, 99% or more of sequence identity with SEQ ID NO:2, and are capable of converting a compound of formula (II) to the compound of formula (I) with a higher conversion rate than SEQ ID NO:2.

As noted above, decarboxylase polypeptides useful in the process of the present disclosure may be characterized according to the ability of converting L-aspartic acid to β-alanine. Thus, in any of the embodiments of the process disclosed herein, the process may be carried out, wherein the decarboxylase polypeptide are capable of converting L-aspartic acid to β-alanine with better catalytic performance than SEQ ID NO:2, and have at least 80%, 85%, 86%, 87%, 88%, 89%, 90%, 91%, 92%, 93%, 94%, 95%, 96%, 97%, 98%, 99% or more of sequence identity with SEQ ID NO:2.

In some embodiments of the process, the amino product of formula (I) is γ-aminobutyric acid:

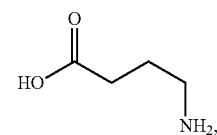

and the amino acid substrate of formula (II) is glutamate (or glutamic acid):

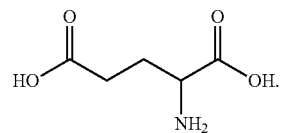

In some embodiments, the engineered decarboxylase polypeptide can be used in a process of preparing β-alanine:

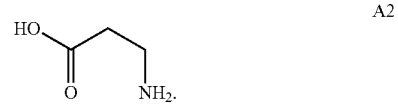
A2

In these embodiments, the process herein comprises that, under suitable reaction conditions, the compound of formula A1:

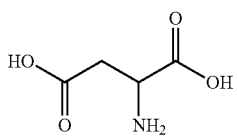

A1 are contacted with the engineered decarboxylase polypeptide disclosed herein.

Specific embodiments of engineered decarboxylase polypeptides for use in the process are further provided in the detailed description. Improved engineered decarboxylase polypeptides that can be used in the above process comprise amino acid sequences selected from SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390.

As described above, engineered polypeptides having decarboxylase activity for use in the process of the present disclosure generally comprises amino acid sequences that have at least 80%, 85%, 86%, 87%, 88%, 89%, 90%, 91%, 92%, 93%, 94%, 95%, 96%, 97%, 98% or 99% sequence identity to the reference amino acid sequence selected from any one of the even numbered sequences of SEQ ID NO: 4 to 390.

As described herein and exemplified in the examples, the present disclosure contemplates a range of suitable reaction conditions that may be used in the process herein, including but not limited to pH, temperature, buffers, solvent systems, substrate loadings, polypeptide loading, and reaction time. Additional suitable reaction conditions for performing a method of enzymatically converting substrate compounds to a product compound using engineered decarboxylase polypeptides described herein can be readily optimized by routine experimentation, which including but not limited to that the engineered decarboxylase polypeptide is contacted with substrate compounds under experimental reaction conditions of varying concentration, pH, temperature, solvent conditions, and the product compound is detected, for example, using the methods described in the Examples provided herein.

The substrate compounds in the reaction mixture can be varied, taking into consideration of, for example, the amount of the desired product compound, the effect of the substrate concentration on the enzyme activity, the stability of the enzyme under the reaction conditions, and the percent conversion of substrate to product. In some embodiments of the process, the suitable reaction conditions include at least about 0.5 to about 400 g/L, about 1 to about 400 g/L, about 5 to about 400 g/L, about 10 to about 400 g/L, or about 50 to about 400 g/L of loading of substrate (II) or substrate A1. In some embodiments, suitable reaction conditions include at least about 0.5 g/L, at least about 1 g/L, at least about 5 g/L, at least about 10 g/L, at least about 15 g/L, at least about 20 g/L, at least about 100 g/L, at least about 150 g/L, at least about 200 g/L, at least about 250 g/L, at least about 300 g/L, at least about 350 g/L, at least about 400 g/L or even more of loading of substrate (II) or substrate A1. The values for the substrate loading provided herein are based on the molecular weight of compound (II) or A1, however it is also contemplated that the equivalent molar amounts of various hydrates and salts of compound (II) or A1 may also be used in the process.

In the process described herein, the engineered decarboxylase polypeptide catalyzes the decarboxylation of an amino acid to form a product. In some embodiments, the amino acids in the reaction conditions include compounds selected from D, L-aspartic acid, D, L-glutamic acid, D,L-cysteine, D,L-leucine, D,L-isoleucine, D, L-methionine, D, L-threonine or D, L-valine.

In the embodiments of the reaction, the reaction conditions may include a suitable pH. As noted above, the desired pH or desired pH range can be maintained by using an acid or base, a suitable buffer, or a combination of buffer and added acid or base. The pH of the reaction mixture can be controlled before and/or during the reaction. In some embodiments, suitable reaction conditions include a solution pH of about 4 to about 8, a pH of about 5 to about 7, a pH of about 6 to about 7. In some embodiments, the reaction conditions include a solution pH of about 4, 4.5, 5, 5.5, 6, 6.5, 7, 7.5 or 8.

In embodiments of the processes herein, suitable temperatures can be used for the reaction conditions, taking into consideration of, for example, the increase in reaction rate at higher temperatures, the activity of the enzyme for sufficient duration of the reaction.

Accordingly, in some embodiments, suitable reaction conditions include a temperature of about 10° C. to about 60° C., about 25° C. to about 50° C., about 25° C. to about 40° C., or about 25° C. to about 30° C. In some embodiments, suitable reaction temperatures include a temperature of about 25° C., 30° C., 35° C., 40° C., 45° C., 50° C., 55° C., or 60° C. In some embodiments, the temperature during the enzymatic reaction can be maintained at a certain temperature throughout the reaction. In some embodiments, the temperature during the enzymatic reaction may be adjusted over a temperature profile during the course of the reaction.

The processes of using the engineered decarboxylase are generally carried out in a solvent. Suitable solvents include water, aqueous buffer solutions, organic solvents, and/or co-solvent systems, which generally include aqueous solvents and organic solvents. The aqueous solutions (water or aqueous co-solvent systems) can be pH-buffered or unbuffered. In some embodiments, the processes of using an engineered decarboxylase polypeptide are generally carried out in an aqueous co-solvent system comprising an organic solvent (e.g., methanol, ethanol, propanol, isopropanol (IPA), dimethyl sulfoxide (DMSO), dimethylformamide (DMF), isopropyl acetate, ethyl acetate, butyl acetate, 1-octanol, heptane, octane, methyl tert-butyl ether (MTBE), Toluene, etc.), ionic liquids (for example, 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of the aqueous co-solvent system may be miscible with the aqueous component, providing a single liquid phase, or may be partially miscible or immiscible with the aqueous component, providing two liquid phases. The carbon dioxide generated during the decarboxylation reaction may cause foam formation, and an antifoaming agent may be appropriately added. Exemplary aqueous co-solvent system comprises water and one or more organic solvents. In general, the organic solvent component of the aqueous co-solvent system is selected such that it does not completely inactivate the decarboxylase. Suitable co-solvent system can be readily identified by measuring the enzymatic activity of a particular engineered decarboxylase with a defined substrate of interest in the candidate solvent system, utilizing enzymatic activity assays, such as those described herein. In some embodiments of the process, suitable reaction conditions include an aqueous co-solvent comprising ethanol at a concentration of about 1% to about 100% (v/v), about 1% to about 60% (v/v), about 2% to about 60% (v/v), about 5% to about 60% (v/v), from about 10% to about 60% (v/v), from about 10% to about 50% (v/v), or about 10% to about 40% (v/v). In some embodiments of the process, suitable reaction conditions include an aqueous co-solvent comprising ethanol at a concentration of at least about 1%, 5%, 10%, 15%, 20%, 25%, 30%, 35%, 40%, 45%, 50%, 55%, or 60% (v/v).

Suitable reaction conditions can include a combination of reaction parameters that provide for the biocatalytic conversion of the substrate compounds to its corresponding product compound. Accordingly, in some embodiments of the process, the combination of reaction parameters comprises: (a) substrate A1 loading of about 10 g/L to about 200 g/L; (b) engineered polypeptide concentration of about 0.5 g/L to 10 g/L; (c) pH of about 4.0 to 8.0; and (d) temperature of about 10° C. to 60° C.

Exemplary reaction conditions include the assay conditions provided in Table 2 and Example 3.

In carrying out the decarboxylation reaction described herein, the engineered decarboxylase polypeptide may be added to the reaction mixture in the partially purified or purified forms, whole cells transformed with the gene encoding the engineered decarboxylase polypeptide, and/or as cell extracts and/or lysates of such cells. Whole cells transformed with the gene encoding the engineered decarboxylase or cell extracts, lysates thereof, and isolated enzymes can be used in a wide variety of different forms, including solids (e.g., lyophilized, spray dried, or the like) or semisolid (e.g., a crude paste such as wet cells). The cell extract or cell lysate may be partially purified by precipitation (e.g., ammonium sulfate, polyethyleneimine, heat treatment or the like), followed by desalting procedures (e.g., ultrafiltration, dialysis, and the like) prior to lyophilization. Any of the enzyme preparations can be stabilized by cross-linking using known crosslinking agents, such as glutaraldehyde, or immobilization to a solid phase material (such as a resin).

In some embodiments of the decarboxylation reactions described herein, the reaction is performed under suitable reaction conditions described herein, wherein the engineered decarboxylase polypeptide is immobilized to a solid support. Solid supports useful for immobilizing the engineered decarboxylase enzyme for carrying out the reaction include but are not limited to beads or resins such as polymethacrylates with epoxy functional groups, polymethacrylates with amino epoxy functional groups, polymethacrylates, styrene/DVB copolymer or polymethacrylates with octadecyl functional groups.

Exemplary solid supports include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, wherein an engineered polypeptide is expressed in the form of a secreted polypeptide, a culture medium containing the secreted polypeptide can be used in the process herein.

In some embodiments, the solid reactants (e.g., enzymes, salts, etc.) can be provided to the reaction in a variety of different forms, including powders (e.g., lyophilized, spray dried, etc.), solutions, emulsions, suspensions and the like. The reactants can be readily lyophilized or spray-dried using methods and instrumentation known to one skilled in the art. For example, the protein solution can be frozen at −80° C. in small aliquots, and then added to the pre-chilled lyophilization chamber, followed by the application of a vacuum.

In some embodiments, the order of addition of reactants is not critical. The reactants may be added together to the solvent at the same time (e.g., monophasic solvent, a biphasic aqueous co-solvent system, etc.), or alternatively, some reactants may be added separately, and some may be added together at different time points. For example, the decarboxylase and substrate may be added first to the solvent; the organic phase can then be added and mixed.

Alternatively, the substrates can be premixed in the organic phase prior to addition to the aqueous phase.

EXAMPLES

The following examples further illustrate the present invention, but the present invention is not limited thereto. In the following examples, experimental methods with conditions not specified, were conducted at the commonly used conditions or according to the supplier's' suggestion.

Example 1: Gene Cloning and Construction of Expression Vectors

The amino acid sequence of the wild-type decarboxylase derived from *Corynebacterium glutamicum* can be retrieved from NCBI, and the corresponding nucleic acids were then synthesized by a vendor using conventional techniques in the art and cloned into the expression vector pACYC-Duet-1. The recombinant expression plasmid was transformed into *E. coli* BL21 (DE3) competent cells under the conditions of 42° C. and thermal shock for 90 seconds. The transformation solution was plated on LB agar plates containing chloramphenicol which was then incubated overnight at 37° C. Recombinant transformants were obtained.

Example 2: Expression of a Decarboxylase Polypeptide, and Preparation of Wet Cell Expressing a Decarboxylase Polypeptide The wet cell preparation step of the present invention is as follows: the recombinant *E. coli* BL21 (DE3) obtained in Example 1 was inoculated into 50 mL of LB medium containing chloramphenicol (peptone 10 g/L, yeast extract powder 5 g/L, chlorinated sodium 10 g/L, pH 7.0±0.2, 25° C.) in a 250 mL Erlenmeyer flask. which was then shaken at 30° C., at 250 rpm overnight. When the $OD_{600}$ of subculture broth reached 2, The culture was subcultured into a 1000 mL flask containing 250 mL of TB medium (tryptone 12 g/L, yeast extract 24 g/L, disodium hydrogen phosphate 9.4 g/L, dipotassium hydrogen phosphate 2.2 g/L, pH 7.2±0.2, 30° C.) at 30° C., 250 rpm in a shaking incubator. When the $OD_{600}$ of subculture broth reached 0.6~0.8, IPTG was added at a final concentration of 1 mM as an inducer. After induction at 30° C. for 20 h, the culture solution was centrifuged (8000 rpm, 10 minutes); the supernatant was discarded after centrifugation, and the cell pellet was collected to obtain wet cells. The obtained wet cells can be directly used for the reaction or placed in a refrigerator at −20° C. for use.

According to the recombinant expression process using shaking flasks as mentioned above, a miniaturized expression process in 96-well plate was performed by proportionally reducing the scale. and the supernatant medium was centrifuged to obtain wet cells. If necessary, the enzyme solution can be obtained by crushing.

Example 3: HPLC and LC/MS Analysis Methods

HPLC analysis method: analytical column is Chilex-3126 30 mm×4.6 um, mobile phase is 3 mM CuSO4, flow rate is 1.2 mL/min, column temperature is 45° C., detection wavelength is 230 nm, and analysis time is 4 min. The retention time of β-alanine is 1.45 min, and the retention time of L-aspartic acid is 2.5 min.

LC/MS analysis method: LC detection wavelength is 230 nm, column temperature is 30° C., flow rate 1 is mL/min, mobile phase A is 70% of 0.1% formic acid aqueous solution (pH 2.75), and mobile phase B is 30% of 0.1% formic acid in methanol. Mass spectrometry method is MRM, in which the substrate has a parent-to-charge ratio of 134.1, a mass-to-charge ratio of 73.9, a cone voltage of 20 V, a collision cell voltage of 18 V, a product parent-to-charge ratio of 89.97, a mass-to-charge ratio of 71.8, and a cone voltage of 20 V. The collision cell voltage was 12V, the injection volume was 10 uL, the detection time was 1.67 min, and the peak time of β-alanine and L-aspartic acid was 0.25 min.

Example 4: Construction of a Decarboxylase Mutant Library

Quikchange kit (supplier: Agilent) was preferably used here. The sequence design of the mutagenesis primers was performed according to the instructions of the kit. The construction of a saturated mutant library with a single residue position is now illustrated as an example. The PCR system consisted of 10 µl of 5× Buffer, 1 µl of 10 mM dNTP, 1 µl of plasmid DNA template (50 ng/µl), 0.75 µl (10 uM) each of the upstream and downstream primers, 0.5 µl of high fidelity enzyme and 36 µl of ddH2O, The PCR primer has a NNK codon at the mutation position. PCR amplification steps: (1) 98° C. pre-denaturation 3 min; (2) 98° C. denaturation 10s; (3) annealing and extension 3 min at 72° C.; steps of (2) ~ (3) repeated 25 times; (5) extension 10 min at 72° C.; (6) cooling to 4° C., 2 µl of DpnI was added to the PCR product and the plasmid template was eliminated by overnight digestion at 37° C. The digested PCR product was transformed into E. coli BL21 (DE3) competent cells and plated on LB agar plates containing chloramphenicol to obtain a saturated mutant library of the target residue position.

Example 5 Screening of Mutant Enzyme Library

Colonies of the mutant enzyme library were picked from the agar plates, inoculated into LB medium containing chloramphenicol in a 96-well shallow plates (200 µl LB medium per well), placed in a shaker at 180 rpm, 80% humidity, 30° C. overnight, and cultured for 18 to 20 hours. When the OD$_{600}$ of the culture solution reached 2-3, 20 µl of the culture solution were taken from a 96-well shallow plate and inoculated into TB medium containing chloramphenicol in a 96-well deep-well plate (400 µl TB medium per well), placed in a shaker at 250 rpm, and incubated at 30° C. and humidity of 80%. When the OD$_{600}$ of the culture solution reached 0.6-0.8, IPTG was added as an inducer at the final concentration of 1 mM, and the expression undertook in a shaker at 250 rpm, humidity of 80%, and 30° C. overnight (18-20 hr). Once the overnight expression was done, the culture was centrifuged at 4000 rpm for 10 min to obtain cell pellets (i.e. wet cells). The wet cells were placed in a −20° C. freezer for use.

The screening assay was carried out as following: prepare a 40 g/L L-aspartic acid solution, and the pH of the solution was adjusted to 6 with ammonia water or hydrochloric acid Then, it was placed in a refrigerator at 4° C. for later use. The above-prepared 96-well plate containing the wet cells was taken out from the −20° C. refrigerator, 400 µl of pure water was added to each well with a dispenser, and then the plate was heat sealed with a membrane and shaken at 700 rpm on a plate shaker for 10 min to resuspend the cells. 20 µl of the cell suspension was then taken into a fresh deep-well plate, and 100 µl of the above-prepared L-aspartic acid solution was added into the deep-well plate. Finally, PBS buffer was added to the reaction to make total reaction volume of 200 µl/well with 0.1M PBS of pH 7. Then, the reaction was carried out for 16 hours at a rotation speed of 250 rpm in a 50° C. shaker, followed by LC/MS analysis to detect product formation.

Example 6 Process for the Preparation of β-Alanine Catalyzed by Engineered Decarboxylase Polypeptide 5 g of the wet cells expressing the polypeptide of SEQ ID No: 360 were resuspended with water to a final volume of 150 mL. 50 g of L-aspartic acid were added into 300 mL of pure water, and then its pH was adjusted to 6.0-7.0 with ammonia and its final volume was adjusted to 350 mL with water. To this solution of L-aspartic acid, the above-prepared 150 mL cell suspension were added to start the reaction, and during the reaction 21% phosphoric acid solution was dosed to control the pH of reaction solution between 6.0 and 7.0. The temperature of reaction was controlled at 40° C. to 50° C. After 24 hours of reaction, the conversion of L-aspartic acid to β-alanine was 95%.

Example 7: Screening Assay for Overcoming Substrate or Product Inhibition

A mixture solution of 200 g/L of L-aspartic acid and 200 g/L of β-alanine was prepared, and the pH of the solution was adjusted to 6 with ammonia and/or hydrochloric acid during the preparation, and then it was placed in a refrigerator at 4° C. for later use. Similar to the procedure shown in Example 5, wet cells in 96-well plate were resuspended in water, and 80 µl of cell suspension was taken into a fresh deep-well plate. To each well of this plate, 1001 of the above-prepared mixture solution of L-aspartic acid and β-alanine was added. the buffer of the reaction system is 0.3M PBS of pH 6, The total volume of reaction solution was 200 µl, Finally, PBS buffer was added to the reaction to make total reaction volume of 200 µl/well with 0.3M PBS of pH 6. Then, the reaction was carried out for 16 hours at 250 rpm on a 50° C. shaker, followed by LC/MS or HPLC analysis to detect product formation.

Example 8: Fermentation Process for the Expression of Engineered Decarboxylase Polypeptide A single microbial colony of E. coli BL21 (DE3) containing the expression plasmid bearing the target decarboxylase polypeptide was inoculated into 50 mL LB broth containing 30 µg/mL chloramphenicol (5.0 g/L Yeast Extract LP0021, 10 g/L Tryptone LP0042, 10 g/L sodium chloride). The cells were cultured overnight (at least 16 hours) with shaking at 250 rpm in a 30° C. shaker.

A 5 L fermenter containing 2.0 L of growth medium was sterilized in a 121° C. autoclave for 30 minutes. The fermenter was inoculated with overnight cultured E. coli (grown in shake flasks as described above to an initial $OD_{600}$ of 1.4 to 2.0).

Temperature of fermenter was maintained at 30° C. which was controlled by jacketed circulating water. The growth medium in fermenter was agitated at 200-800 rpm and air was supplied at 2-8 L/min to maintain the dissolved oxygen level at 40% of saturation or greater. The culture was maintained at pH 7.0 by addition of 25-28% v/v ammonium hydroxide. Cell growth was maintained by feeding a feed solution containing 500 g/L of dextrose glucose monohydrate, 12 g/L ammonium chloride, and 5 g/L magnesium sulfate heptahydrate. After the $OD_{600}$ of culture reached 25±5, the temperature of fermenter was maintained at 30° C., and the expression of decarboxylase was induced by the addition of isopropyl-β-D-thiogalactoside (IPTG) to a final concentration of 1 mM. Fermentation process then continued for additional 18 hours. After the fermentation process was complete, cells were harvested using a using a Thermo MuLtifuge X3R centrifuge at 8000 rpm for 10 minutes at 4° C. Harvested cells were used directly in the reaction process, or can be stored frozen at −20° C.

Example 9: Process for the Decarboxylation of Glutamic Acid to Produce γ-Aminobutyric Acid Catalyzed by Engineering Decarboxylase Polypeptide A 10 g/L L-glutamic acid solution was prepared, and the pH was adjusted to 6 with KOH during the preparation. 200 mg of the wet cell expressing the polypeptide of SEQ ID No: 164 was added to the reaction flask, and 2.5 mL of the L-glutamic acid solution prepared above was added to the reaction flask, and pure water was added to top the total volume of reaction solution to 5.0 mL. The reaction proceeded with the temperature of 30° C. and stirring speed of 400 rpm.

After 20 hours of reaction, it was stopped by heating at 95° C. for 10 min. Then, an aliquot of the reaction was diluted with 0.3% hydrochloric acid to the detection concentration, followed by HPLC analysis. The conversion of L-glutamic acid to γ-aminobutyric acid was ≥70%. The HPLC analysis method was as follows. Column: Elite-NH2 150*4.6 mm, mobile phase: [acetonitrile: 0.02M potassium dihydrogen phosphate solution of pH 3.5=65:35], column temperature 30° C., detection wavelength 205 nm, flow rate 1.5 mL/min.

It should be understood that after reading the above contents of the present invention, those skilled in the art may make various modifications or changes to the present invention. And these equivalent forms also fall within the scope of the appended claims of the present invention.

The amino acid sequences listed in Table 1 (i.e., the even sequence identifiers of SEQ ID NO: 2 to 384) each contain 136 amino acid residues. SEQ ID NO: 386, 388, or 390 has a different number of deletion or substitution of amino acid residues as compared to SEQ ID No: 2. Under the reaction conditions shown in Table 2, the engineered decarboxylase polypeptide of SEQ ID NO: 386, 388, or 390 has higher catalytic performance than that of SEQ ID No: 2. The wet cells described in Table 2 refer to wet cells in which the decarboxylase polypeptide corresponding to the amino acid sequence in Table 1 was expressed in equal amount.

3. Polynucleotides, Control Sequences, Expression Vectors and Host Cells that can be Used to Produce Engineered Decarboxylase Polypeptides In another aspect, this disclosure provides polynucleotides encoding engineered polypeptides having decarboxylase activity described herein. The polynucleotides can be linked to one or more heterologous regulatory

The invention claimed is:

1. An engineered decarboxylase polypeptide that catalyzes the decarboxylation of L-aspartic acid to produce β-alanine, wherein said polypeptide comprises an X109T substitution relative to SEQ ID NO:2, further wherein said amino acid sequence is selected from the group consisting of SEQ ID NOs: 44, 48, 50, 52, 54, 60, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, and 384.

2. The engineered decarboxylase polypeptide of claim 1, wherein said polypeptide is, under suitable reaction conditions, capable of decarboxylating L-aspartic acid to produce β-alanine at greater activity and/or stability than the wild type L-aspartate-α-decarboxylase derived from Corynebacterium glutamicum set forth in SEQ ID NO: 2.

3. The decarboxylase polypeptide of claim 2, wherein the suitable reaction conditions include 5 g/L to 400 g/L of L-aspartic acid, pH of 4.0 to 8.0, and temperature of 10-60° C.

4. A polypeptide immobilized on a solid material by a chemical bond or a physical adsorption method, wherein the polypeptide comprises the decarboxylase polypeptide according to claim 1.

5. A process of preparing a compound of formula (I):

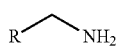
(I)

wherein R is an optionally substituted or unsubstituted $C_1$-$C_8$ hydrocarbyl, or an optionally substituted or unsubstituted aryl or heteroaryl; wherein the process comprises the step of contacting, under suitable reaction conditions, the amino acid substrate of formula (II):

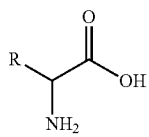
(II)

with the engineered polypeptide of claim 1.

6. The process of claim 5, wherein the product of formula (I) is γ-aminobutyric acid:

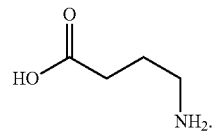

7. A process for preparing a compound of formula A2, β-alanine:

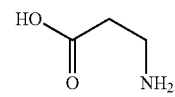
A2 wherein the process comprises the step of contacting, under suitable reaction conditions, a compound of formula A1

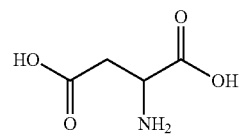
A1 with an engineered decarboxylase polypeptide of claim 1 and converting said compound of formula A1 to a compound of formula A2.

8. The process of claim 5, wherein the reaction solvent is selected from the group consisting of comprises water, methanol, ethanol, propanol, isopropanol, isopropyl acetate, dimethyl sulfoxide (DMSO) and dimethylformamide (DMF).

9. The process of claim 5, wherein the reaction conditions include a temperature of 10° C. to 60° C.

10. The process of claim 5, wherein the reaction conditions include a pH of 4.0 to pH 8.0.

11. The process of claim 5, wherein the substrate is present at a loading of 5 g/L to 400 g/L.

12. An engineered decarboxylase polypeptide that catalyzes the decarboxylation of L-aspartic acid to produce β-alanine, wherein said polypeptide comprises the amino acid sequence set forth in SEQ ID NO: 4.

* * * * *

UNITED STATES PATENT AND TRADEMARK OFFICE
CERTIFICATE OF CORRECTION

PATENT NO. : 11,332,730 B2
APPLICATION NO. : 16/648919
DATED : May 17, 2022
INVENTOR(S) : Haibin Chen et al.

It is certified that error appears in the above-identified patent and that said Letters Patent is hereby corrected as shown below:

In the Specification

At Column 1, Line 67, replace the term "3-alanine" with the term -- β-alanine --.

At Column 3, Line 38, replace the term "V1061" with the term -- V106I --.

At Column 3, Line 44, replace the term "L1251" with the term -- L125I --.

At Column 3, Line 44, replace the term "G1271" with the term -- G127I --.

Signed and Sealed this
Fourteenth Day of February, 2023

Katherine Kelly Vidal
*Director of the United States Patent and Trademark Office*